US008148324B2

(12) United States Patent
Greenberg et al.

(10) Patent No.: US 8,148,324 B2
(45) Date of Patent: Apr. 3, 2012

(54) CHEMOENZYMATIC METHODS FOR THE SYNTHESIS OF STATINS AND STATIN INTERMEDIATES

(75) Inventors: William Greenberg, San Diego, CA (US); Mark J. Burk, San Diego, CA (US); Alexander Varvak, San Diego, CA (US); Kelvin Wong, San Diego, CA (US)

(73) Assignee: Verenium Corporation, San Diego, CA (US)

( * ) Notice: Subject to any disclaimer, the term of this patent is extended or adjusted under 35 U.S.C. 154(b) by 789 days.

(21) Appl. No.: 12/032,337

(22) Filed: Feb. 15, 2008

(65) Prior Publication Data

US 2008/0289056 A1 Nov. 20, 2008

Related U.S. Application Data

(62) Division of application No. 10/472,157, filed as application No. PCT/US03/27334 on Aug. 19, 2003, now Pat. No. 7,414,119.

(60) Provisional application No. 60/412,625, filed on Sep. 20, 2002, provisional application No. 60/469,374, filed on May 9, 2003.

(51) Int. Cl.
*C07K 14/00* (2006.01)
*C12P 21/00* (2006.01)
(52) U.S. Cl. .......................................... 514/2; 435/68.1
(58) Field of Classification Search .................. None
See application file for complete search history.

(56) References Cited

U.S. PATENT DOCUMENTS

| 5,256,800 | A | 10/1993 | Kaneko et al. |
| 5,292,891 | A | 3/1994 | Kaneko et al. |
| 5,457,227 | A | 10/1995 | Thottathil et al. |
| 5,795,749 | A | 8/1998 | Wong et al. |
| 5,998,633 | A | 12/1999 | Jacks et al. |
| 6,033,883 | A | 3/2000 | Barr et al. |
| 7,026,121 | B1 | 4/2006 | Wohlgemuth et al. |
| 2003/0053950 | A1 | 3/2003 | Leyland-Jones |
| 2003/0158426 | A1 | 8/2003 | Kooistra et al. |
| 2003/0229044 | A1 | 12/2003 | Steinman et al. |
| 2003/0232416 | A1 | 12/2003 | Wong et al. |
| 2004/0063175 | A1 | 4/2004 | Abraham et al. |

FOREIGN PATENT DOCUMENTS

| EP | 0521471 | 10/2000 |
| JP | 2001-328984 | 11/2001 |
| WO | 96/31615 A1 | 10/1996 |
| WO | WO0053553 | 9/2000 |
| WO | WO01/90333 | 11/2001 |
| WO | WO-02/06266 | 1/2002 |
| WO | WO02/068583 | 9/2002 |
| WO | WO-03/006656 | 1/2003 |
| WO | 2006/066072 | 6/2006 |

OTHER PUBLICATIONS

Shannon—J. Biological Chem. (1962)—237—3342-3347.
PCT/US2007/63515—International Preliminary Examination Report (IPER) Mailed Jul. 2, 2009.
EP07758102—EP Supplementary Search Report—Mailed May 7, 2009.
EMBL Accession No. AB050935—Maruyama—(2001).
UNIPROT Accession No. Q2NXC10—Ochiai—(2006).
Dec. 7, 2009—JP Office Action—Appl. No. 2004568922.
Gijsen—J. Am. Chem. Soc. (1994)—116—8422-8423.
Galperin—FEMS Microbiology Letters (2000)—183—259-264.
Radl—Tetrahedron Letters (2002)—43—2087-2090.
Barbas III et al., PNAS USA (1991) 88:7978-7982.
Bennett et al., J. Chem. Soc. Perkin Trans. (1991) 1:133-140.
Brinkkotter et al., Arch. Microbiol. (2002) 177:410-419.
Brower et al., Tetrahedron Letters (1992) 33(17):2279-2282.
Chappel et al., J. Inher. Metab. Dis. (1983) 6:105-107.
Deckert et al., Nature (1988) 392:353-358, Accession AE000657.1 and peptide GI No. 2982875.
Desantis et al., Bioorganic and Medicinal Chemistry (2003) 11:43-52.
Evans et al., Top. Stereochem. (1982) 13:1-115.
Evans, Science (1988) 240:420-426.
Fessner and Helaine, Current Opinion in Biotechnology (2001) 12:574-586.
Fong et al., Chemistry and Biology (2000) 7:873-883.
Gefflaut et al., Prog. Biophys. Molec. Biol. (1995) 63:301-340.
Gijsen and Wong, J. Am. Chem. Soc. (1995) 117:7585-7591.
Gijsen and Wong, J. Am. Chem. Soc. (1994) 116:8422-8423.
Heathcock, Aldrichim. Acta (1990) 23:99-111.
Heathcock et al., in Comprehensive Organic Synthesis, vol. 2, B.M. Trost, ed., Pergamon, Oxford, (1991) pp. 133-319.
Heathcock, Science (1981) 214:395-400.
Hoffee, Archives of Biochemistry and Biophysics (1968) 126:795-802.
International Search Report for PCT/US03/27334, mailed on Aug. 28, 2007, 5 pages.
Janda et al., PNAS USA (1994) 191:2532-2536.
Jargiello et al., Archives of Biochemistry and Biophysics (1976) 177:630-641.
Kawarabayasi et al., DNA Research (1999) 6:83-101.
Lai et al., Science (1974) 183:1204-1206.
Liu and Wong, Angew. Chem. Int. Ed. (2002) 41:1404-1407.
Margolin, Enzyme Microb. Technol. (1993) 15:266-280.
Masamune et al., Angew. Chem. Int. Ed. Engl. (1985) 24:1-30.
Mc Cague et al., Tetrahedron Letters (1993) 34:3785-3786. Morris and Tolan, Biochemistry (1994) 33:12291-12297.
Patel, Current Opinion in Biotechnology (2001) 12:587-604.
Paterson, Pure & Applied. Chem. (1992) 64:1821-1830.
Rosen and Heathcock, Tetrahedron (1986) 42:4909-4951.
Rosen et al., J. Org. Chem. (1984) 49:3657-3659.
Rosen et al., J. Org. Chem. (1984) 49:3994-4003.
Saaby et al., J. Org. Chem. (2002) 67:4352-4361.

(Continued)

*Primary Examiner* — Anand Desai

(74) *Attorney, Agent, or Firm* — Verenium Corporation; Brian W. Siddons; Lynn M. Linkowski

(57) ABSTRACT

The invention provides aldolases, nucleic acids encoding them and methods for making and using them, including chemoenzymatic processes for making β,δ-dihydroxyheptanoic acid side chains and compositions comprising these side chains, e.g., [R—(R*,R*)]-2-(4-fluorophenyl)-b,d-dihydroxy-5-(1-methylethyl)-3-phenyl-4-(phenylamino)-carbonyl]-1H-pyrrole-1-heptanoic acid (atorvastatin, LIPITOR™), rosuvastatin (CRESTOR™), fluvastatin (LESCOL™), related compounds and their intermediates.

7 Claims, 21 Drawing Sheets

OTHER PUBLICATIONS

Sakaki et al., Tetrahedron: Asymmetry (1991) 2(5):343-346.
Schmid et al., Current Opinion in Biotechnology (2002) 13:359-366.
Takayama et al., Annu. Rev. Microbiol. (1997) 51:285-310.
Uniprot Accession No. DEOC_AERPE, 2000, (Kawarabayasi et al.) "Probable deoxyribose-phosphate aldolase (EC 4.1.2.4)", 235 AA; 24529 MW.
Wong et al., J. Am. Chem. Soc. (1995) 117:3333-3339.
Wong, Science (1989) 244:1145-1152.
Wymer and Toone, Current Opinion in Chemical Biology (2000) 4:110-119.
Jun. 8, 2009—JP Office Action—Appl. No. 2004568922.
Siebers—Journal of Biological Chemistry (2001)—276—28710-28718.
SIPO—May 20, 2010—Chinese First Office Action and Translation—CN 200780016408.6.
EPO—Mar. 15, 2011—Office Action—EP03797874.9.
UNIPROT Accession No. O66540—Deckert (2002).
GENESEQ Accession No. ABB54781—Bolotine (2001).
UNIPROT Accession No. Q92A19—Glasser (2002).
UNIPROT Accession No. P39121—Yoshida (1995).
UNIPROT Accession No. Q9KD67—Takami (2001).
UNIPROT Accession No. Q8ZJV8—McClelland (2002).
UNIPROT Accession No. Q8Z0U3—Parkhill (2002).
UNIPROT Accession No. P39121—Kunst (1997).
UNIPROT Accession No. Q8UJO9—Goodner (2001).
Wong—J. Am. Chem. Soc. (1995)—117—3333-3339.
Greenberg—PNAS—(2004)—101—5788-5793.
CN200780016408.6—Office Action—May 3, 2011.

Lactone IV    Intermediate X    Atorvastatin XI

SEQUENCE LISTING

<160> NUMBER OF SEQ ID NOS: 30

<210> SEQ ID NO 1
<211> LENGTH: 780
<212> TYPE: DNA
<213> ORGANISM: E. coli

<400> SEQUENCE: 1

```
atgactgatc tgaaagcaag cagcctgcgt gcactgaaat tgatggacct gaccaccctg      60
aatgacgacg acaccgacga gaaagtgatc gccctgtgtc atcaggccaa aactccggtc     120
ggcaataccg ccgctatctg tatctatcct cgctttatcc cgattgctcg caaaactctg     180
aaagagcagg gcaccccgga aatccgtatc gctacggtaa ccaacttccc acacggtaac     240
gacgacatcg acatcgcgct ggcagaaacc cgtgcggcaa tcgcctacgg tgctgatgaa     300
gttgacgttg tgttcccgta ccgcgcgctg atggcgggta acgagcaggt tggttttgac     360
ctggtgaaag cctgtaaaga ggcttgcgcg gcagcgaatg tactgctgaa agtgatcatc     420
gaaaccggcg aactgaaaga cgaagcgctg atccgtaaag cgtctgaaat ctccatcaaa     480
gcgggtgcgg acttcatcaa aacctctacc ggtaaagtgg ctgtgaacgc gacgccggaa     540
agcgcgcgca tcatgatgga agtgatccgt gatatgggcg tagaaaaaac cgttggtttc     600
aaaccggcgg gcggcgtgcg tactgcggaa gatgcgcaga aatatctcgc cattgcagat     660
gaactgttcg gtgctgactg ggcagatgcg cgtcactacc gctttggcgc ttccagcctg     720
ctggcaagcc tgctgaaagc gctgggtcac ggcgacggta agagcgccag cagctactaa     780
```

<210> SEQ ID NO 2
<211> LENGTH: 259
<212> TYPE: PRT
<213> ORGANISM: E. coli

<400> SEQUENCE: 2

```
Met Thr Asp Leu Lys Ala Ser Ser Leu Arg Ala Leu Lys Leu Met Asp
  1               5                  10                  15

Leu Thr Thr Leu Asn Asp Asp Asp Thr Asp Glu Lys Val Ile Ala Leu
                 20                  25                  30

Cys His Gln Ala Lys Thr Pro Val Gly Asn Thr Ala Ala Ile Cys Ile
             35                  40                  45

Tyr Pro Arg Phe Ile Pro Ile Ala Arg Lys Thr Leu Lys Glu Gln Gly
         50                  55                  60

Thr Pro Glu Ile Arg Ile Ala Thr Val Thr Asn Phe Pro His Gly Asn
```

```
                65                  70                  75                  80
Asp Asp Ile Asp Ile Ala Leu Ala Glu Thr Arg Ala Ala Ile Ala Tyr
                    85                  90                  95
Gly Ala Asp Glu Val Asp Val Val Phe Pro Tyr Arg Ala Leu Met Ala
                    100                 105                 110
Gly Asn Glu Gln Val Gly Phe Asp Leu Val Lys Ala Cys Lys Glu Ala
                    115                 120                 125
Cys Ala Ala Ala Asn Val Leu Leu Lys Val Ile Glu Thr Gly Glu
                    130                 135             140
Leu Lys Asp Glu Ala Leu Ile Arg Lys Ala Ser Glu Ile Ser Ile Lys
145                 150                 155                 160
Ala Gly Ala Asp Phe Ile Lys Thr Ser Thr Gly Lys Val Ala Val Asn
                    165                 170                 175
Ala Thr Pro Glu Ser Ala Arg Ile Met Met Glu Val Ile Arg Asp Met
                    180                 185                 190
Gly Val Glu Lys Thr Val Gly Phe Lys Pro Ala Gly Gly Val Arg Thr
                    195                 200                 205
Ala Glu Asp Ala Gln Lys Tyr Leu Ala Ile Ala Asp Glu Leu Phe Gly
                    210                 215                 220
Ala Asp Trp Ala Asp Ala Arg His Tyr Arg Phe Gly Ala Ser Ser Leu
225                 230                 235                 240
Leu Ala Ser Leu Leu Lys Ala Leu Gly His Gly Asp Gly Lys Ser Ala
                    245                 250                 255
Ser Ser Tyr

<210> SEQ ID NO 3
<211> LENGTH: 780
<212> TYPE: DNA
<213> ORGANISM: Artificial Sequence
<220> FEATURE:
<223> OTHER INFORMATION: Synthetically generated oligonucleotide

<400> SEQUENCE: 3
atgactgatc tgaaagcaag cagcctgcgt gcactgaaat tgatggacct gaccaccctg        60
aatgacgacg acaccgacga gaaagtgatc gccctgtgtc atcaggccaa aactccggtc       120
ggcaataccg ccgctatctg tatctatcct cgctttatcc cgattgctcg caaaactctg       180
aaagagcagg gcaccccgga aatccgtatc gctacggtaa ccaacttccc acacggtaac       240
gacgacatcg acatcgcgct ggcagaaacc cgtgcggcaa tcgcctacgg tgctgatgaa       300
gttgacgttg tgttcccgta ccgcgcgctg atggcgggta acgagcaggt tggttttgac       360
ctggtgaaag cctgtaaaga ggcttgcgcg cagcgaatg tactgctgaa agtgatcatc        420
gaaaccggcg aactgaaaga cgaagcgctg atccgtaaag cgtctgaaat ctccatcaaa       480
gcgggtgcgg acttcatcaa aacctctacc ggtaaagtgg ctgtgaacgc gacgccggaa       540
agcgcgcgca tcatgatgga agtgatccgt gatatgggcg tagaaaaaac cgttggtttc       600
aaaccggcgg gcggcgtgcg tactgcggaa gatgcgcaga aatatctcgc cattgcagat       660
gaactgttcg gtgctgactg ggcagatgcg cgtcactacc gctttggcgc tgatagcctg       720
ctggcaagcc tgctgaaagc gctgggtcac ggcgacggta agagcgccag cagctactaa       780

<210> SEQ ID NO 4
<211> LENGTH: 259
<212> TYPE: PRT
<213> ORGANISM: Artificial Sequence
<220> FEATURE:
<223> OTHER INFORMATION: Synthetically generated peptide
```

<400> SEQUENCE: 4

```
Met Thr Asp Leu Lys Ala Ser Ser Leu Arg Ala Leu Lys Leu Met Asp
 1               5                  10                  15
Leu Thr Thr Leu Asn Asp Asp Thr Asp Glu Lys Val Ile Ala Leu
             20                  25                  30
Cys His Gln Ala Lys Thr Pro Val Gly Asn Thr Ala Ala Ile Cys Ile
             35                  40                  45
Tyr Pro Arg Phe Ile Pro Ile Ala Arg Lys Thr Leu Lys Glu Gln Gly
 50                  55                  60
Thr Pro Glu Ile Arg Ile Ala Thr Val Thr Asn Phe Pro His Gly Asn
 65                  70                  75                  80
Asp Asp Ile Asp Ile Ala Leu Ala Glu Thr Arg Ala Ala Ile Ala Tyr
                 85                  90                  95
Gly Ala Asp Glu Val Asp Val Val Phe Pro Tyr Arg Ala Leu Met Ala
                 100                 105                 110
Gly Asn Glu Gln Val Gly Phe Asp Leu Val Lys Ala Cys Lys Glu Ala
             115                 120                 125
Cys Ala Ala Ala Asn Val Leu Leu Lys Val Ile Glu Thr Gly Glu
130                 135                 140
Leu Lys Asp Glu Ala Leu Ile Arg Lys Ala Ser Glu Ile Ser Ile Lys
145                 150                 155                 160
Ala Gly Ala Asp Phe Ile Lys Thr Ser Thr Gly Lys Val Ala Val Asn
                 165                 170                 175
Ala Thr Pro Glu Ser Ala Arg Ile Met Met Glu Val Ile Arg Asp Met
             180                 185                 190
Gly Val Glu Lys Thr Val Gly Phe Lys Pro Ala Gly Gly Val Arg Thr
             195                 200                 205
Ala Glu Asp Ala Gln Lys Tyr Leu Ala Ile Ala Asp Glu Leu Phe Gly
210                 215                 220
Ala Asp Trp Ala Asp Ala Arg His Tyr Arg Phe Gly Ala Asp Ser Leu
225                 230                 235                 240
Leu Ala Ser Leu Leu Lys Ala Leu Gly His Gly Asp Gly Lys Ser Ala
                 245                 250                 255
Ser Ser Tyr
```

<210> SEQ ID NO 5
<211> LENGTH: 695
<212> TYPE: DNA
<213> ORGANISM: Archaea

<400> SEQUENCE: 5

```
atgaggtttg agtatcgtct cctctccccc gaggaactcg caaagaggat agactatgct     60
attcttcgcg acccaacacc acatagagtc gtagaggctg tagaagaggc ggagaaacta    120
ggcctgagag cagtaacagt gttccacacc atgttgacat ggcttgaggg tgtatcgcgt    180
agagtattga tatccgttgt gatagacttc ccgagcgggg cgagtcacat cgagccaaag    240
gtaaaggctg ttgagcaggc aatagcgcat ggcgctggtg aggttgagtt cgtggttaat    300
gtgtggcagt ggatgaaagg caacagagac tatgttataa cgaggtgcg cgctctctca     360
aggatagcta gagaggtagg agtgaagagc aaggcgataa tcgagtcctc gcttctagac    420
ttatcaacac tccaggagat actggaggca atagcggctc tggataagga ggatagacca    480
gactatgtca gatgaacac agggtggttc tctaggggtg tcgagccgct ggaagtcgct    540
cttgcagcca agatagtcaa gccgcgaggc atgatgatta aagcgtctgg cggcataaaa    600
```

```
gacgggtttt acgcatccct acttgtagct ctaggagcgg acgtgatagg cacgagcaat    660
ccttcaaagc taatccggga tctacaagag gctaa                              695
```

<210> SEQ ID NO 6
<211> LENGTH: 231
<212> TYPE: PRT
<213> ORGANISM: Archaea

<400> SEQUENCE: 6

```
Met Arg Phe Glu Tyr Arg Leu Leu Ser Pro Glu Glu Leu Ala Lys Arg
1               5                   10                  15
Ile Asp Tyr Ala Ile Leu Arg Asp Pro Thr Pro His Arg Val Val Glu
            20                  25                  30
Ala Val Glu Glu Ala Glu Lys Leu Gly Leu Arg Ala Val Thr Val Phe
        35                  40                  45
His Thr Met Leu Thr Trp Leu Glu Gly Val Ser Arg Arg Val Leu Ile
    50                  55                  60
Ser Val Val Ile Asp Phe Pro Ser Gly Ala Ser His Ile Glu Pro Lys
65                  70                  75                  80
Val Lys Ala Val Glu Gln Ala Ile Ala His Gly Ala Gly Glu Val Glu
                85                  90                  95
Phe Val Val Asn Val Trp Gln Trp Met Lys Gly Asn Arg Asp Tyr Val
            100                 105                 110
Ile Asn Glu Val Arg Ala Leu Ser Arg Ile Ala Arg Glu Val Gly Val
        115                 120                 125
Lys Ser Lys Ala Ile Ile Glu Ser Ser Leu Leu Asp Leu Ser Thr Leu
    130                 135                 140
Gln Glu Ile Leu Glu Ala Ile Ala Ala Leu Asp Lys Gly Asp Arg Pro
145                 150                 155                 160
Asp Tyr Val Lys Met Asn Thr Gly Trp Phe Ser Arg Gly Val Glu Pro
                165                 170                 175
Leu Glu Val Ala Leu Ala Ala Lys Ile Val Lys Pro Arg Gly Met Met
            180                 185                 190
Ile Lys Ala Ser Gly Gly Ile Lys Asp Gly Phe Tyr Ala Ser Leu Leu
        195                 200                 205
Val Ala Leu Gly Ala Asp Val Ile Gly Thr Ser Asn Pro Ser Lys Leu
    210                 215                 220
Ile Arg Asp Leu Gln Glu Ala
225                 230
```

<210> SEQ ID NO 7
<211> LENGTH: 660
<212> TYPE: DNA
<213> ORGANISM: Aquifex aeolicus

<400> SEQUENCE: 7

```
atgattgatg taaggaagta catagacaac gcagccctga acctcacct ctctgaaaaa    60 gaaatcgaag aattcgtcct aaagtctgaa gaactcggga tttacgctgt gtgtgtaaac   120
ccgtaccatg tgaagctcgc aagttcaata gcaaagaaag taaagtctg ctgtgtgata    180 ggctttcctt taggacttaa caaaacttcc gttaaagtaa agaagcggt agaagccgta    240 agagacggtg cacaggaact cgatatcgtg tggaaccttt cggctttcaa aagcgagaag   300
tacgatttcg tggtggaaga attaaaggaa attttaggg aaactccttc agcagttcac    360
aaggtaatcg ttgagacacc ttacttaaac gaggaagaaa taaagaaagc ggtggaaatc   420
```

```
tgtattgaag caggagcgga ctttataaag acctcaacgg gctttgcacc gaggggaaca        480
acactcgaag aggtaagact gattaaaagt agcgcgaaag gcaggattaa ggtaaaagct        540
tcgggaggga taagggattt ggaaacggca atatctatga tagaggcggg ggcggacagg        600
ataggcacga gcagcggtat aagcatagcc gaagaatttt taaaacgaca tttgatataa        660
```

<210> SEQ ID NO 8
<211> LENGTH: 219
<212> TYPE: PRT
<213> ORGANISM: Aquifex aeolicus

<400> SEQUENCE: 8

```
Met Ile Asp Val Arg Lys Tyr Ile Asp Asn Ala Ala Leu Lys Pro His
  1               5                  10                  15

Leu Ser Glu Lys Glu Ile Glu Glu Phe Val Leu Lys Ser Glu Glu Leu
             20                  25                  30

Gly Ile Tyr Ala Val Cys Val Asn Pro Tyr His Val Lys Leu Ala Ser
         35                  40                  45

Ser Ile Ala Lys Lys Val Lys Val Cys Cys Val Ile Gly Phe Pro Leu
     50                  55                  60

Gly Leu Asn Lys Thr Ser Val Lys Val Lys Glu Ala Val Glu Ala Val
 65                  70                  75                  80

Arg Asp Gly Ala Gln Glu Leu Asp Ile Val Trp Asn Leu Ser Ala Phe
                 85                  90                  95

Lys Ser Glu Lys Tyr Asp Phe Val Val Glu Glu Leu Lys Glu Ile Phe
            100                 105                 110

Arg Glu Thr Pro Ser Ala Val His Lys Val Ile Val Glu Thr Pro Tyr
        115                 120                 125

Leu Asn Glu Glu Glu Ile Lys Lys Ala Val Glu Ile Cys Ile Glu Ala
    130                 135                 140

Gly Ala Asp Phe Ile Lys Thr Ser Thr Gly Phe Ala Pro Arg Gly Thr
145                 150                 155                 160

Thr Leu Glu Glu Val Arg Leu Ile Lys Ser Ser Ala Lys Gly Arg Ile
                165                 170                 175

Lys Val Lys Ala Ser Gly Gly Ile Arg Asp Leu Glu Thr Ala Ile Ser
            180                 185                 190

Met Ile Glu Ala Gly Ala Asp Arg Ile Gly Thr Ser Ser Gly Ile Ser
        195                 200                 205

Ile Ala Glu Glu Phe Leu Lys Arg His Leu Ile
    210                 215
```

<210> SEQ ID NO 9
<211> LENGTH: 660
<212> TYPE: DNA
<213> ORGANISM: Unknown
<220> FEATURE:
<223> OTHER INFORMATION: Obtained from an environmental sample.

<400> SEQUENCE: 9

```
atgaataata tcgcatcata cattgatcac acaattcttg ctgctactgc aacaagtgat         60
aaagtaaaac agatttgtaa agaagcaaaa gaatatcatt ttgcatctgt atgtattaat        120
agttgtcatg ttggagattg cgcagaaatg ttgaaagatt ctgatgtaag tgtatgtact        180
gtagttggtt ttccactagg tgctatgagc acaaaagcaa aagcatttga agctaaacaa        240
gccgtagatg atggtgccga tgaagttgat atggtaatta atatcggatg gatgaaagac        300
ggtaatgatg aaaaagtatt gaatgatatt aaagaagtaa gaaaagcctg taatggtaaa        360
```

```
ttgttaaagg taatcattga agcttgctta ttaactgatg atgaaaaggt taaagcatgt      420
agtctagcag ttaaagctgg tgctgacttt gttaaaacat ctacagggtt ttctactggc      480
ggtgcaaagg aagttgatat tgcattaatg agaaagactg ttggttctga aattggtgtt      540
aaagctgctg gtggtattca tacatatgaa gaatctcttg gaatggtaga aaatggtgca      600
acacgtattg gtgcaagtgc tggtattgca attgttaaag gcgaagcagc acataaataa      660
```

```
<210> SEQ ID NO 10
<211> LENGTH: 219
<212> TYPE: PRT
<213> ORGANISM: Unknown
<220> FEATURE:
<223> OTHER INFORMATION: Obtained from an environmental sample.

<400> SEQUENCE: 10
```

Met Asn Asn Ile Ala Ser Tyr Ile Asp His Thr Ile Leu Ala Ala Thr
1               5                   10                  15

Ala Thr Ser Asp Lys Val Lys Gln Ile Cys Lys Glu Ala Lys Glu Tyr
            20                  25                  30

His Phe Ala Ser Val Cys Ile Asn Ser Cys His Val Gly Asp Cys Ala
        35                  40                  45

Glu Met Leu Lys Asp Ser Asp Val Ser Val Cys Thr Val Val Gly Phe
    50                  55                  60

Pro Leu Gly Ala Met Ser Thr Lys Ala Lys Ala Phe Glu Ala Lys Gln
65                  70                  75                  80

Ala Val Asp Asp Gly Ala Asp Glu Val Asp Met Val Ile Asn Ile Gly
                85                  90                  95

Trp Met Lys Asp Gly Asn Asp Glu Lys Val Leu Asn Asp Ile Lys Glu
            100                 105                 110

Val Arg Lys Ala Cys Asn Gly Lys Leu Leu Lys Val Ile Ile Glu Ala
        115                 120                 125

Cys Leu Leu Thr Asp Asp Glu Val Lys Ala Cys Ser Leu Ala Val
    130                 135                 140

Lys Ala Gly Ala Asp Phe Val Lys Thr Ser Thr Gly Phe Ser Thr Gly
145                 150                 155                 160

Gly Ala Lys Glu Val Asp Ile Ala Leu Met Arg Lys Thr Val Gly Ser
                165                 170                 175

Glu Ile Gly Val Lys Ala Ala Gly Gly Ile His Thr Tyr Glu Ser
            180                 185                 190

Leu Gly Met Val Glu Asn Gly Ala Thr Arg Ile Gly Ala Ser Ala Gly
        195                 200                 205

Ile Ala Ile Val Lys Gly Glu Ala Ala His Lys
    210                 215

```
<210> SEQ ID NO 11
<211> LENGTH: 663
<212> TYPE: DNA
<213> ORGANISM: Unknown
<220> FEATURE:
<223> OTHER INFORMATION: Obtained from an environmental sample.

<400> SEQUENCE: 11
atgcaaatta ataaatatat tgaccatact attctcaagg cagacgctcc aaaatctaaa       60
gttcaacaaa tcatcgatga agcaaaaaaa tatgatttca tgagtgtttg tatcaacccg      120
acttgggtaa attatgccag tcaagaactc aaagactctg atgtaaaagt atgtacagtt      180
attggcttcc ctttaggtgc taatacttct gaactcaaag catttgaagc taaaaacgcc      240
```

```
attgaaaatg gggctgacga aattgacatg gtcattaata ttggtgcagc caaatctaag    300
gattgggatc ttgttgagtc agatattgca gctgtaaatg ctgtgaaagg cgataaacta    360
ctcaaggtga ttattgaaac gagtcttttg actgatgaag aaaaaattaa agcttgccaa    420
attgctaagg ccgttggtgc tgattttgtc aaaacttcaa caggtttctc aactggagga    480
gcgacagtcc atgatgtaaa attaatgcgt caaactgtag gtccagatat gggagttaaa    540
gcctctggtg gtgttcataa tcttgaagaa gcaaaagcaa tgattgatgc tggagcaact    600
cgtcttggag tttctgctgg tgtcgcaatt atggaaggtc ttacctcaaa tgacagctac    660
taa                                                                   663
```

<210> SEQ ID NO 12
<211> LENGTH: 220
<212> TYPE: PRT
<213> ORGANISM: Unknown
<220> FEATURE:
<223> OTHER INFORMATION: Obtained from an environmental sample.

<400> SEQUENCE: 12

```
Met Gln Ile Asn Lys Tyr Ile Asp His Thr Ile Leu Lys Ala Asp Ala
 1               5                  10                  15

Pro Lys Ser Lys Val Gln Gln Ile Ile Asp Glu Ala Lys Lys Tyr Asp
            20                  25                  30

Phe Met Ser Val Cys Ile Asn Pro Thr Trp Val Asn Tyr Ala Ser Gln
        35                  40                  45

Glu Leu Lys Asp Ser Asp Val Lys Val Cys Thr Val Ile Gly Phe Pro
    50                  55                  60

Leu Gly Ala Asn Thr Ser Glu Leu Lys Ala Phe Glu Ala Lys Asn Ala
65                  70                  75                  80

Ile Glu Asn Gly Ala Asp Glu Ile Asp Met Val Ile Asn Ile Gly Ala
                85                  90                  95

Ala Lys Ser Lys Asp Trp Asp Leu Val Glu Ser Asp Ile Ala Ala Val
            100                 105                 110

Asn Ala Val Lys Gly Asp Lys Leu Leu Lys Val Ile Ile Glu Thr Ser
        115                 120                 125

Leu Leu Thr Asp Glu Glu Lys Ile Lys Ala Cys Gln Ile Ala Lys Ala
    130                 135                 140

Val Gly Ala Asp Phe Val Lys Thr Ser Thr Gly Phe Ser Thr Gly Gly
145                 150                 155                 160

Ala Thr Val His Asp Val Lys Leu Met Arg Gln Thr Val Gly Pro Asp
                165                 170                 175

Met Gly Val Lys Ala Ser Gly Gly Val His Asn Leu Glu Glu Ala Lys
            180                 185                 190

Ala Met Ile Asp Ala Gly Ala Thr Arg Leu Gly Val Ser Ala Gly Val
        195                 200                 205

Ala Ile Met Glu Gly Leu Thr Ser Asn Asp Ser Tyr
    210                 215                 220
```

<210> SEQ ID NO 13
<211> LENGTH: 666
<212> TYPE: DNA
<213> ORGANISM: Unknown
<220> FEATURE:
<223> OTHER INFORMATION: Obtained from an environmental sample.

<400> SEQUENCE: 13

```
atgaatatcg cgaaaatgat cgatcatacg ctgctcaaac cggaagcgac agaacaacaa    60
```

```
atcgtgcaac tgtgcacgga agcaaagcaa tacggctttg ctgccgtgtg cgtcaaccca    120
acgtgggtga aaacggcggc gcgcgagctt tccggcacgg atgtccgcgt ctgcacggtc    180
atcggctttc cacttggggc aacgacgccg gaaacaaagg cgtttgaaac aacgaacgcc    240
atcgaaaacg gcgctcgcga agtcgacatg gtgatcaaca tcggcgcgtt aaaaagcggg    300
caagacgagc ttgtcgagcg cgacattcgt gcggttgtcg aagcggcggc tggcagggcg    360
cttgtcaaag tgatcgttga aacggcgctt ttgaccgatg aggaaaaagt gcgcgcctgc    420
cagctcgcag tgaaagccgg cgctgattat gtgaaaacgt cgaccgggtt ttccggcgga    480
ggtgcgacgg tggaggatgt ggcgctgatg cggaaaacgg tcggcgacag agcaggcgtc    540
aaagcatcag gcggcgtccg tgactggaaa accgctgagg cgatgatcaa cgccggcgcg    600
acgcgcatcg gcacaagctc tggggtggcg atcgtcaccg gcgggacggg ccgcgctgac    660
tactaa                                                               666
```

<210> SEQ ID NO 14
<211> LENGTH: 221
<212> TYPE: PRT
<213> ORGANISM: Unknown
<220> FEATURE:
<223> OTHER INFORMATION: Obtained from an environmental sample.

<400> SEQUENCE: 14

```
Met Asn Ile Ala Lys Met Ile Asp His Thr Leu Leu Lys Pro Glu Ala
 1               5                  10                  15

Thr Glu Gln Gln Ile Val Gln Leu Cys Thr Glu Ala Lys Gln Tyr Gly
            20                  25                  30

Phe Ala Ala Val Cys Val Asn Pro Thr Trp Val Lys Thr Ala Ala Arg
        35                  40                  45

Glu Leu Ser Gly Thr Asp Val Arg Val Cys Thr Val Ile Gly Phe Pro
    50                  55                  60

Leu Gly Ala Thr Thr Pro Glu Thr Lys Ala Phe Glu Thr Thr Asn Ala
65                  70                  75                  80

Ile Glu Asn Gly Ala Arg Glu Val Asp Met Val Ile Asn Ile Gly Ala
                85                  90                  95

Leu Lys Ser Gly Gln Asp Glu Leu Val Glu Arg Asp Ile Arg Ala Val
            100                 105                 110

Val Glu Ala Ala Ala Gly Arg Ala Leu Val Lys Val Ile Val Glu Thr
        115                 120                 125

Ala Leu Leu Thr Asp Glu Glu Lys Val Arg Ala Cys Gln Leu Ala Val
    130                 135                 140

Lys Ala Gly Ala Asp Tyr Val Lys Thr Ser Thr Gly Phe Ser Gly Gly
145                 150                 155                 160

Gly Ala Thr Val Glu Asp Val Ala Leu Met Arg Lys Thr Val Gly Asp
                165                 170                 175

Arg Ala Gly Val Lys Ala Ser Gly Gly Val Arg Asp Trp Lys Thr Ala
            180                 185                 190

Glu Ala Met Ile Asn Ala Gly Ala Thr Arg Ile Gly Thr Ser Ser Gly
        195                 200                 205

Val Ala Ile Val Thr Gly Gly Thr Gly Arg Ala Asp Tyr
    210                 215                 220
```

<210> SEQ ID NO 15
<211> LENGTH: 672
<212> TYPE: DNA
<213> ORGANISM: Unknown
<220> FEATURE:

<223> OTHER INFORMATION: Obtained from an environmental sample.

<400> SEQUENCE: 15

```
atgaacattg caaagttaat tgatcataca gttttgaaac cggatactaa aaaagaagac    60
gttatgaaag ttttagaaga agcaaaaaaa tacaatttcg cttctgtttg tattaatcct   120
acatgggtga aattagcagc cgaagaatta gcaggacatg atgtagatgt ttgtacagtt   180
attggtttcc ctttaggtgc gaatacaact gaaacaaaag tatttgaaac aaaagatgta   240
attgcaaaag gtgcaactga agttgacatg gtaatcaacg ttggcgcttt aaaagatggc   300
gataatgaat tcgttgaaaa agatatttac gaagttgtac aagctgcaaa aggaaaagca   360
cttgtaaaag ttattattga acatgctta ttaacagatg aagaaaaagt acgtgcttgt   420
gaattatctg taaaagctgg agctgacttt gtaaaaactt caactggatt ctcaactggt   480
ggagcgactg ctgaagatat cgcattaatg cgtaaaactg ttggagaaaa tgttggtgtg   540
aaagcatctg gtggtgttcg tacaagagaa gatgcagaga aaatgattga agcgggagct   600
tctagaatcg gagcaagcgc tagtgttgca atcgtattag atgacaaaaa tggtgcttca   660
gataactact aa                                                       672
```

<210> SEQ ID NO 16
<211> LENGTH: 223
<212> TYPE: PRT
<213> ORGANISM: Unknown
<220> FEATURE:
<223> OTHER INFORMATION: Obtained from an environmental sample.

<400> SEQUENCE: 16

Met Asn Ile Ala Lys Leu Ile Asp His Thr Val Leu Lys Pro Asp Thr
1               5                   10                  15

Lys Lys Glu Asp Val Met Lys Val Leu Glu Glu Ala Lys Lys Tyr Asn
            20                  25                  30

Phe Ala Ser Val Cys Ile Asn Pro Thr Trp Val Lys Leu Ala Ala Glu
        35                  40                  45

Glu Leu Ala Gly His Asp Val Asp Val Cys Thr Val Ile Gly Phe Pro
    50                  55                  60

Leu Gly Ala Asn Thr Thr Glu Thr Lys Val Phe Glu Thr Lys Asp Val
65                  70                  75                  80

Ile Ala Lys Gly Ala Thr Glu Val Asp Met Val Ile Asn Val Gly Ala
                85                  90                  95

Leu Lys Asp Gly Asp Asn Glu Phe Val Glu Lys Asp Ile Tyr Glu Val
            100                 105                 110

Val Gln Ala Ala Lys Gly Lys Ala Leu Val Lys Val Ile Ile Glu Thr
        115                 120                 125

Cys Leu Leu Thr Asp Glu Glu Lys Val Arg Ala Cys Glu Leu Ser Val
    130                 135                 140

Lys Ala Gly Ala Asp Phe Val Lys Thr Ser Thr Gly Phe Ser Thr Gly
145                 150                 155                 160

Gly Ala Thr Ala Glu Asp Ile Ala Leu Met Arg Lys Thr Val Gly Glu
                165                 170                 175

Asn Val Gly Val Lys Ala Ser Gly Gly Val Arg Thr Arg Glu Asp Ala
            180                 185                 190

Glu Lys Met Ile Glu Ala Gly Ala Ser Arg Ile Gly Ala Ser Ala Ser
        195                 200                 205

Val Ala Ile Val Leu Asp Asp Lys Asn Gly Ala Ser Asp Asn Tyr
    210                 215                 220

<210> SEQ ID NO 17
<211> LENGTH: 753
<212> TYPE: DNA
<213> ORGANISM: Unknown
<220> FEATURE:
<223> OTHER INFORMATION: Obtained from an environmental sample.

<400> SEQUENCE: 17

| | | | | | |
|---|---|---|---|---|---|
| atgcaccgaa | tagtcgacgc | aggtgccgct | cgcataggtt | tgatactggg | ccaaacggct | 60 |
| tcagctcgag | actgggccag | ccttgtcgat | cacacgcttt | taaaacctga | agcaaccgac | 120 |
| gacgatatta | aaaagctttg | tcaggaagct | gccacttatc | gctttgcttc | ggtttgtgta | 180 |
| aacccgacat | gggtgcgcgt | cgcggcgtgc | agtctacagg | gaagcggagt | tcctgtttgt | 240 |
| actgtaatcg | ggtttccgct | tggcgcaact | ctggctgatg | tcaaagccta | cgaagcgcgg | 300 |
| cgggcaatct | tcgatggtgc | taaagaagtt | gacatggtga | tcaatgttgg | cgcgttgaag | 360 |
| agcggtgacg | attgtttggt | tgagcatgac | attcgtgcgg | ttgctgaagt | tgctcacgag | 420 |
| tacaacgcga | tttgtaaagt | catcatcgag | acggcactct | taactgatga | agagaaagtt | 480 |
| agagcctgta | tcgcagcgaa | gaaagctgga | gcagacttcg | tcaaaacttc | aaccggtttt | 540 |
| tcgaagggcg | gcgcaactgt | cgctgatgtt | gcgttgatgc | gtaagacagt | tggttctgag | 600 |
| ttaggtgtga | aagcatcggg | tggtgttaaa | ggacttgaag | atgctcgtaa | gatggttgaa | 660 |
| gcaggtgcga | cgagaattgg | cgcgagtgtt | ggtgtgaaga | tcgcgcagga | agcagcaggg | 720 |
| aagactccgg | cacaatctgc | agcaagtgcg | tat | | | 753 |

<210> SEQ ID NO 18
<211> LENGTH: 251
<212> TYPE: PRT
<213> ORGANISM: Unknown
<220> FEATURE:
<223> OTHER INFORMATION: Obtained from an environmental sample.
<220> FEATURE:
<221> NAME/KEY: SIGNAL
<222> LOCATION: (1)...(22)

<400> SEQUENCE: 18

Met His Arg Ile Val Asp Ala Gly Ala Ala Arg Ile Gly Leu Ile Leu
1               5                   10                  15

Gly Gln Thr Ala Ser Ala Arg Asp Trp Ala Ser Leu Val Asp His Thr
            20                  25                  30

Leu Leu Lys Pro Glu Ala Thr Asp Asp Ile Lys Lys Leu Cys Gln
        35                  40                  45

Glu Ala Ala Thr Tyr Arg Phe Ala Ser Val Cys Val Asn Pro Thr Trp
    50                  55                  60

Val Arg Val Ala Ala Cys Ser Leu Gln Gly Ser Gly Val Pro Val Cys
65                  70                  75                  80

Thr Val Ile Gly Phe Pro Leu Gly Ala Thr Leu Ala Asp Val Lys Ala
                85                  90                  95

Tyr Glu Ala Arg Arg Ala Ile Phe Asp Gly Lys Glu Val Asp Met
            100                 105                 110

Val Ile Asn Val Gly Ala Leu Lys Ser Gly Asp Cys Leu Val Glu
        115                 120                 125

His Asp Ile Arg Ala Val Ala Glu Val Ala His Glu Tyr Asn Ala Ile
    130                 135                 140

Cys Lys Val Ile Ile Glu Thr Ala Leu Leu Thr Asp Glu Glu Lys Val
145                 150                 155                 160

Arg Ala Cys Ile Ala Ala Lys Lys Ala Gly Ala Asp Phe Val Lys Thr

| | | | | | | | 165 | | | 170 | | | 175 | | |
|---|---|---|---|---|---|---|---|---|---|---|---|---|---|---|---|

Ser Thr Gly Phe Ser Lys Gly Gly Ala Thr Val Ala Asp Val Ala Leu
            180                    185                  190

Met Arg Lys Thr Val Gly Ser Glu Leu Gly Val Lys Ala Ser Gly Gly
        195                    200                  205

Val Lys Gly Leu Glu Asp Ala Arg Lys Met Val Glu Ala Gly Ala Thr
   210                    215                  220

Arg Ile Gly Ala Ser Val Gly Val Lys Ile Ala Gln Glu Ala Ala Gly
225                  230                  235                  240

Lys Thr Pro Ala Gln Ser Ala Ala Ser Ala Tyr
            245                    250

<210> SEQ ID NO 19
<211> LENGTH: 756
<212> TYPE: DNA
<213> ORGANISM: Unknown
<220> FEATURE:
<223> OTHER INFORMATION: Obtained from an environmental sample.

<400> SEQUENCE: 19

```
atggcttcga tttcccccaa tccagccgct gaactcgagt ttgacaacgg ttcctgggac      60
gccgcggcct tcgccgcgca cgcgctctcc agttggcagc acctggccgc cgtcatcgac     120
cacaccctgc tcaagcccga ggctactcac gcccaggtca gcggcctgtg caaggaggcc     180
atccgctacc gcttcgcctg cgtcatggtc aaccccgtct gggtggccaa cgtggccgcg     240
caactggccg gctccggcat cccggtcggc gtggtcatcg gcttcccgct gggcgcatcg     300
ctggtctcca cgctccgcca ggaggctgcg gcgctctgcc gcctgggtgc gcgcgagttg     360
gacatggtgc tacccgtcgg cgtgctcaag agccaccact accatgccgt ctcgcacacc     420
atccgctctg ccgccacggt ggcccaccac cacggcgccc tcctcaaagt catcctcgaa     480
acctgcctgc tcaccgtcga agaaaagctg cgcgcctcgg agatcgccat ccaggccggc     540
gcggacttcc tcaagacctc caccggcttc tccacctccg gcgcaaccgt ggccgatgtg     600
gccctgttgc gcggcgtggc cggcgcgcgc gccggcgtca aggcctctgg cggcatccgc     660
accctggccg acgtcagggc catgctcgaa gccgcgccaa ccgtgtcgg cgcctcggct     720
tcggtctcca tcctgcggga gttgggcgct gagtaa                              756
```

<210> SEQ ID NO 20
<211> LENGTH: 251
<212> TYPE: PRT
<213> ORGANISM: Unknown
<220> FEATURE:
<223> OTHER INFORMATION: Obtained from an environmental sample.

<400> SEQUENCE: 20

Met Ala Ser Ile Ser Pro Asn Pro Ala Ala Glu Leu Glu Phe Asp Asn
1                 5                    10                  15

Gly Ser Trp Asp Ala Ala Ala Phe Ala Ala His Ala Leu Ser Ser Trp
              20                    25                  30

Gln His Leu Ala Ala Val Ile Asp His Thr Leu Leu Lys Pro Glu Ala
          35                    40                  45

Thr His Ala Gln Val Ser Gly Leu Cys Lys Glu Ala Ile Arg Tyr Arg
   50                    55                  60

Phe Ala Cys Val Met Val Asn Pro Val Trp Val Ala Asn Val Ala Ala
65                  70                  75                  80

Gln Leu Ala Gly Ser Gly Ile Pro Val Gly Val Val Ile Gly Phe Pro
              85                    90                  95

```
Leu Gly Ala Ser Leu Val Ser Thr Leu Arg Gln Glu Ala Ala Leu
            100                 105                 110
Cys Arg Leu Gly Ala Arg Glu Leu Asp Met Val Leu Pro Val Gly Val
        115                 120                 125
Leu Lys Ser His His Tyr His Ala Val Ser His Thr Ile Arg Ser Ala
    130                 135                 140
Ala Thr Val Ala His His Gly Ala Leu Leu Lys Val Ile Leu Glu
145                 150                 155                 160
Thr Cys Leu Leu Thr Val Glu Glu Lys Leu Arg Ala Ser Glu Ile Ala
                165                 170                 175
Ile Gln Ala Gly Ala Asp Phe Leu Lys Thr Ser Thr Gly Phe Ser Thr
            180                 185                 190
Ser Gly Ala Thr Val Ala Asp Val Ala Leu Leu Arg Gly Val Ala Gly
        195                 200                 205
Ala Arg Ala Gly Val Lys Ala Ser Gly Gly Ile Arg Thr Leu Ala Asp
    210                 215                 220
Val Arg Ala Met Leu Glu Ala Gly Ala Ser Arg Val Gly Ala Ser Ala
225                 230                 235                 240
Ser Val Ser Ile Leu Arg Glu Leu Gly Ala Glu
                245                 250
```

<210> SEQ ID NO 21
<211> LENGTH: 675
<212> TYPE: DNA
<213> ORGANISM: Bacteria

<400> SEQUENCE: 21

```
atgacgcgtt cgattgcaca aatgattgat catacgctac ttaaaccaaa tacaacagaa    60
gaccaaattg taaagctctg tgaggaagca aggaatact catttgcatc tgtttgtgtg    120
aatcctactt gggtcgctct tgctgcgcag ttgctaaaag atgcacctga tgtgaaagta    180
tgtacagtta tcggctttcc gttaggggca acgactccgg aagtgaaagc gtttgaaacg    240
actaatgcca ttgaaaatgg agcgacagaa gtggacatgg tcattaacat tggagcgtta    300
aaagataaac aatacgagct tgttggacgc gacattcaag cggttgttaa agcagcagaa    360
gggaaagcat taacgaaagt aatcattgaa acatcgttat aacggagga agagaagaag    420
gctgcgtgtg agcttgccgt aaaagcagga gccgactttg tcaaaacgtc gactggattc    480
tctggcggag tgctacggc tgaggatatc gcgctcatgc gaaaagtggt cggaccaaat    540
ttaggagtca aagcttctgg aggtgttaga gatctgtccg acgcgaaagc gatgattgat    600
gctggtgcta ctcggattgg tgcgagtgct ggggtggcga ttgttaacgg ggagcgtagc    660
gaagggagtt attaa                                                    675
```

<210> SEQ ID NO 22
<211> LENGTH: 224
<212> TYPE: PRT
<213> ORGANISM: Bacteria

<400> SEQUENCE: 22

```
Met Thr Arg Ser Ile Ala Gln Met Ile Asp His Thr Leu Leu Lys Pro
  1               5                  10                  15
Asn Thr Thr Glu Asp Gln Ile Val Lys Leu Cys Glu Glu Ala Lys Glu
                 20                  25                  30
Tyr Ser Phe Ala Ser Val Cys Val Asn Pro Thr Trp Val Ala Leu Ala
             35                  40                  45
```

```
Ala Gln Leu Leu Lys Asp Ala Pro Asp Val Lys Val Cys Thr Val Ile
    50                  55                  60
Gly Phe Pro Leu Gly Ala Thr Thr Pro Glu Val Lys Ala Phe Glu Thr
 65                  70                  75                  80
Thr Asn Ala Ile Glu Asn Gly Ala Thr Glu Val Asp Met Val Ile Asn
                 85                  90                  95
Ile Gly Ala Leu Lys Asp Lys Gln Tyr Glu Leu Val Gly Arg Asp Ile
                100                 105                 110
Gln Ala Val Val Lys Ala Ala Glu Gly Lys Ala Leu Thr Lys Val Ile
            115                 120                 125
Ile Glu Thr Ser Leu Leu Thr Glu Glu Lys Lys Ala Ala Cys Glu
    130                 135                 140
Leu Ala Val Lys Ala Gly Ala Asp Phe Val Lys Thr Ser Thr Gly Phe
145                 150                 155                 160
Ser Gly Gly Gly Ala Thr Ala Glu Asp Ile Ala Leu Met Arg Lys Val
                165                 170                 175
Val Gly Pro Asn Leu Gly Val Lys Ala Ser Gly Val Arg Asp Leu
                180                 185                 190
Ser Asp Ala Lys Ala Met Ile Asp Ala Gly Ala Thr Arg Ile Gly Ala
            195                 200                 205
Ser Ala Gly Val Ala Ile Val Asn Gly Glu Arg Ser Glu Gly Ser Tyr
    210                 215                 220
```

<210> SEQ ID NO 23
<211> LENGTH: 779
<212> TYPE: DNA
<213> ORGANISM: Salmonella typhimurium

<400> SEQUENCE: 23

```
atgccgttgg agaatgtcat gactgattta aaagcaagca gcctgcgtgc gctcaaactg      60
atggatctga ccactctgaa cgatgacgac accaatgaaa aagtgatcgc gttgtgtcat     120
caggcaaaaa ctccggtcgg gaatacggcg gcgatttgta tttacccgcg ttttatcccg     180
attgcgcgta aaactctgaa agaacaaggt acgccggaca tccgcattgc aacggtgact     240
aacttcccgc atggcaatga tgacatcgat attgcgctgg cggaaacccg tgcggcgatc     300
gcctacggcg ctgacgaagt ggacgtggta ttcccgtacc gcgcgttgat cgccggtaac     360
gagcaggtgg gttttgacct ggtaaaagcc tgtaaagacg cttgtgccgc agcgaacgta     420
ttgctgaaag tgattatcga accggcgag ctgaaagaag aggcgctgat tcgtaaagcc     480
tctgaaatct ccattaaagc cggtgcggat ttcatcaaaa cctctaccgg taaagtgccg     540
gtaaacgcta cgccggaaag cgcgcgcatc atgatggaag tgatccgcga catgggcgtt     600
tccaaaaccg ttggcttcaa accggcgggc ggcgtacgta cggcggaaga cgcgcagaaa     660
ttcctcgcga ttgcagacga actgtttggc gctgactggg cagattctcg tcactaccgc     720
tttggcgcat ccagcctgct ggcaagcctg ctgaaagcgc tgggtcacgg cgacggtaa      779
```

<210> SEQ ID NO 24
<211> LENGTH: 259
<212> TYPE: PRT
<213> ORGANISM: Salmonella typhimurium

<400> SEQUENCE: 24

```
Met Pro Leu Glu Asn Val Met Thr Asp Leu Lys Ala Ser Ser Leu Arg
 1               5                  10                  15
Ala Leu Lys Leu Met Asp Leu Thr Thr Leu Asn Asp Asp Asp Thr Asn
            20                  25                  30
```

```
Glu Lys Val Ile Ala Leu Cys His Gln Ala Lys Thr Pro Val Gly Asn
             35                  40                  45
Thr Ala Ala Ile Cys Ile Tyr Pro Arg Phe Ile Pro Ile Ala Arg Lys
 50                  55                  60
Thr Leu Lys Glu Gln Gly Thr Pro Asp Ile Arg Ile Ala Thr Val Thr
 65                  70                  75                  80
Asn Phe Pro His Gly Asn Asp Asp Ile Asp Ile Ala Leu Ala Glu Thr
                 85                  90                  95
Arg Ala Ala Ile Ala Tyr Gly Ala Asp Glu Val Asp Val Val Phe Pro
                100                 105                 110
Tyr Arg Ala Leu Ile Ala Gly Asn Glu Gln Val Gly Phe Asp Leu Val
                115                 120                 125
Lys Ala Cys Lys Asp Ala Cys Ala Ala Ala Asn Val Leu Leu Lys Val
130                 135                 140
Ile Ile Glu Thr Gly Glu Leu Lys Glu Glu Ala Leu Ile Arg Lys Ala
145                 150                 155                 160
Ser Glu Ile Ser Ile Lys Ala Gly Ala Asp Phe Ile Lys Thr Ser Thr
                165                 170                 175
Gly Lys Val Pro Val Asn Ala Thr Pro Glu Ser Ala Arg Ile Met Met
                180                 185                 190
Glu Val Ile Arg Asp Met Gly Val Ser Lys Thr Val Gly Phe Lys Pro
                195                 200                 205
Ala Gly Gly Val Arg Thr Ala Glu Asp Ala Gln Lys Phe Leu Ala Ile
                210                 215                 220
Ala Asp Glu Leu Phe Gly Ala Asp Trp Ala Asp Ser Arg His Tyr Arg
225                 230                 235                 240
Phe Gly Ala Ser Ser Leu Leu Ala Ser Leu Leu Lys Ala Leu Gly His
                245                 250                 255
Gly Asp Gly

<210> SEQ ID NO 25
<211> LENGTH: 798
<212> TYPE: DNA
<213> ORGANISM: Artificial Sequence
<220> FEATURE:
<223> OTHER INFORMATION: Synthetically generated oligonucleotide.

<400> SEQUENCE: 25
atgccgttgg agaatgtcat gactgattta aaagcaagca gcctgcgtgc gctcaaactg      60
atggatctga ccactctgaa cgatgacgac accaatgaaa aagtgatcgc gttgtgtcat     120
caggcaaaaa ctccggtcgg aatacggcg gcgatttgta tttacccgcg ttttatcccg      180
attgcgcgta aaactctgaa agaacaaggt acgccggaca tccgcattgc aacggtgact     240
aacttcccgc atggcaatga tgacatcgat attgcgctgg cggaaacccg tgcggcgatc     300
gcctacggcg ctgacgaagt ggacgtggta ttcccgtacc gcgcgttgat cgccggtaac     360
gagcaggtgg gttttgacct ggtaaaagcc tgtaaagacg cttgtgccgc agcgaacgta     420
ttgctgaaag tgattatcga accggcgag ctgaaagaag aggcgctgat cgtaaagcc      480
tctgaaatct ccattaaagc cggtgcggat ttcatcaaaa cctctaccgg taaagtgccg     540
gtaaacgcta cgccggaaag cgcgcgcatc atgatggaag tgatccgcga catgggcgtt     600
tccaaaaccg ttggcttcaa accggcgggc ggcgtacgta cggcggaaga cgcgcagaaa     660
ttcctcgcga ttgcagacga actgtttggc gctgactggg cagattctcg tcactaccgc     720
tttggcgcag atagcctgct ggcaagcctg ctgaaagcgc tgggtcacgg cgacggtaag     780
```
agcgccagca gctactaa 798

<210> SEQ ID NO 26
<211> LENGTH: 265
<212> TYPE: PRT
<213> ORGANISM: Artificial Sequence
<220> FEATURE:
<223> OTHER INFORMATION: Synthetically generated polypeptide.

<400> SEQUENCE: 26

Met Pro Leu Glu Asn Val Met Thr Asp Leu Lys Ala Ser Ser Leu Arg
1               5                   10                  15

Ala Leu Lys Leu Met Asp Leu Thr Thr Leu Asn Asp Asp Thr Asn
            20                  25                  30

Glu Lys Val Ile Ala Leu Cys His Gln Ala Lys Thr Pro Val Gly Asn
        35                  40                  45

Thr Ala Ala Ile Cys Ile Tyr Pro Arg Phe Ile Pro Ile Ala Arg Lys
    50                  55                  60

Thr Leu Lys Glu Gln Gly Thr Pro Asp Ile Arg Ile Ala Thr Val Thr
65                  70                  75                  80

Asn Phe Pro His Gly Asn Asp Asp Ile Asp Ile Ala Leu Ala Glu Thr
                85                  90                  95

Arg Ala Ala Ile Ala Tyr Gly Ala Asp Glu Val Asp Val Val Phe Pro
            100                 105                 110

Tyr Arg Ala Leu Ile Ala Gly Asn Glu Gln Val Gly Phe Asp Leu Val
        115                 120                 125

Lys Ala Cys Lys Asp Ala Cys Ala Ala Ala Asn Val Leu Leu Lys Val
    130                 135                 140

Ile Ile Glu Thr Gly Glu Leu Lys Glu Gly Ala Leu Ile Arg Lys Ala
145                 150                 155                 160

Ser Glu Ile Ser Ile Lys Ala Gly Ala Asp Phe Ile Lys Thr Ser Thr
                165                 170                 175

Gly Lys Val Pro Val Asn Ala Thr Pro Glu Ser Ala Arg Ile Met Met
            180                 185                 190

Glu Val Ile Arg Asp Met Gly Val Ser Lys Thr Val Gly Phe Lys Pro
        195                 200                 205

Ala Gly Gly Val Arg Thr Ala Glu Asp Ala Gln Lys Phe Leu Ala Ile
    210                 215                 220

Ala Asp Glu Leu Phe Gly Ala Asp Trp Ala Asp Ser Arg His Tyr Arg
225                 230                 235                 240

Phe Gly Ala Asp Ser Leu Leu Ala Ser Leu Leu Lys Ala Leu Gly His
                245                 250                 255

Gly Asp Gly Lys Ser Ala Ser Ser Tyr
            260                 265

<210> SEQ ID NO 27
<211> LENGTH: 637
<212> TYPE: DNA
<213> ORGANISM: Bacteria

<400> SEQUENCE: 27
atgagcttag ccaacataat tgatcataca gctttgaaac cgcatacaca aaaagcggac    60
attctaaaac taattgaaga agcgaaaaca tacaaatttg cttcagtatg tgtcaatccg   120
acatgggtgg agcttgctgc aaaagagctt aagggaactg agtcgacgt ttgtacggtc    180 atcggcttcc cgctcggtgc caatacaact gaaacaaaag cgttcgaaac aaaagacgcg   240

```
atttcaaaag gcgccactga agtggatatg gtcattaata ttgccgcttt aaaagacaag      300
gaagacgatg tggtggaagc tgatatccgc ggtgtagtgg aagctgcagc cggaaaagcg      360
cttgtcaaag tcattatcga aacgtgcctt ctgactgatg aagaaaaaga acgtgcatgc      420
cgtttagcgg tgtctgcggg agcggatttc gtaaaaacat caacaggctt ttctacaggc      480
ggcgcaacga aggaagatat cgccttaatg cgcaaaacag taggacctga tatcggcgtg      540
aaagcatctg gcggaatcag aacgaaagaa gatgtagaca caatggttga ggctggtgca      600
agccgaattg gcgccagcgc aggcgtttct atcgtaa                                637
```

```
<210> SEQ ID NO 28
<211> LENGTH: 212
<212> TYPE: PRT
<213> ORGANISM: Bacteria

<400> SEQUENCE: 28
```

```
Met Ser Leu Ala Asn Ile Ile Asp His Thr Ala Leu Lys Pro His Thr
 1               5                  10                  15

Gln Lys Ala Asp Ile Leu Lys Leu Ile Glu Glu Ala Lys Thr Tyr Lys
             20                  25                  30

Phe Ala Ser Val Cys Val Asn Pro Thr Trp Val Glu Leu Ala Ala Lys
         35                  40                  45

Glu Leu Lys Gly Thr Gly Val Asp Val Cys Thr Val Ile Gly Phe Pro
     50                  55                  60

Leu Gly Ala Asn Thr Thr Glu Thr Lys Ala Phe Glu Thr Lys Asp Ala
 65                  70                  75                  80

Ile Ser Lys Gly Ala Thr Glu Val Asp Met Val Ile Asn Ile Ala Ala
             85                  90                  95

Leu Lys Asp Lys Glu Asp Val Val Glu Ala Asp Ile Arg Gly Val
            100                 105                 110

Val Glu Ala Ala Ala Gly Lys Ala Leu Val Lys Val Ile Glu Thr
        115                 120                 125

Cys Leu Leu Thr Asp Glu Glu Lys Glu Arg Ala Cys Arg Leu Ala Val
130                 135                 140

Ser Ala Gly Ala Asp Phe Val Lys Thr Ser Thr Gly Phe Ser Thr Gly
145                 150                 155                 160

Gly Ala Thr Lys Glu Asp Ile Ala Leu Met Arg Lys Thr Val Gly Pro
                165                 170                 175

Asp Ile Gly Val Lys Ala Ser Gly Gly Ile Arg Thr Lys Glu Asp Val
            180                 185                 190

Asp Thr Met Val Glu Ala Gly Ala Ser Arg Ile Gly Ala Ser Ala Gly
        195                 200                 205

Val Ser Ile Val
    210
```

```
<210> SEQ ID NO 29
<211> LENGTH: 774
<212> TYPE: DNA
<213> ORGANISM: Agrobacterium tumefaciens

<400> SEQUENCE: 29
atggaactgc agcgtccgcg cgaagcggct gccctcactt tgtccttgct ggacctgacc       60
aatcttaggg aagactgcac gccgcagcag atcgcaaccc tctgccagcg ggcgcatacg      120
gagtttggca acaccgctgc catttgcatc tggccgcgtt tcgtcgcgca ggcccgagcg      180
gcgttcggaa aagaccacac gattcgcatc gcaacggtcg tgaatttccc ctccggcgat      240
```

-continued

```
ctcgatgtcg cgaccgtggt tgcggaaacg gaagctgcaa tcggcgatgg cgccgacgaa      300
atcgatctgg tcattcccta tcgtaaattc atggcaggcg atgaatcggc ggtggccgaa      360
atgatcgcgg ccgtgcgtaa ggcttgcgcg gcacctgtgt tgctcaaggt cattcttgag      420
accggtgagc tgaaggacaa ggccctgatc cgccgtgcct cggaaatcgc cattgccgaa      480
ggggcggatt tcatcaagac ctcgaccggc aaggtcgccg tcaatgccac gctggaagcg      540
gccgatatca tgctgcaggc gatccgggac agcaaaaaga aggtgggctt caagccggcc      600
ggcggcatcg gcacggtgga ggacgcgaca ctataccctgc ggctggcgga aaccatcatg      660
gcgcccaact gggccatgcc gtcgaccttc cgtttcggtg cctcgggcgt cctcgatgat      720
gtgctgaacg tgctggccgg cggcgaaccg gccaaggccg ccagcgggta ttaa           774
```

<210> SEQ ID NO 30
<211> LENGTH: 257
<212> TYPE: PRT
<213> ORGANISM: Agrobacterium tumefaciens

<400> SEQUENCE: 30

```
Met Glu Leu Gln Arg Pro Arg Glu Ala Ala Leu Thr Leu Ser Leu
  1               5                  10                  15

Leu Asp Leu Thr Asn Leu Arg Glu Asp Cys Thr Pro Gln Gln Ile Ala
             20                  25                  30

Thr Leu Cys Gln Arg Ala His Thr Glu Phe Gly Asn Thr Ala Ala Ile
         35                  40                  45

Cys Ile Trp Pro Arg Phe Val Ala Gln Ala Arg Ala Phe Gly Lys
     50                  55                  60

Asp His Thr Ile Arg Ile Ala Thr Val Val Asn Phe Pro Ser Gly Asp
 65                  70                  75                  80

Leu Asp Val Ala Thr Val Ala Glu Thr Glu Ala Ala Ile Gly Asp
                 85                  90                  95

Gly Ala Asp Glu Ile Asp Leu Val Ile Pro Tyr Arg Lys Phe Met Ala
            100                 105                 110

Gly Asp Glu Ser Ala Val Ala Glu Met Ile Ala Ala Val Arg Lys Ala
        115                 120                 125

Cys Ala Ala Pro Val Leu Leu Lys Val Ile Leu Glu Thr Gly Glu Leu
    130                 135                 140

Lys Asp Lys Ala Leu Ile Arg Arg Ala Ser Glu Ile Ala Ile Ala Glu
145                 150                 155                 160

Gly Ala Asp Phe Ile Lys Thr Ser Thr Gly Lys Val Ala Val Asn Ala
                165                 170                 175

Thr Leu Glu Ala Ala Asp Ile Met Leu Gln Ala Ile Arg Asp Ser Lys
            180                 185                 190

Lys Lys Val Gly Phe Lys Pro Ala Gly Gly Ile Gly Thr Val Glu Asp
        195                 200                 205

Ala Thr Leu Tyr Leu Arg Leu Ala Glu Thr Ile Met Ala Pro Asn Trp
    210                 215                 220

Ala Met Pro Ser Thr Phe Arg Phe Gly Ala Ser Gly Val Leu Asp Asp
225                 230                 235                 240

Val Leu Asn Val Leu Ala Gly Gly Glu Pro Ala Lys Ala Ala Ser Gly
                245                 250                 255

Tyr
```

US 8,148,324 B2

CHEMOENZYMATIC METHODS FOR THE SYNTHESIS OF STATINS AND STATIN INTERMEDIATES

RELATED APPLICATIONS

This application is divisional of U.S. patent application Ser. No. 10/472,157, filed Aug. 19, 2003 (Intl.), now pending, which is a national phase application claiming benefit of priority under 35 U.S.C. §371 to Patent Convention Treaty (PCT) International Application Serial No: PCT/US03/27334, filed Aug. 19, 2003, which claims benefit of priority to U.S. Provisional Patent Application Ser. No. 60/412,625, filed Sep. 20, 2002, and U.S. Ser. No. 60/469,374, filed May 9, 2003. The aforementioned applications are explicitly incorporated herein by reference in their entirety and for all purposes.

SEQUENCE LISTING

This application is being filed electronically via the USPTO EFS-WEB server, as authorized and set forth in MPEP §1730 II.B.2(a)(A), and this electronic filing includes an electronically submitted sequence (SEQ ID) listing. The entire content of the sequence listing is herein incorporated by reference for all purposes. The sequence listing is identified on the electronically filed .txt file as follows:

| File Name | Date of Creation | Size (bytes) |
|---|---|---|
| 564462008810SEQLIST.txt | 02/08/2008 | 44,304 bytes |

TECHNICAL FIELD

This invention relates to the field of synthetic organic and medicinal chemistry, and pharmaceuticals. In particular, the invention provides novel aldolases, nucleic acids encoding them and methods for making and using them, including chemoenzymatic processes for making β,δ-dihydroxyheptanoic acid side chains and compositions comprising these side chains, e.g., (R)-ethyl-4-cyano-3-hydroxybutyrate (atorvastatin, LIPITOR™), rosuvastatin (CRESTOR™), fluvastatin (LESCOL™), related compounds, e.g., statins, and their intermediates.

BACKGROUND

The importance of chiral drugs in the pharmaceutical market increases with each year. Single stereoisomers on the market have proven to be safer, exhibit fewer side effects, and are more potent than what achiral drugs have been previously able to afford. The fact that pharmaceutical companies can now consider the practicality of marketing chiral drugs is partially due to the ability of synthetic chemists to be able to obtain high enantiomeric excess in asymmetric bond construction.

[R—(R*,R*)]-2-(4-fluorophenyl)-b,d-dihydroxy-5-(1-methylethyl)-3-phenyl-4-(phenylamino)-carbonyl]-1H-pyrrole-1-heptanoic acid (atorvastatin, LIPITOR™), whose structure is set forth in FIG. 5, belongs to a class of drugs called statins. Statins reduce the level of total cholesterol and LDL by inhibiting HMG-CoA reductase, an enzyme that catalyzes the conversion of HMG-CoA to mevalonate. Atorvastatin is the most potent of the statins. Atorvastatin contains a chiral β,δ-dihydroxyheptanoic acid side chain that requires a significant effort to produce on a large scale. Fluvastatin (LESCOL™) is water soluble and acts through the inhibition of 3-hydroxy-3-methylglutaryl-coenzyme A (HMG-CoA) reductase.

The aldol addition reaction, or aldol condensation, is a fundamental organic chemistry method for the formation and dissociation of carbon-carbon bonds. The aldol condensation can create two contiguous stereogenic centers and, consequently, four stereoisomers. Some control over the stereoselectivity can be obtained by the use of preformed enolates with metals. However, these reagents are stoichiometric and require extensive protecting group chemistry. See, for example, C. H. Heathcock, Aldrichim. Acta (1990): vol. 23, p 99; C. H. Heathcock, Science (1981): vol. 214, p 395; D. A. Evans, Science (1988): vol. 240, p 420; S. Masamune, et al., Angew. Chem. Int. Ed. Engl. (1985): vol. 24, p 1; D. A. Evans, et al., Top. Stereochem. (1982): vol. 13, p 1; C. H. Heathcocket et al., in Comprehensive Organic Synthesis, B. M. Trost, Ed. (Pergamon, Oxford, 1991), vol. 2, pp. 133-319 (1991); and I. Paterson, Pure & Appl. Chem. (1992): vol. 64, 1821.

Enantioselectivity can be obtained by using either chiral enol derivatives, chiral aldehydes or ketones, or both. However, recent studies of catalytic antibodies opened ways to obtain enantiomerically pure aldols via resolution. Thus, for some reactions, the problem of complex intermediates may be solved by using relatively reactive compounds rather than the more usual inert antigens to immunize animals or select antibodies from libraries such that the process of antibody induction involves an actual chemical reaction in the binding site. See, for example, C. F. Barbas III, et al., Proc. Natl. Acad. Sci. USA (1991): vol. 88, p 7978 (1991); K. D. Janda et al., Proc. Natl. Acad. Sci. USA (1994): vol. 191, p 2532. This same reaction then becomes part of the catalytic mechanism when the antibody interacts with a substrate that shares chemical reactivity with the antigen used to induce it.

The mechanisms of aldol condensation by aldolases have been well characterized. C. Y. Lai, et al., Science (1974): vol. 183, p 1204; and A. J. Morris e al., Biochemistry (1994) vol. 33, p 12291. The enzyme 2-deoxyribose-5-phosphate aldolase (DERA) in vivo catalyzes reversible aldol reaction of acetaldehyde and D-glyceraldehyde 3-phosphate to form D-2-deoxyribose-5-phosphate, the sugar moiety of DNA. Consequently this type I aldolase is widespread in nature. It is the only aldolase that accepts two aldehydes as substrates. Recent studies show that, in certain DERA-catalyzed reactions, product of the first aldol condensation can become an acceptor substrate for a second aldol condensation catalyzed by DERA or another aldolase. Thus, DERA and other aldolases can be used in combination for sequential aldol reactions leading to products with multiple chiral centers, starting from simple, non-chiral substrates. Gijsen, H., Wong, C.-H., JACS, vol. 117, 7585-7591. This enzyme can provide a route to a wide range of potentially biologically active compounds, e.g., the synthesis of deoxysugars such as deoxyriboses, 2-deoxyfucose analogs, and 13C-substituted D-2-deoxyribose-5-phosphate. See, for example, U.S. Pat. No. 5,795,749. It also affords a route to a variety of chiral aldehydes as illustrated in FIG. 6.

SUMMARY

The invention provides chemoenzymatic processes for making β,δ-dihydroxyheptanoic acid side chains and compositions comprising these side chains, e.g., statins. The invention provides methods for the enantioselective assembling of chiral β,δ-dihydroxyheptanoic acid side chains, including compositions comprising β,δ-dihydroxyheptanoic acid side chain cores, e.g., statins, such as [R—(R*,R*)]-2-(4-fluorophenyl)-b,d-dihydroxy-5-(1-methylethyl)-3-phenyl-4-(phenylamino)-carbonyl]-1H-pyrrole-1-heptanoic acid (atorvastatin, LIPITOR™), rosuvastatin (CRESTOR™), fluvastatin (LESCOL™), related compounds and their intermediates. In one aspect, the methods provide an enantioselective synthesis of both stereogenic centers of atorvastatin and/or rosuvastatin, and β,δ-dihydroxyheptanoic acid side chain-containing intermediates, in a single transformation from low-cost starting materials.

The invention provides methods for preparation of a compound having a formula as set forth as intermediate II in FIG. 7, comprising the following steps: (a) providing an aldol donor substrate; (b) providing an aldol acceptor substrate; (c) providing an aldolase; (d) admixing the aldol donor substrate of step (a), the aldol acceptor substrate of step (b), and the aldolase of step (c) under conditions wherein the aldolase can catalyze the aldol condensation reaction between the substrates of steps (a) and (b) thereby producing a compound comprising a structure as set forth as intermediate II in FIG. 7. In one aspect, the aldol acceptor substrate comprises an aldehyde. In one aspect, the aldehyde aldol acceptor substrate comprises a structure as set forth as aldehyde III in FIG. 7. In one aspect, R in the aldehyde III of FIG. 7 is selected from the group consisting of a hydrogen group, an alkyl group, a C1-C4 alkoxy group, a halogen, a cyan group and an azido group. In one aspect, R in the aldehyde III of FIG. 7 is chlorine and aldehyde III is chloroacetaldehyde.

In one aspect the method further comprises converting the intermediate II in FIG. 7 to a compound comprising a β,δ-dihydroxyheptanoic acid side chain. In one aspect, the compound comprising a β,δ-dihydroxyheptanoic acid side chain comprises a structure as set forth in formula I of FIG. 7. In one aspect, the aldolase is a 2-deoxyribose-5-phosphate aldolase (DERA), e.g., a recombinant 2-deoxyribose-5-phosphate aldolase (DERA). In one aspect, the aldolase comprises a polypeptide as set forth in SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30, or an enzymatically active fragment thereof. In one aspect, the aldolase comprises a polypeptide of the invention, or, a polypeptide encoded by a nucleic acid of the invention.

In one aspect, the aldol donor substrate comprises an acetaldehyde. In one aspect, the aldol donor substrate comprises an acetaldehyde and the aldol acceptor substrate comprises an aldehyde. In one aspect, the acetaldehyde is present in stoichiometric excess over the aldehyde. In one aspect, the reaction of step (d) is carried out in the absence of light. In one aspect, the reaction of step (d) is carried out at a temperature comprising a range from about 5° C. to about 45° C. and a pH value of about 6.5 to 8.5.

In one aspect, the method further comprises converting the intermediate II in FIG. 7 to a lactone compound. In one aspect, the lactone is a chloro-lactone, e.g., a 6-chloro-2,4,6-trideoxyerythro-hexonolactone. In one aspect, the lactone is crystalline. In one aspect, the crystalline lactone is purified by recrystallization.

In one aspect, the formation of 6-chloro-2,4,6-trideoxy-erythro-hexonolactone (chloro-lactone VI in FIG. 9) is carried out under oxidation conditions, e.g., comprising bromine ($Br_2$), $BrCO_3$ and water, a bromine/barium carbonate oxidation, as illustrated in FIG. 9. In one aspect, the method comprises a bromine/barium carbonate oxidation with sodium hypochlorite (NaOCl) in acetic acid (HOAc) and water.

In one aspect, the method further comprises converting the lactone compound to a compound as set forth as intermediate VIII in FIG. 10. In one aspect, the method further comprises converting the chloro-lactone to a compound set forth as lactone IX of FIG. 10. In one aspect, the chloro-lactone is converted to a compound set forth as lactone IX of FIG. 10 by subjecting the chloro-lactone to a cyanide displacement under conditions wherein the chloro group of the lactone is replaced by a cyan group CN.

In one aspect, the method further comprises converting the lactone IX to an intermediate VII of FIG. 10. In one aspect, the lactone IX is converted to an intermediate VII of FIG. 10 under conditions comprising treatment with MeOH and Dowex or MeOH and $K_2CO_3$, wherein the lactone ring opens and the intermediate VII is formed. In one aspect, the method further comprises further comprising converting the intermediate VII to an intermediate VIII of FIG. 10. In one aspect, the method further comprises processing the lactone to a compound comprising formula I of FIG. 7.

In one aspect, all reactions occur in a single reaction vessel. In one aspect, the intermediate II in FIG. 7 is a chloro-substituted intermediate having a structure as set forth as intermediate II in Route I, FIG. 8. In one aspect, the intermediate II in Route I, FIG. 8 is converted to a lactone by a process comprising CN-displacement, lactal oxidation and nitrile reduction.

In one aspect, the intermediate II in Route I, FIG. 8 is converted to a lactone by a process comprising bromine/barium carbonate oxidation to a chlorolactone. The method using bromine/barium carbonate oxidation can comprise oxidation with sodium hypochlorite (NaOCl) in acetic acid (HOAc) and water, as illustrated in FIG. 9.

In one aspect, the intermediate II in FIG. 7 is a cyan-substituted intermediate having a structure as set forth as intermediate II in Route II, FIG. 8. In one aspect, the intermediate II in Route II, FIG. 8 is converted to a lactone by a process comprising lactal oxidation and nitrile reduction. In one aspect, the intermediate II is an $N_3$-substituted intermediate having a structure as set forth as intermediate II in Route III, FIG. 8. In one aspect, the intermediate II in Route III, FIG. 8 is converted to a lactone by a process comprising lactal oxidation and azide reduction.

In one aspect, the method further comprises oxidation of the compound comprising intermediate II in FIG. 7, wherein R is a halogen, to make a compound comprising 3R,5S-6-chloro-2,4,6-trideoxy-erythro-hexonolactone (formula I in FIG. 14). In one aspect, the oxidation conditions comprise CN— displacement, lactal oxidation and nitrile oxidation. In one aspect, R is a chlorine.

In one aspect, the method further comprises processing the 3R,5S-6-chloro-2,4,6-trideoxy-erythro-hexonolactone to make (3R,5R)-6-cyano-3,5,-dihydroxyhexanoic acid (compound I of FIG. 14). In one aspect, the process comprises ring-opening. In one aspect, the process comprises ring-opening with cyanide. In one aspect, the method further comprises processing (3R,5R)-6-cyano-3,5,-dihydroxyhexanoic acid (compound I of FIG. 14) to make [R—(R*,R*)]-2-(4-fluorophenyl)-b,d-dihydroxy-5-(1-methylethyl)-3-phenyl-4-(phenylamino)-carbonyl]-1H-pyrrole-1-heptanoic acid (atorvastatin, LIPITOR™). In one aspect, the method further comprises processing the 3R,5S-6-chloro-2,4,6-trideoxy-erythro-hexonolactone to make (3R,5S)-3,5,6-trihydroxy-hexanoic acid (compound II of FIG. 14). In one aspect, the process comprises nucleophilic displacement. In one aspect, the nucleophilic displacement process comprises use of a hydroxide, e.g., sodium hydroxide. In one aspect, the method further comprises processing (3R,5S)-3,5,6-trihydroxyhexanoic acid (compound II of FIG. 14) to make a rosuvastatin (CRESTOR™). In one aspect, the method further comprises processing (3R,5S)-3,5,6-trihydroxyhexanoic acid (compound II of FIG. 14) to make fluvastatin (LESCOL™).

The invention provides processes for making [R—(R*,R*)]-2-(4-fluorophenyl)-b,d-dihydroxy-5-(1-methylethyl)-3-phenyl-4-(phenylamino)-carbonyl]-1H-pyrrole-1-heptanoic acid (atorvastatin, LIPITOR™) comprising a process as set forth in FIG. 14, FIG. 17 and FIG. 18. FIG. 18 illustrates a process of the invention comprising a chemoenzymatic route to make an atorvastatin (LIPITOR™) intermediate. The invention provides a process for making compound I of FIG. 18 using a DERA, e.g., using a DERA of the invention, using a process as set forth in FIG. 18. The invention provides a process for making compound II of FIG. 18 using a DERA, e.g., using a DERA of the invention, using a process as set forth in FIG. 18. The invention provides a process for making compound III of FIG. 18 using a DERA, e.g., using a DERA of the invention, using a process as set forth in FIG. 18. The invention provides a process for making compound II of FIG. 18 from compound I of FIG. 18 using dimethyloxypropane, MeOH and $H_2SO_4$, as set forth in FIG. 18. The invention provides a process for making compound III of FIG. 18 from compound II of FIG. 18 using $H_2$, Raney Nickel, 7N $NH_3$ at 46° C., as set forth in FIG. 18. These are a concise and simple syntheses from inexpensive materials.

The invention provides processes for making rosuvastatin (CRESTOR™) comprising a process as set forth in FIG. 14 and FIG. 17. The invention provides processes for making rosuvastatin (CRESTOR™) and fluvastatin (LESCOL™) comprising a process as set forth in FIG. 17.

The invention provides methods for preparation of a compound having a formula as set forth as intermediate II in FIG. 7, using a fed-batch process, comprising the following steps: (a) providing an aldol donor substrate; (b) providing an aldol acceptor substrate; (c) providing an aldolase; (d) admixing the aldol donor substrate of step (a), the aldol acceptor substrate of step (b), and the aldolase of step (c) under conditions wherein the aldolase can catalyze the aldol condensation reaction between the substrates of steps (a) and (b), wherein the substrates are fed into the reaction over about at least about 30 minutes to about 12, 15, 18, 21, 24 or more hours at a rate such that they are consumed as fast as they are added. In one aspect, one of the substrates is chloroacetaldehyde, and the substrates are fed into the reaction at a rate such that they are consumed as fast as they are added and the chloroacetaldehyde does not reach inhibitory concentration. In one aspect, the substrates are fed into the reaction over a time range of about 1 to 10 hours, or, about 2 to 8 hours, or, about 2 to 4 hours, or, about 2 to 3 hours. In one aspect, the method further comprises processing intermediate II as in FIG. 7 to make an atorvastatin (LIPITOR™). In one aspect, the method further comprises processing intermediate II as in FIG. 7 to make a rosuvastatin (CRESTOR™) and/or fluvastatin (LESCOL™). In one aspect, the aldolase is a 2-deoxyribose-5-phosphate aldolase (DERA), e.g., a recombinant 2-deoxyribose-5-phosphate aldolase (DERA). In one aspect, the aldolase comprises a polypeptide as set forth in SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30, or an enzymatically active fragment thereof. In one aspect, the aldolase comprises a polypeptide of the invention, or, a polypeptide encoded by a nucleic acid of the invention.

The invention provides methods for making 3R,5S-6-chloro-2,4,6-trideoxy-erythro-hexonolactone (compound I of FIG. 14) comprising oxidation of a chlorolactol to a chlorolactone with sodium hypochlorite. In one aspect, the chlorolactone comprises a crystalline chlorolactone. In one aspect, the chlorolactol comprises a crude chlorolactol. In one aspect, the chlorolactol is dissolved in glacial acetic acid, and about 1 equivalent of aqueous sodium hypochlorite is fed into the solution. In one aspect, about 1 equivalent of aqueous sodium hypochlorite is fed into the solution over about 3 hours.

The invention provides methods for making 3R,5S-6-chloro-2,4,6-trideoxy-erythro-hexonolactone (compound I of FIG. 14) comprising a process as set forth in FIG. 14 and/or FIG. 15.

The invention provides methods for making an epoxide (-(3R,5S-3-hydroxy-4-oxiranylbutyric acid) (structure 2 in FIG. 16) using a process as set forth in FIG. 16. In one aspect, the method comprises use of NaCN (e.g., 3 equivalents of NaCN), dimethylformamide (DMF) and water (e.g., 5% $H_2O$, DMF with 5% water by volume). In another aspect, the method comprises use of 2.2 equivalents of NaCN, water (e.g., 5% $H_2O$) at about 40° C., for about 20 hours. These processes can generate the intermediate (3R,5R)-6-cyano-3,5,-dihydroexyhexanoic acid (a protected side chain intermediate). In one aspect, this is a one-pot process. In one aspect of the reaction in FIG. 16 and FIG. 18, the lactone ring is opened and chloride is displaced by hydroxide, again through the epoxide intermediate, to access the trihydroxy acid. The reaction conditions can comprise 2 equivalents of sodium hydroxide in water.

The invention provides methods for making (3R,5S)-3,5,6-trihydroxyhexanoic acid comprising a process as set forth in FIG. 16 and FIG. 18, e.g., through the epoxide intermediate -(3R,5S-3-hydroxy-4-oxiranylbutyric acid. In one aspect, the process comprises use of water and NaOH. In one aspect, this is a one-pot process.

In one aspect, the invention provides a one pot process to make statin intermediates comprising a lactone opening and a cyanide displacement through epoxide intermediates (e.g., -(3R,5S-3-hydroxy-4-oxiranylbutyric acid, structure 2 in FIG. 16), as set forth in FIG. 16 and FIG. 18. In one aspect, the invention provides a one pot process for making (3R,5S)-3,5,6-trihydroxyhexanoic acid comprising a process as set forth in FIG. 16 and FIG. 18. The methods can further comprise synthesis of atorvastatin (LIPITOR™), rosuvastatin (CRESTOR™), fluvastatin (LESCOL™) and related compounds. A complete exemplary process for the synthesis of statin intermediates (for, e.g., synthesis of atorvastatin (LIPITOR™), rosuvastatin (CRESTOR™), fluvastatin (LESCOL™) and related compounds) is illustrated in FIG. 21. In alternative aspects various steps of the process, or the entire process, is a one-pot process.

The invention provides isolated or recombinant nucleic acids comprising a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:5 over a region of at least about 10, 15, 20, 25, 30, 35, 40, 45, 50, 75, 100, 150, 200, 250, 300, 350, 400, 450, 500, 550, 600, 650, 700, or more residues, encodes at least one polypeptide having aldolase activity, and the sequence identities are determined by analysis with a sequence comparison algorithm or by a visual inspection.

The invention provides isolated or recombinant nucleic acids comprising a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:7 over a region of at least about 10, 15, 20, 25, 30, 35, 40, 45, 50, 75, 100, 150, 200, 250, 300, 350, 400, 450, 500, 550, 600, 650, 700, or more residues, encodes at least one polypeptide having aldolase activity, and the sequence identities are determined by analysis with a sequence comparison algorithm or by a visual inspection.

The invention provides isolated or recombinant nucleic acids comprising a nucleic acid sequence having at least about 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:9 over a region of at least about 10, 15, 20, 25, 30, 35, 40, 45, 50, 75, 100, 150, 200, 250, 300, 350, 400, 450, 500, 550, 600, 650, 700, or more residues, encodes at least one polypeptide having aldolase activity, and the sequence identities are determined by analysis with a sequence comparison algorithm or by a visual inspection.

The invention provides isolated or recombinant nucleic acids comprising a nucleic acid sequence having at least about 91%, 92%, 93%, 94%, 95%, 96%, 97%, 98%, 99%, or more, or complete (100%) sequence identity to SEQ ID NO:11 over a region of at least about 10, 15, 20, 25, 30, 35, 40, 45, 50, 75, 100, 150, 200, 250, 300, 350, 400, 450, 500, 550, 600, 650, 700, or more residues, encodes at least one polypeptide having aldolase activity, and the sequence identities are determined by analysis with a sequence comparison algorithm or by a visual inspection.

The invention provides isolated or recombinant nucleic acids comprising a nucleic acid sequence having at least about 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:13 over a region of at least about 10, 15, 20, 25, 30, 35, 40, 45, 50, 75, 100, 150, 200, 250, 300, 350, 400, 450, 500, 550, 600, 650, 700, or more residues, encodes at least one polypeptide having aldolase activity, and the sequence identities are determined by analysis with a sequence comparison algorithm or by a visual inspection.

The invention provides isolated or recombinant nucleic acids comprising a nucleic acid sequence having at least about 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:15 over a region of at least about 10, 15, 20, 25, 30, 35, 40, 45, 50, 75, 100, 150, 200, 250, 300, 350, 400, 450, 500, 550, 600, 650, 700, or more residues, encodes at least one polypeptide having aldolase activity, and the sequence identities are determined by analysis with a sequence comparison algorithm or by a visual inspection.

The invention provides isolated or recombinant nucleic acids comprising a nucleic acid sequence having at least about 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:17 over a region of at least about 10, 15, 20, 25, 30, 35, 40, 45, 50, 75, 100, 150, 200, 250, 300, 350, 400, 450, 500, 550, 600, 650, 700, or more residues, encodes at least one polypeptide having aldolase activity, and the sequence identities are determined by analysis with a sequence comparison algorithm or by a visual inspection.

The invention provides isolated or recombinant nucleic acids comprising a nucleic acid sequence having at least about 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:19 over a region of at least about 10, 15, 20, 25, 30, 35, 40, 45, 50, 75, 100, 150, 200, 250, 300, 350, 400, 450, 500, 550, 600, 650, 700, or more residues, encodes at least one polypeptide having aldolase activity, and the sequence identities are determined by analysis with a sequence comparison algorithm or by a visual inspection.

The invention provides isolated or recombinant nucleic acids comprising a nucleic acid sequence having at least about 99%, 99.5%, 99.8%, or more, or complete (100%) sequence identity to SEQ ID NO:21 over a region of at least about 10, 15, 20, 25, 30, 35, 40, 45, 50, 75, 100, 150, 200, 250, 300, 350, 400, 450, 500, 550, 600, 650, 700, or more residues, encodes at least one polypeptide having aldolase activity, and the sequence identities are determined by analysis with a sequence comparison algorithm or by a visual inspection.

In alternative aspects, the isolated, synthetic or recombinant nucleic acid encodes a polypeptide comprising a sequence as set forth in SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30, or an enzymatically active fragment thereof. In one aspect these polypeptides have an aldolase activity.

In one aspect, the sequence comparison algorithm is a BLAST algorithm, such as a BLAST version 2.2.2 algorithm. In one aspect, the filtering setting is set to blastall-p blastp-d "nr pataa"-F F and all other options are set to default.

In one aspect, the aldolase activity comprises catalysis of the formation of a carbon-carbon bond. In one aspect, the aldolase activity comprises an aldol condensation. The aldol condensation can have an aldol donor substrate comprising an acetaldehyde and an aldol acceptor substrate comprising an aldehyde. The aldol condensation can yield a product of a single chirality. In one aspect, the aldolase activity is enantioselective. The aldolase activity can comprise a 2-deoxyribose-5-phosphate aldolase (DERA) activity. The aldolase activity can comprise catalysis of the condensation of acetaldehyde as donor and a 2(R)-hydroxy-3-(hydroxy or mercapto)-propionaldehyde derivative to form a 2-deoxysugar. The aldolase activity can comprise catalysis of the condensation of acetaldehyde as donor and a 2-substituted acetaldehyde acceptor to form a 2,4,6-trideoxyhexose via a 4-substituted-3-hydroxybutanal intermediate. The aldolase activity can comprise catalysis of the generation of chiral aldehydes using two acetaldehydes as substrates. The aldolase activity can comprises enantioselective assembling of chiral β,δ-dihydroxyheptanoic acid side chains. The aldolase activity can comprise enantioselective assembling of the core of [R—(R*, R*)]-2-(4-fluorophenyl)-b,d-dihydroxy-5-(1-methylethyl)-3-phenyl-4-(phenylamino)-carbonyl]-1H-pyrrole-1-heptanoic acid (Atorvastatin, or LIPITOR™), rosuvastatin (CRESTOR™) and/or fluvastatin (LESCOL™). The aldolase activity can comprise, with an oxidation step, synthesis of a 3R,5S-6-chloro-2,4,6-trideoxy-erythro-hexonolactone.

In one aspect, the isolated or recombinant nucleic acid encodes a polypeptide having an aldolase activity which is thermostable. The polypeptide can retain an aldolase activity under conditions comprising a temperature anywhere in a range of between about 1° C. to about 5° C., about 5° C. to about 15° C., about 15° C. to about 25° C., about 25° C. to about 37° C., 37° C. to about 95° C.; between about 55° C. to about 85° C., between about 70° C. to about 95° C., or, between about 90° C. to about 95° C., 96° C., 97° C. or more. In another aspect, the isolated or recombinant nucleic acid encodes a polypeptide having an aldolase activity which is thermotolerant. The polypeptide can retain an aldolase activity after exposure to a temperature anywhere in a range of between about 1° C. to about 5° C., about 5° C. to about 15° C., about 15° C. to about 25° C., about 25° C. to about 37° C., 37° C. to about 95° C.; between about 55° C. to about 85° C., between about 70° C. to about 95° C., or, between about 90° C. to about 95° C., 96° C., 97° C. or more.

In one aspect, the polypeptide can retain an aldolase activity under conditions comprising about pH 6.5, pH 6, pH 5.5, pH 5, pH 4.5 or pH 4. In another aspect, the polypeptide can retain an aldolase activity under conditions comprising about pH 7, pH 7.5 pH 8.0, pH 8.5, pH 9, pH 9.5, pH 10, pH 10.5 or pH 1. In one aspect, the polypeptide can retain an aldolase activity after exposure to conditions comprising about pH 6.5, pH 6, pH 5.5, pH 5, pH 4.5 or pH 4. In another aspect, the polypeptide can retain an aldolase activity after exposure to conditions comprising about pH 7, pH 7.5 pH 8.0, pH 8.5, pH9,pH 9.5, pH 10,pH 10.5 or pH 11.

In one aspect, the isolated, synthetic or recombinant nucleic acid comprises a sequence that hybridizes under stringent conditions to a sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, wherein the nucleic acid encodes a polypeptide having an aldolase activity. The nucleic acid can at least about 10, 20, 30, 40, 50, 60, 70, 80, 90, 100, 150, 200, 250, 300, 350, 400, 450, 500, 550, 600, 650, 700, 750, 800, 850 or residues in length or the full length of the gene or transcript, with or without a signal sequence, as described herein. The stringent conditions can be highly stringent, moderately stringent or of low stringency, as described herein. The stringent conditions can include a wash step, e.g., a wash step comprising a wash in 0.2×SSC at a temperature of about 65° C. for about 15 minutes.

The invention provides a nucleic acid probe for identifying a nucleic acid encoding a polypeptide with an aldolase activity, wherein the probe comprises at least 10, 20, 30, 40, 50, 60, 70, 80, 90, 100, 150, 200, 250, 300, 350, 400, 450, 500, 550, 600, 650, 700, 750, 800, 850, or more, consecutive bases of a sequence of the invention, e.g., as exemplary sequence SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and the probe identifies the nucleic acid by binding or hybridization. The probe can comprise an oligonucleotide comprising at least about 10 to 50, about 20 to 60, about 30 to 70, about 40 to 80, or about 60 to 100 consecutive bases of a sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29.

The invention provides a nucleic acid probe for identifying a nucleic acid encoding a polypeptide with an aldolase activity, wherein the probe comprises a nucleic acid of the invention, e.g., a nucleic acid having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:1, SEQ ID NO:3, SEQ ID NO:5, SEQ ID NO:7, SEQ ID NO:9, SEQ ID NO:1, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, over a region of at least about 10, 20, 30, 40, 50, 60, 70, 80, 90, 100, 150, 200, 250, 300, 350, 400, 450, 500, 550, 600, 650, 700, 750, 800, 850 or more consecutive residues, wherein the sequence identities are determined by analysis with a sequence comparison algorithm or by visual inspection.

The invention provides an amplification primer sequence pair for amplifying a nucleic acid encoding a polypeptide having an aldolase activity, wherein the primer pair is capable of amplifying a nucleic acid comprising a sequence of the invention, or fragments or subsequences thereof. In one aspect, one or each member of the amplification primer sequence pair comprises an oligonucleotide comprising at least about 10 to 50 consecutive bases of the sequence, or about 12, 13, 14, 15, 16, 17, 18, 19, 20, 21, 22, 23, 24, or 25 consecutive bases of the sequence.

The invention provides amplification primer pairs, wherein the primer pair comprises a first member having a sequence as set forth by about the first (the 5') 12, 13, 14, 15, 16, 17, 18, 19, 20, 21, 22, 23, 24, 25, 26, 27, 28, 29, 30 or more residues of a nucleic acid of the invention, and a second member having a sequence as set forth by about the first (the 5') 12, 13, 14, 15, 16, 17, 18, 19, 20, 21, 22, 23, 24, 25, 26, 27, 28, 29, 30 or more residues of the complementary strand of the first member.

The invention provides aldolases generated by amplification, e.g., polymerase chain reaction (PCR), using an amplification primer pair of the invention. The invention provides methods of making an aldolase by amplification, e.g., polymerase chain reaction (PCR), using an amplification primer pair of the invention. In one aspect, the amplification primer pair amplifies a nucleic acid from a library, e.g., a gene library, such as an environmental library.

The invention provides methods of amplifying a nucleic acid encoding a polypeptide having an aldolase activity comprising amplification of a template nucleic acid with an amplification primer sequence pair capable of amplifying a nucleic acid sequence of the invention, or fragments or subsequences thereof. The amplification primer pair can be an amplification primer pair of the invention.

The invention provides expression cassettes comprising a nucleic acid of the invention. In one aspect, the expression cassette can comprise the nucleic acid that is operably linked to a promoter. The promoter can be a viral, bacterial, mammalian or plant promoter. In one aspect, the plant promoter can be a potato, rice, corn, wheat, tobacco or barley promoter. The promoter can be a constitutive promoter. The constitutive promoter can comprise CaMV35S. In another aspect, the promoter can be an inducible promoter. In one aspect, the promoter can be a tissue-specific promoter or an environmentally regulated or a developmentally regulated promoter. Thus, the promoter can be, e.g., a seed-specific, a leaf-specific, a root-specific, a stem-specific or an abscission-induced promoter. In one aspect, the expression cassette can further comprise a plant or plant virus expression vector.

The invention provides cloning vehicles comprising an expression cassette (e.g., a vector) of the invention or a nucleic acid of the invention. The cloning vehicle can be a viral vector, a plasmid, a phage, a phagemid, a cosmid, a fosmid, a bacteriophage or an artificial chromosome. The viral vector can comprise an adenovirus vector, a retroviral vector or an adeno-associated viral vector. The cloning vehicle can comprise a bacterial artificial chromosome (BAC), a plasmid, a bacteriophage P1-derived vector (PAC), a yeast artificial chromosome (YAC), or a mammalian artificial chromosome (MAC).

The invention provides transformed cell comprising a nucleic acid of the invention or an expression cassette (e.g., a vector) of the invention, or a cloning vehicle of the invention. In one aspect, the transformed cell can be a bacterial cell, a mammalian cell, a fungal cell, a yeast cell, an insect cell or a plant cell. In one aspect, the plant cell can be a potato, wheat, rice, corn, tobacco or barley cell.

The invention provides transgenic non-human animals comprising a nucleic acid of the invention or an expression cassette (e.g., a vector) of the invention. In one aspect, the animal is a mouse.

The invention provides transgenic plants comprising a nucleic acid of the invention or an expression cassette (e.g., a vector) of the invention. The transgenic plant can be a corn plant, a potato plant, a tomato plant, a wheat plant, an oilseed plant, a rapeseed plant, a soybean plant, a rice plant, a barley plant or a tobacco plant. The invention provides transgenic seeds comprising a nucleic acid of the invention or an expression cassette (e.g., a vector) of the invention. The transgenic seed can be a corn seed, a wheat kernel, an oilseed, a rapeseed (a canola plant), a soybean seed, a palm kernel, a sunflower seed, a sesame seed, a peanut or a tobacco plant seed.

The invention provides an antisense oligonucleotide comprising a nucleic acid sequence complementary to or capable of hybridizing under stringent conditions to a nucleic acid of the invention. The invention provides methods of inhibiting the translation of an aldolase message in a cell comprising administering to the cell or expressing in the cell an antisense oligonucleotide comprising a nucleic acid sequence complementary to or capable of hybridizing under stringent conditions to a nucleic acid of the invention.

The invention provides an antisense oligonucleotide comprising a nucleic acid sequence complementary to or capable of hybridizing under stringent conditions to a nucleic acid of the invention. The invention provides methods of inhibiting the translation of an aldolase message in a cell comprising administering to the cell or expressing in the cell an antisense oligonucleotide comprising a nucleic acid sequence complementary to or capable of hybridizing under stringent conditions to a nucleic acid of the invention. The antisense oligonucleotide can be between about 10 to 50, about 20 to 60, about 30 to 70, about 40 to 80, about 60 to 100, about 70 to 110, or about 80 to 120 bases in length.

The invention provides methods of inhibiting the translation of an aldolase, e.g., an aldolase, message in a cell comprising administering to the cell or expressing in the cell an antisense oligonucleotide comprising a nucleic acid sequence complementary to or capable of hybridizing under stringent conditions to a nucleic acid of the invention. The invention provides double-stranded inhibitory RNA (RNAi) molecules comprising a subsequence of a sequence of the invention. In one aspect, the RNAi is about 15, 16, 17, 18, 19, 20, 21, 22, 23, 24, 25 or more duplex nucleotides in length. The invention provides methods of inhibiting the expression of an aldolase, e.g., an aldolase, in a cell comprising administering to the cell or expressing in the cell a double-stranded inhibitory RNA (iRNA), wherein the RNA comprises a subsequence of a sequence of the invention.

The invention provides isolated or recombinant polypeptides comprising a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:6 over a region of at least about 10, 15, 20, 25, 30, 35, 40, 45, 50, 75, 100, 150, 200, 250, 300 or more residues, wherein the sequence identities are determined by analysis with a sequence comparison algorithm or by a visual inspection.

The invention provides isolated or recombinant polypeptides comprising a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:8 over a region of at least about 10, 15, 20, 25, 30, 35, 40, 45, 50, 75, 100, 150, 200, 250, 300 or more residues, wherein the sequence identities are determined by analysis with a sequence comparison algorithm or by a visual inspection.

The invention provides isolated or recombinant polypeptides comprising a nucleic acid sequence having at least about 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:10 over a region of at least about 10, 15, 20, 25, 30, 35, 40, 45, 50, 75, 100, 150, 200, 250, 300 or more residues, wherein the sequence identities are determined by analysis with a sequence comparison algorithm or by a visual inspection.

The invention provides isolated or recombinant polypeptides comprising a nucleic acid sequence having at least about 91%, 92%, 93%, 94%, 95%, 96%, 97%, 98%, 99%, or more, or complete (100%) sequence identity to SEQ ID NO:12 over a region of at least about 10, 15, 20, 25, 30, 35, 40, 45, 50, 75, 100, 150, 200, 250, 300 or more residues, wherein the sequence identities are determined by analysis with a sequence comparison algorithm or by a visual inspection.

The invention provides isolated or recombinant polypeptides comprising a nucleic acid sequence having at least about 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:14 over a region of at least about 10, 15, 20, 25, 30, 35, 40, 45, 50, 75, 100, 150, 200, 250, 300 or more residues, wherein the sequence identities are determined by analysis with a sequence comparison algorithm or by a visual inspection.

The invention provides isolated or recombinant polypeptides comprising a nucleic acid sequence having at least about 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:16 over a region of at least about 10, 15, 20, 25, 30, 35, 40, 45, 50, 75, 100, 150, 200, 250, 300, or more residues, wherein the sequence identities are determined by analysis with a sequence comparison algorithm or by a visual inspection.

The invention provides isolated or recombinant polypeptides comprising a nucleic acid sequence having at least about 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:18 over a region of at least about 10, 15, 20, 25, 30, 35, 40, 45, 50, 75, 100, 150, 200, 250, 300 or more residues, encodes at least one polypeptide having aldolase activity, and the sequence identities are determined by analysis with a sequence comparison algorithm or by a visual inspection.

The invention provides isolated or recombinant polypeptides comprising a nucleic acid sequence having at least about 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:20 over a region of at least about 10, 15, 20, 25, 30, 35, 40, 45, 50, 75, 100, 150, 200, 250, 300, 350 or more residues, wherein the sequence identities are determined by analysis with a sequence comparison algorithm or by a visual inspection.

The invention provides isolated or recombinant polypeptides comprising a nucleic acid sequence having at least about 99%, 99.5%, 99.8%, or more, or complete (100%) sequence identity to SEQ BD NO:22 over a region of at least about 10, 15, 20, 25, 30, 35, 40, 45, 50, 75, 100, 150, 200, 250, 300, 350 or more residues, wherein the sequence identities are determined by analysis with a sequence comparison algorithm or by a visual inspection.

The invention provides isolated or recombinant polypeptides encoded by nucleic acid comprising a sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29. In alternative aspects, the isolated, synthetic or recombinant polypeptides comprise a sequence as set forth in SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30, or an enzymatically active fragment thereof. In one aspect these polypeptides have an aldolase activity.

Another aspect of the invention provides an isolated or recombinant polypeptide or peptide including at least 10, 15, 20, 25, 30, 35, 40, 45, 50, 55, 60, 65, 70, 75, 80, 85, 90, 95 or 100 or more consecutive bases of a polypeptide or peptide sequence of the invention (e.g., the exemplary SEQ ID NO:6, SEQ ID NO:8, SEQ ID NO:10, SEQ ID NO:12, SEQ ID NO:14, SEQ BD NO:16, SEQ ID NO:18, SEQ ID NO:20, SEQ ID NO:22, SEQ ID NO:24, SEQ ID NO:26, SEQ ID NO:28, or SEQ ID NO:30), sequences substantially identical thereto, and the sequences complementary thereto. The peptide can be, e.g., an immunogenic fragment, a motif (e.g., a binding site), a signal sequence, a prepro sequence or an active site.

In one aspect, the isolated or recombinant polypeptide of the invention (with or without a signal sequence) has an aldolase activity. In one aspect, the aldolase activity comprises catalysis of the formation of a carbon-carbon bond. In one aspect, the aldolase activity comprises an aldol condensation. The aldol condensation can have an aldol donor substrate comprising an acetaldehyde and an aldol acceptor substrate comprising an aldehyde. The aldol condensation can yield a product of a single chirality. In one aspect, the aldolase activity is enantioselective. The aldolase activity can comprise a 2-deoxyribose-5-phosphate aldolase (DERA) activity. The aldolase activity can comprise catalysis of the condensation of acetaldehyde as donor and a 2(R)-hydroxy-3-(hydroxy or mercapto)-propionaldehyde derivative to form a 2-deoxysugar. The aldolase activity can comprise catalysis of the condensation of acetaldehyde as donor and a 2-substituted acetaldehyde acceptor to form a 2,4,6-trideoxyhexose via a 4-substituted-3-hydroxybutanal intermediate. The aldolase activity can comprise catalysis of the generation of chiral aldehydes using two acetaldehydes as substrates. The aldolase activity can comprises enantioselective assembling of chiral β,δ-dihydroxyheptanoic acid side chains. The aldolase activity can comprise enantioselective assembling of the core of [R—(R*,R*)]-2-(4-fluorophenyl)-b,d-dihydroxy-5-(1-methylethyl)-3-phenyl-4-(phenylamino)-carbonyl]-1H-pyrrole-1-heptanoic acid (atorvastatin, or LIPITOR™), rosuvastatin (CRESTOR™) and/or fluvastatin (LESCOL™). The aldolase activity can comprise, with an oxidation step, synthesis of a 3R,5S-6-chloro-2,4,6-trideoxy-erythro-hexonolactone.

In one aspect, the aldolase activity is thermostable. A polypeptide of the invention can retain an aldolase activity under conditions comprising a temperature anywhere in a range of between about 1° C. to about 5° C., about 5° C. to about 15° C., about 15° C. to about 25° C., about 25° C. to about 37° C., 37° C. to about 95° C.; between about 55° C. to about 85° C., between about 70° C. to about 95° C., or, between about 90° C. to about 95° C., 96° C., 97° C. or more. In another aspect, the aldolase activity is thermotolerant. A polypeptide of the invention can retain an aldolase activity after exposure to a temperature anywhere in a range of between about 1° C. to about 5° C., about 5° C. to about 15° C., about 15° C. to about 25° C., about 25° C. to about 37° C., 37° C. to about 95° C.; between about 55° C. to about 85° C., between about 70° C. to about 95° C., or, between about 90° C. to about 95° C., 96° C., 97° C. or more.

In one aspect, the polypeptide can retain an aldolase activity under conditions comprising about pH 6.5, pH 6, pH 5.5, pH 5, pH 4.5 or pH 4. In another aspect, the polypeptide can retain an aldolase activity under conditions comprising about pH 7, pH 7.5 pH 8.0, pH 8.5, pH 9, pH 9.5, pH 10, pH 10.5 or pH 11. In one aspect, the polypeptide can retain an aldolase activity after exposure to conditions comprising about pH 6.5, pH 6, pH 5.5, pH 5, pH 4.5 or pH 4. In another aspect, the polypeptide can retain an aldolase activity after exposure to conditions comprising about pH 7, pH 7.5 pH 8.0, pH 8.5, pH 9, pH 9.5, pH 10, pH 10.5 or pH 11.

In one aspect, the isolated or recombinant polypeptide can comprise the polypeptide of the invention that lacks a signal sequence and/or a prepro domain. In one aspect, the isolated or recombinant polypeptide can comprise the polypeptide of the invention comprising a heterologous signal sequence and/or prepro domain, such as a heterologous aldolase or a non-aldolase signal sequence.

In one aspect, the invention provides a signal sequence comprising a peptide comprising/consisting of a sequence as set forth in residues 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 28, 1 to 30, 1 to 31, 1 to 32, 1 to 33, 1 to 34, 1 to 35, 1 to 36, 1 to 37, 1 to 38, 1 to 39, 1 to 40, 1 to 41, 1 to 42, 1 to 43, 1 to 44 of a polypeptide of the invention, e.g., the exemplary SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30.

The invention provides isolated or recombinant peptides comprising an amino acid sequence having at least 95%, 96%, 97%, 98%, 99%, or more, or complete sequence identity to residues 1 to 22 of SEQ ID NO:18, wherein the sequence identities are determined by analysis with a sequence comparison algorithm or by visual inspection. These peptides can act as signal sequences on its endogenous aldolase, on another aldolase, or a heterologous protein (a non-aldolase enzyme or other protein). In one aspect, the invention provides chimeric proteins comprising a first domain comprising a signal sequence of the invention and at least a second domain. The protein can be a fusion protein. The second domain can comprise an enzyme. The enzyme can be an aldolase.

The invention provides chimeric polypeptides comprising at least a first domain comprising signal peptide (SP), a prepro domain, a catalytic domain (CD), or an active site of an aldolase of the invention and at least a second domain comprising a heterologous polypeptide or peptide, wherein the heterologous polypeptide or peptide is not naturally associated with the signal peptide (SP), prepro domain or catalytic domain (CD). In one aspect, the heterologous polypeptide or peptide is not an aldolase. The heterologous polypeptide or peptide can be amino terminal to, carboxy terminal to or on both ends of the signal peptide (SP), prepro domain or catalytic domain (CD).

In one aspect, the aldolase activity comprises a specific activity at about 37° C. in the range from about 1 to about 1200 units per milligram (U/mg) of protein, or, about 100 to about 1000 units per milligram of protein, or, about 200 to about 800 units per milligram of protein. In another aspect, the aldolase activity comprises a specific activity from about 100 to about 1000 units per milligram of protein, or, from about 500 to about 750 units per milligram of protein. Alternatively, the aldolase activity comprises a specific activity at 37° C. in the range from about 1 to about 750 units per milligram of protein, or, from about 500 to about 1200 units per milligram of protein. In one aspect, the aldolase activity comprises a specific activity at 37° C. in the range from about 1 to about 500 units per milligram of protein, or, from about 750 to about 1000 units per milligram of protein. In another aspect, the aldolase activity comprises a specific activity at 37° C. in the range from about 1 to about 250 units per milligram of protein. Alternatively, the aldolase activity comprises a specific activity at 37° C. in the range from about 1 to about 100 units per milligram of protein. In another aspect, the thermotolerance comprises retention of at least half of the specific activity of the aldolase at 37° C. after being heated to the elevated temperature. Alternatively, the thermotolerance can comprise retention of specific activity at 37° C. in the range from about 1 to about 1200 units per milligram of protein, or, from about 500 to about 1000 units per milligram of protein, after being heated to the elevated temperature. In another aspect, the thermotolerance can comprise retention of specific activity at 37° C. in the range from about 1 to about 500 units per milligram of protein after being heated to the elevated temperature.

The invention provides the isolated or recombinant polypeptide of the invention, wherein the polypeptide comprises at least one glycosylation site. In one aspect, glycosylation can be an N-linked glycosylation. In one aspect, the polypeptide can be glycosylated after being expressed in a *P. pastoris* or a *S. pombe*.

The invention provides protein preparations comprising a polypeptide of the invention, wherein the protein preparation comprises a liquid, a solid or a gel.

The invention provides heterodimers comprising a polypeptide of the invention and a second protein or domain. The second member of the heterodimer can be a different aldolase, a different enzyme or another protein. In one aspect, the second domain can be a polypeptide and the heterodimer can be a fusion protein. In one aspect, the second domain can be an epitope or a tag. In one aspect, the invention provides homodimers comprising a polypeptide of the invention.

The invention provides immobilized polypeptides having an aldolase activity, wherein the polypeptide comprises a polypeptide of the invention, a polypeptide encoded by a nucleic acid of the invention, or a polypeptide comprising a polypeptide of the invention and a second domain. In one aspect, the polypeptide can be immobilized on a cell, a metal, a resin, a polymer, a ceramic, a glass, a microelectrode, a graphitic particle, a bead, a gel, a plate, an array or a capillary tube.

The invention provides arrays comprising an immobilized polypeptide, wherein the polypeptide is an aldolase of the invention or is a polypeptide encoded by a nucleic acid of the invention. The invention provides arrays comprising an immobilized nucleic acid of the invention. The invention provides an array comprising an immobilized antibody of the invention.

The invention provides isolated or recombinant antibodies that specifically bind to a polypeptide of the invention or to a polypeptide encoded by a nucleic acid of the invention. The antibody can be a monoclonal or a polyclonal antibody. The invention provides hybridomas comprising an antibody of the invention.

The invention provides methods of isolating or identifying a polypeptide with an aldolase activity comprising the steps of: (a) providing an antibody of the invention; (b) providing a sample comprising polypeptides; and, (c) contacting the sample of step (b) with the antibody of step (a) under conditions wherein the antibody can specifically bind to the polypeptide, thereby isolating or identifying an aldolase. The invention provides methods of making an anti-aldolase antibody comprising administering to a non-human animal a nucleic acid of the invention, or a polypeptide of the invention, in an amount sufficient to generate a humoral immune response, thereby making an anti-aldolase antibody.

The invention provides methods of producing a recombinant polypeptide comprising the steps of: (a) providing a nucleic acid of the invention operably linked to a promoter; and, (b) expressing the nucleic acid of step (a) under conditions that allow expression of the polypeptide, thereby producing a recombinant polypeptide. The method can further comprise transforming a host cell with the nucleic acid of step (a) followed by expressing the nucleic acid of step (a), thereby producing a recombinant polypeptide in a transformed cell. The method can further comprise inserting into a host non-human animal the nucleic acid of step (a) followed by expressing the nucleic acid of step (a), thereby producing a recombinant polypeptide in the host non-human animal.

The invention provides methods for identifying a polypeptide having an aldolase activity comprising the following steps: (a) providing a polypeptide of the invention or a polypeptide encoded by a nucleic acid of the invention, or a fragment or variant thereof, (b) providing an aldolase substrate; and, (c) contacting the polypeptide or a fragment or variant thereof of step (a) with the substrate of step (b) and detecting an increase in the amount of substrate or a decrease in the amount of reaction product, wherein a decrease in the amount of the substrate or an increase in the amount of the reaction product detects a polypeptide having an aldolase activity.

The invention provides methods for identifying an aldolase substrate comprising the following steps: (a) providing a polypeptide of the invention or a polypeptide encoded by a nucleic acid of the invention; (b) providing a test substrate; and, (c) contacting the polypeptide of step (a) with the test substrate of step (b) and detecting an increase in the amount of substrate or a decrease in the amount of reaction product, wherein a decrease in the amount of the substrate or an increase in the amount of the reaction product identifies the test substrate as an aldolase substrate.

The invention provides methods of determining whether a compound specifically binds to an aldolase comprising the following steps: (a) expressing a nucleic acid or a vector comprising the nucleic acid under conditions permissive for translation of the nucleic acid to a polypeptide, wherein the nucleic acid and vector comprise a nucleic acid or vector of the invention; or, providing a polypeptide of the invention (b) contacting the polypeptide with the test compound; and, (c) determining whether the test compound specifically binds to the polypeptide, thereby determining that the compound specifically binds to the aldolase.

The invention provides methods for identifying a modulator of an aldolase activity comprising the following steps: (a) providing a polypeptide of the invention or a polypeptide encoded by a nucleic acid of the invention; (b) providing a test compound; (c) contacting the polypeptide of step (a) with the test compound of step (b); and, measuring an activity of the aldolase, wherein a change in the aldolase activity measured in the presence of the test compound compared to the activity in the absence of the test compound provides a determination that the test compound modulates the aldolase activity.

In one aspect, the aldolase activity is measured by providing an aldolase substrate and detecting an increase in the amount of the substrate or a decrease in the amount of a reaction product. The decrease in the amount of the substrate or the increase in the amount of the reaction product with the test compound as compared to the amount of substrate or reaction product without the test compound identifies the test compound as an activator of aldolase activity. The increase in the amount of the substrate or the decrease in the amount of the reaction product with the test compound as compared to the amount of substrate or reaction product without the test compound identifies the test compound as an inhibitor of aldolase activity.

The invention provides computer systems comprising a processor and a data storage device wherein said data storage device has stored thereon a polypeptide sequence of the invention or a nucleic acid sequence of the invention.

In one aspect, the computer system can further comprise a sequence comparison algorithm and a data storage device having at least one reference sequence stored thereon. The sequence comparison algorithm can comprise a computer program that indicates polymorphisms. The computer system can further comprising an identifier that identifies one or more features in said sequence.

The invention provides computer readable mediums having stored thereon a sequence comprising a polypeptide sequence of the invention or a nucleic acid sequence of the invention.

The invention provides methods for identifying a feature in a sequence comprising the steps of: (a) reading the sequence using a computer program which identifies one or more features in a sequence, wherein the sequence comprises a polypeptide sequence of the invention or a nucleic acid sequence of the invention; and, (b) identifying one or more features in the sequence with the computer program.

The invention provides methods for comparing a first sequence to a second sequence comprising the steps of: (a) reading the first sequence and the second sequence through use of a computer program which compares sequences, wherein the first sequence comprises a polypeptide sequence of the invention or a nucleic acid sequence of the invention; and, (b) determining differences between the first sequence and the second sequence with the computer program. In one aspect, the step of determining differences between the first sequence and the second sequence further comprises the step of identifying polymorphisms. In one aspect, the method further comprises an identifier (and use of the identifier) that identifies one or more features in a sequence. In one aspect, the method comprises reading the first sequence using a computer program and identifying one or more features in the sequence.

The invention provides methods for isolating or recovering a nucleic acid encoding a polypeptide with an aldolase activity from an environmental sample comprising the steps of: (a) providing an amplification primer sequence pair for amplifying a nucleic acid encoding a polypeptide with an aldolase activity, wherein the primer pair is capable of amplifying a nucleic acid of the invention; (b) isolating a nucleic acid from the environmental sample or treating the environmental sample such that nucleic acid in the sample is accessible for hybridization to the amplification primer pair; and, (c) combining the nucleic acid of step (b) with the amplification primer pair of step (a) and amplifying nucleic acid from the environmental sample, thereby isolating or recovering a nucleic acid encoding a polypeptide with an aldolase activity from an environmental sample. In one aspect, each member of the amplification primer sequence pair comprises an oligonucleotide comprising at least about 10 to 50 consecutive bases of a nucleic acid sequence of the invention. In one aspect, the amplification primer sequence pair is an amplification pair of the invention.

The invention provides methods for isolating or recovering a nucleic acid encoding a polypeptide with an aldolase activity from an environmental sample comprising the steps of: (a) providing a polynucleotide probe comprising a nucleic acid sequence of the invention; (b) isolating a nucleic acid from the environmental sample or treating the environmental sample such that nucleic acid in the sample is accessible for hybridization to a polynucleotide probe of step (a); (c) combining the isolated nucleic acid or the treated environmental sample of step (b) with the polynucleotide probe of step (a); and, (d) isolating a nucleic acid that specifically hybridizes with the polynucleotide probe of step (a), thereby isolating or recovering a nucleic acid encoding a polypeptide with an aldolase activity from the environmental sample. In alternative aspects, the environmental sample comprises a water sample, a liquid sample, a soil sample, an air sample or a biological sample. In alternative aspects, the biological sample is derived from a bacterial cell, a protozoan cell, an insect cell, a yeast cell, a plant cell, a fungal cell or a mammalian cell.

The invention provides methods of generating a variant of a nucleic acid encoding an aldolase comprising the steps of: (a) providing a template nucleic acid comprising a nucleic acid of the invention; (b) modifying, deleting or adding one or more nucleotides in the template sequence, or a combination thereof, to generate a variant of the template nucleic acid.

In one aspect, the method further comprises expressing the variant nucleic acid to generate a variant aldolase polypeptide. In alternative aspects, the modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis (GSSM), synthetic ligation reassembly (SLR) and/or a combination thereof. In alternative aspects, the modifications, additions or deletions are introduced by a method selected from the group consisting of recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and/or a combination thereof.

In one aspect, the method is iteratively repeated until an aldolase having an altered or different activity or an altered or different stability from that of an aldolase encoded by the template nucleic acid is produced. In one aspect, the altered or different activity is an aldolase activity under an acidic condition, wherein the aldolase encoded by the template nucleic acid is not active under the acidic condition. In one aspect, the altered or different activity is an aldolase activity under a high temperature, wherein the aldolase encoded by the template nucleic acid is not active under the high temperature. In one aspect, the method is iteratively repeated until an aldolase coding sequence having an altered codon usage from that of the template nucleic acid is produced. The method can be iteratively repeated until an aldolase gene having higher or lower level of message expression or stability from that of the template nucleic acid is produced.

The invention provides methods for modifying codons in a nucleic acid encoding an aldolase to increase its expression in a host cell, the method comprising (a) providing a nucleic acid of the invention encoding an aldolase; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying codons in a nucleic acid encoding an aldolase, the method comprising (a) providing a nucleic acid of the invention encoding an aldolase; and, (b) identifying a codon in the nucleic acid of step (a) and replacing it with a different codon encoding the same amino acid as the replaced codon, thereby modifying codons in a nucleic acid encoding an aldolase.

The invention provides methods for modifying codons in a nucleic acid encoding an aldolase to increase its expression in a host cell, the method comprising (a) providing a nucleic acid of the invention encoding an aldolase; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying a codon in a nucleic acid encoding an aldolase to decrease its expression in a host cell, the method comprising (a) providing a nucleic acid of the invention encoding an aldolase; and, (b) identifying at least one preferred codon in the nucleic acid of step (a) and replacing it with a non-preferred or less preferred codon encoding the same amino acid as the replaced codon, wherein a preferred codon is a codon over-represented in coding sequences in genes in a host cell and a non-preferred or less preferred codon is a codon under-represented in coding sequences in genes in the host cell, thereby modifying the nucleic acid to decrease its expression in a host cell. In alternative aspects, the host cell is a bacterial cell, a fungal cell, an insect cell, a yeast cell, a plant cell or a mammalian cell.

The invention provides methods for producing a library of nucleic acids encoding a plurality of modified aldolase active sites or substrate binding sites, wherein the modified active sites or substrate binding sites are derived from a first nucleic acid comprising a sequence encoding a first active site or a first substrate binding site the method comprising: (a) providing a first nucleic acid encoding a first active site or first substrate binding site, wherein the first nucleic acid sequence comprises a nucleic acid of the invention; (b) providing a set of mutagenic oligonucleotides that encode naturally-occurring amino acid variants at a plurality of targeted codons in the first nucleic acid; and, (c) using the set of mutagenic oligonucleotides to generate a set of active site-encoding or substrate binding site-encoding variant nucleic acids encoding a range of amino acid variations at each amino acid codon that was mutagenized, thereby producing a library of nucleic acids encoding a plurality of modified aldolase active sites or substrate binding sites. In alternative aspects, the method comprises mutagenizing the first nucleic acid of step (a) by a method comprising an optimized directed evolution system, gene site-saturation mutagenesis (GSSM), and synthetic ligation reassembly (SLR). The method can further comprise mutagenizing the first nucleic acid of step (a) or variants by a method comprising error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis (GSSM), synthetic ligation reassembly (SLR) and a combination thereof. The method can further comprise mutagenizing the first nucleic acid of step (a) or variants by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

The invention provides methods for making a small molecule comprising the steps of: (a) providing a plurality of biosynthetic enzymes capable of synthesizing or modifying a small molecule, wherein one of the enzymes comprises an aldolase enzyme encoded by a nucleic acid of the invention; (b) providing a substrate for at least one of the enzymes of step (a); and, (c) reacting the substrate of step (b) with the enzymes under conditions that facilitate a plurality of biocatalytic reactions to generate a small molecule by a series of biocatalytic reactions.

The invention provides methods for modifying a small molecule comprising the steps: (a) providing an aldolase enzyme encoded by a nucleic acid of the invention; (b) providing a small molecule; and, (c) reacting the enzyme of step (a) with the small molecule of step (b) under conditions that facilitate an enzymatic reaction catalyzed by the aldolase enzyme, thereby modifying a small molecule by an aldolase enzymatic reaction. In one aspect, the method comprises providing a plurality of small molecule substrates for the enzyme of step (a), thereby generating a library of modified small molecules produced by at least one enzymatic reaction catalyzed by the aldolase enzyme. In one aspect, the method further comprises a plurality of additional enzymes under conditions that facilitate a plurality of biocatalytic reactions by the enzymes to form a library of modified small molecules produced by the plurality of enzymatic reactions. In one aspect, the method further comprises the step of testing the library to determine if a particular modified small molecule that exhibits a desired activity is present within the library. The step of testing the library can further comprises the steps of systematically eliminating all but one of the biocatalytic reactions used to produce a portion of the plurality of the modified small molecules within the library by testing the portion of the modified small molecule for the presence or absence of the particular modified small molecule with a desired activity, and identifying at least one specific biocatalytic reaction that produces the particular modified small molecule of desired activity.

The invention provides methods for determining a functional fragment of an aldolase enzyme comprising the steps of: (a) providing an aldolase enzyme comprising an amino acid sequence of the invention; and, (b) deleting a plurality of amino acid residues from the sequence of step (a) and testing the remaining subsequence for an aldolase activity, thereby determining a functional fragment of an aldolase enzyme. In one aspect, the aldolase activity is measured by providing an aldolase substrate and detecting an increase in the amount of the substrate or a decrease in the amount of a reaction product. In one aspect, a decrease in the amount of an enzyme substrate or an increase in the amount of the reaction product with the test compound as compared to the amount of substrate or reaction product without the test compound identifies the test compound as an activator of aldolase activity.

The invention provides methods for whole cell engineering of new or modified phenotypes by using real-time metabolic flux analysis, the method comprising the following steps: (a) making a modified cell by modifying the genetic composition of a cell, wherein the genetic composition is modified by addition to the cell of a nucleic acid of the invention; (b) culturing the modified cell to generate a plurality of modified cells; (c) measuring at least one metabolic parameter of the cell by monitoring the cell culture of step (b) in real time; and, (d) analyzing the data of step (c) to determine if the measured parameter differs from a comparable measurement in an unmodified cell under similar conditions, thereby identifying an engineered phenotype in the cell using real-time metabolic flux analysis. In one aspect, the genetic composition of the cell can be modified by a method comprising deletion of a sequence or modification of a sequence in the cell, or, knocking out the expression of a gene. In one aspect, the method can further comprise selecting a cell comprising a newly engineered phenotype. In another aspect, the method can comprise culturing the selected cell, thereby generating a new cell strain comprising a newly engineered phenotype.

The invention provides methods of increasing thermotolerance or thermostability of an aldolase polypeptide, the method comprising glycosylating an aldolase polypeptide, wherein the polypeptide comprises at least thirty contiguous amino acids of a polypeptide of the invention; or a polypeptide encoded by a nucleic acid sequence of the invention, thereby increasing the thermotolerance or thermostability of the aldolase polypeptide. In one aspect, the aldolase specific activity can be thermostable or thermotolerant at a temperature in the range from greater than about 37° C. to about 95° C.

The invention provides methods for overexpressing a recombinant aldolase polypeptide in a cell comprising expressing a vector comprising a nucleic acid comprising a nucleic acid of the invention or a nucleic acid sequence of the invention, wherein the sequence identities are determined by analysis with a sequence comparison algorithm or by visual inspection, wherein overexpression is effected by use of a high activity promoter, a dicistronic vector or by gene amplification of the vector.

The invention provides methods of making a transgenic plant comprising the following steps: (a) introducing a heterologous nucleic acid sequence into the cell, wherein the heterologous nucleic sequence comprises a nucleic acid sequence of the invention, thereby producing a transformed plant cell; and (b) producing a transgenic plant from the transformed cell. In one aspect, the step (a) can further comprise introducing the heterologous nucleic acid sequence by electroporation or microinjection of plant cell protoplasts. In another aspect, the step (a) can further comprise introducing the heterologous nucleic acid sequence directly to plant tissue by DNA particle bombardment. Alternatively, the step (a) can further comprise introducing the heterologous nucleic acid sequence into the plant cell DNA using an *Agrobacterium tumefaciens* host. In one aspect, the plant cell can be a potato, corn, rice, wheat, tobacco, or barley cell.

The invention provides methods of expressing a heterologous nucleic acid sequence in a plant cell comprising the following steps: (a) transforming the plant cell with a heterologous nucleic acid sequence operably linked to a promoter, wherein the heterologous nucleic sequence comprises a nucleic acid of the invention; (b) growing the plant under conditions wherein the heterologous nucleic acids sequence is expressed in the plant cell. The invention provides methods of expressing a heterologous nucleic acid sequence in a plant cell comprising the following steps: (a) transforming the plant cell with a heterologous nucleic acid sequence operably linked to a promoter, wherein the heterologous nucleic sequence comprises a sequence of the invention; (b) growing the plant under conditions wherein the heterologous nucleic acids sequence is expressed in the plant cell.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

DESCRIPTION OF DRAWINGS

Like reference symbols in the various drawings indicate like elements.

DETAILED DESCRIPTION

Figure 5:
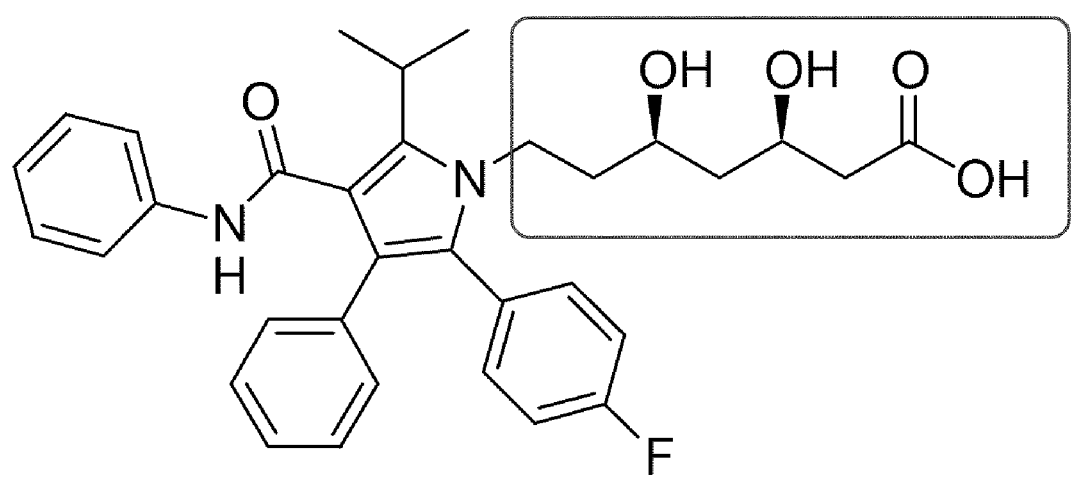
FIG. 5 illustrates the chemical formula of [R—(R*,R*)]-2-(4-fluorophenyl)-b,d-dihydroxy-5-(1-methylethyl)-3-phenyl-4-(phenylamino)-carbonyl]-1H-pyrrole-1-heptanoic acid, or, atorvastatin (LIPITOR™), as described in detail, below.
Figure 6:
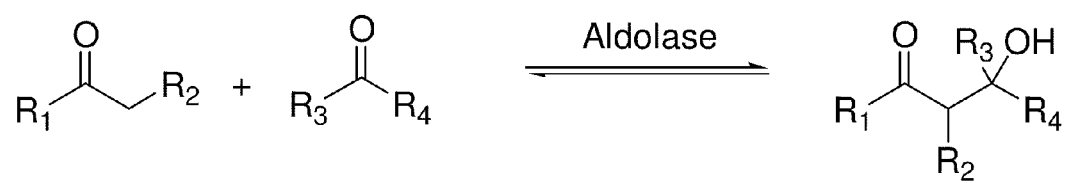
FIG. 6 is a schematic representation of an aldol reaction catalyzed by an aldolase, as described in detail, below.
Figure 19:
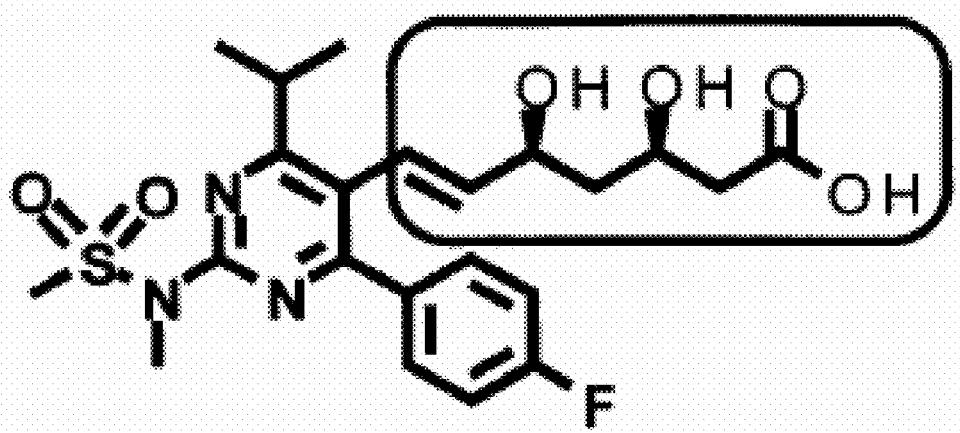
FIG. 19 illustrates the structure of rosuvastatin (CRESTOR™).
Figure 20:
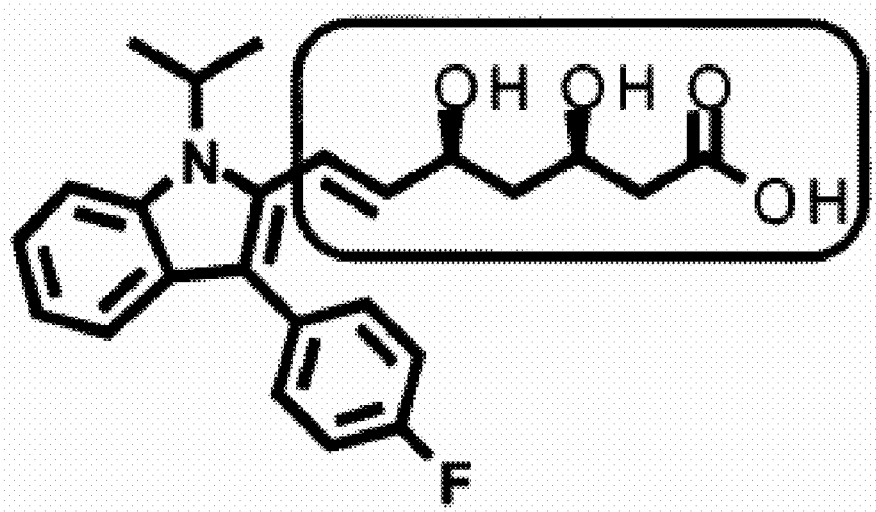
FIG. 20 illustrates the structure of fluvastatin (LESCOL™).

The present invention provides chemoenzymatic methods for the synthesis of chiral β,δ-dihydroxyheptanoic acid side chains, [R—(R*,R*)]-2-(4-fluorophenyl)-b,d-dihydroxy-5-(1-methylethyl)-3-phenyl-4-(phenylamino)-carbonyl]-1H-pyrrole-1-heptanoic acid (atorvastatin, LIPITOR™) (FIG. 5), rosuvastatin (CRESTOR™) (FIG. 19), fluvastatin (LESCOL™) (FIG. 20), related compounds and their intermediates.

The invention also provides intermediates of atorvastatin, rosuvastatin and related compounds having a chiral β,δ-dihydroxyheptanoic acid side chain, and methods of making them.

The chemoenzymatic methods of the invention can use any polypeptide having an aldolase activity (e.g., an enzyme, a catalytic antibody), e.g., SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, including a polypeptide of the invention having an aldolase activity, e.g., the exemplary SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, or, a polypeptide encoded by a nucleic acid as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29.

The invention provides enantioselective syntheses of various compounds by using an aldolase in enzymatic aldol condensation. The aldolase can be any aldolase, or, an aldolase of the invention (e.g., the exemplary SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30).

The polypeptides of the invention can have any aldolase or lyase activity. The enzymes of the invention can have the activity of any aldolase, which are part of a large group of enzymes called lyases and are present in all organisms. The function of aldolases in vivo is often related to the degradative cleavage of metabolites. For example, the aldolases of the invention can catalyze C—C bond formation, and, in one aspect, in a highly stereoselective way. As another example, a polypeptide of the invention can have a 2-deoxyribose-5-phosphate aldolase (DERA) activity, which can comprise catalysis of the reversible aldol reaction between acetaldehyde and D-glyceraldehyde-3-phosphate to generate D-2-deoxyribose-5-phosphate. DERA aldolase activity of the invention can catalyze the reversible asymmetric aldol addition reaction of two aldehydes. Further exemplary activities of polypeptides of the invention are described, below.

One aspect of the invention uses a 2-deoxyribose-5-phosphate aldolase (DERA) in a process to prepare a chiral β,δ-dihydroxyheptanoic acid side chain. A DERA of the invention can assemble a statin side chain, e.g., an atorvastatin (LIPITOR™) and/or a rosuvastatin (CRESTOR™) side chain and/or a fluvastatin (LESCOL™) side chain, including the setting of one or both stereogenic centers; which, in one aspect, can be in a single transformation. Low-cost starting materials can be used. As noted above, any polypeptide having an aldolase activity (e.g., an enzyme, a catalytic antibody, as, e.g., described in U.S. Pat. No. 6,368,839), e.g., including the exemplary aldolases of the invention SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30, or enzymatically active fragments thereof, can be used.

Figure 7:
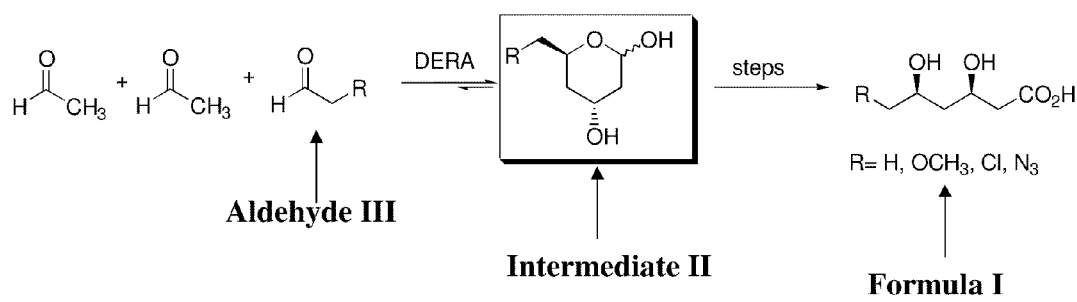
FIG. 7 is a schematic representation of a DERA-catalyzed aldol synthesis of a side chain intermediate used, e.g., in the production of [R—(R*,R*)]-2-(4-fluorophenyl)-b,d-dihydroxy-5-(1-methylethyl)-3-phenyl-4-(phenylamino)-carbonyl]-1H-pyrrole-1-heptanoic acid (atorvastatin, or LIPITOR™) or rosuvastatin (CRESTOR™), as described in detail, below.

One aspect of this invention provides a DERA-catalyzed synthesis of an intermediate of formula II from an acetaldehyde and the aldehyde of formula III, as illustrated in FIG. 7. In intermediate II and aldehyde III the R group can be a hydrogen, an alkyl group, an alkoxy group, a halogen (e.g., a chlorine) or an azido group.

The term "alkoxy", as used herein alone or as part of another group, denotes an alkyl group bonded through an oxygen linkage (—O—). The term "alkyl", as used herein alone or as part of another group, denotes optionally substituted, straight and branched chain saturated hydrocarbon groups, in one aspect having 1 to 12 carbons in the normal chain. Exemplary unsubstituted such groups include methyl, ethyl, propyl, isopropyl, n-butyl, isobutyl, hexyl, isohexyl, heptyl, 4,4-dimethylpentyl, octyl, and the like. Exemplary substituents may include the following groups: halo, alkoxy, alkylthio, alkenyl, alkynyl, aryl, cycloalkyl, cycloalkenyl, hydroxy or protected hydroxy, carboxyl, alkyloxycarbonyl, amino, mono- or dialkylamino or thiol. The term "halogen" or "halo", as used herein alone or as part of another group, denotes chlorine, bromine, iodine, and fluorine. The term azido, as used herein alone or as part of another group, denotes an $N_3$ group. The term cyano, as used herein alone or as part of another group, denotes an —C≡N group.

In one aspect, as illustrated in FIG. 7, the aldehyde of formula III is admixed with acetaldehyde and DERA in an aqueous medium to form a reaction mixture. In one aspect, the reaction mixture is maintained at a particular pH value and temperature for a time period sufficient for the intermediate II to form and be recovered. In this reaction acetaldehyde is a donor substrate and the aldehyde III is the acceptor substrate. In one aspect, the acetaldehyde is in stoichiometric excess over the acceptor. In one aspect, the ratio of donor to acceptor can be about 1.5:1 to about 5:1 on a molar basis. In another aspect, the ratio of donor to acceptor can be about 2.5:1 to about 4:1. In one aspect, the pH value of the reaction mixture can be between about pH 6.5 and about pH 8.5. In one aspect, the pH of the initially formed reaction mixture stays the same throughout the course of the reaction.

In one aspect, the reaction is carried out in the absence of light. The components can be admixed in the light, and the resulting reaction mixture can be shielded from the light. The process can be carried out in the absence of oxygen. In one aspect, the reaction can be carried out in an atmosphere of nitrogen, argon or a similar gas. See, for example, U.S. Pat. No. 5,795,749.

Figure 1:
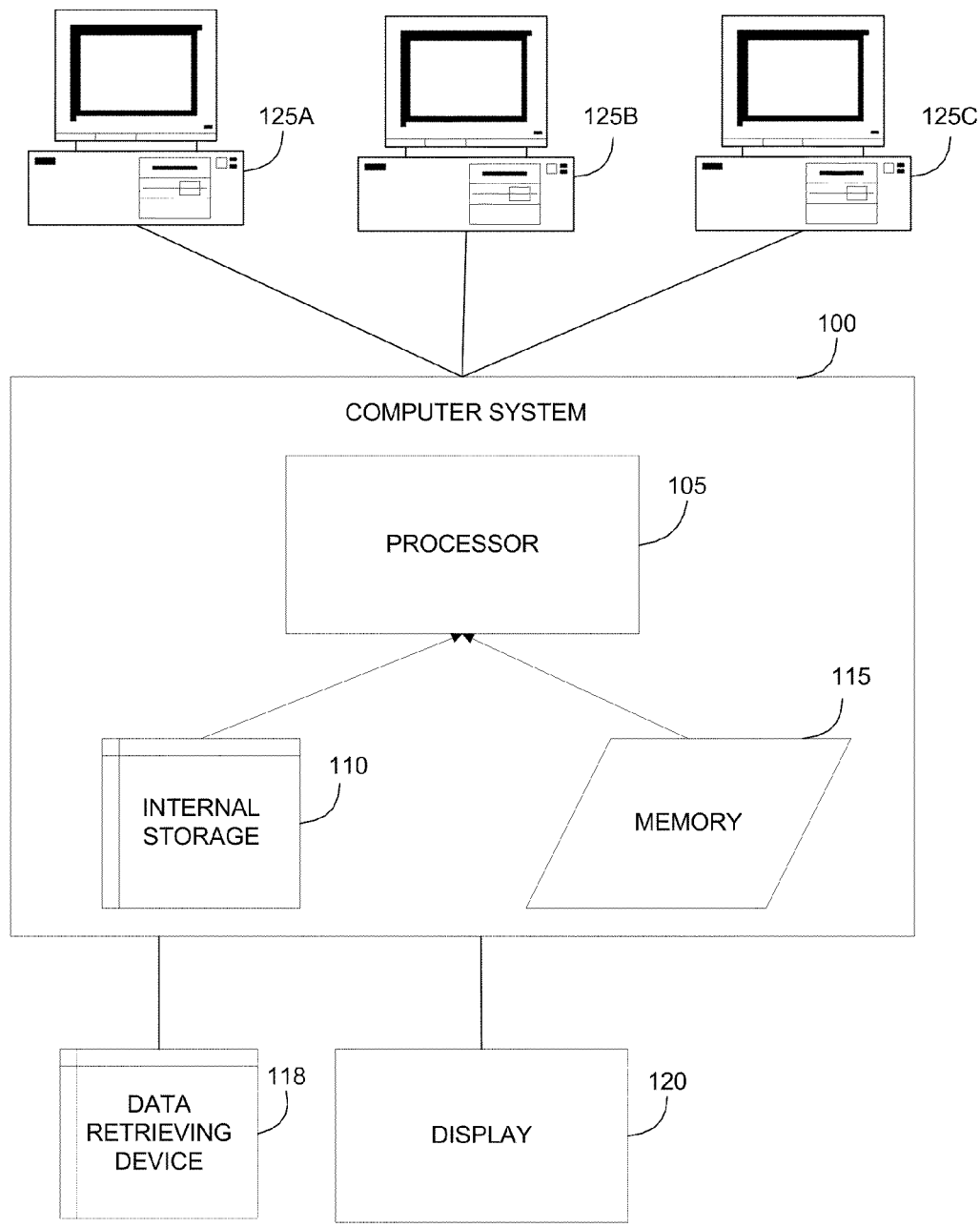
FIG. 1 is a block diagram of a computer system.
Figure 8:
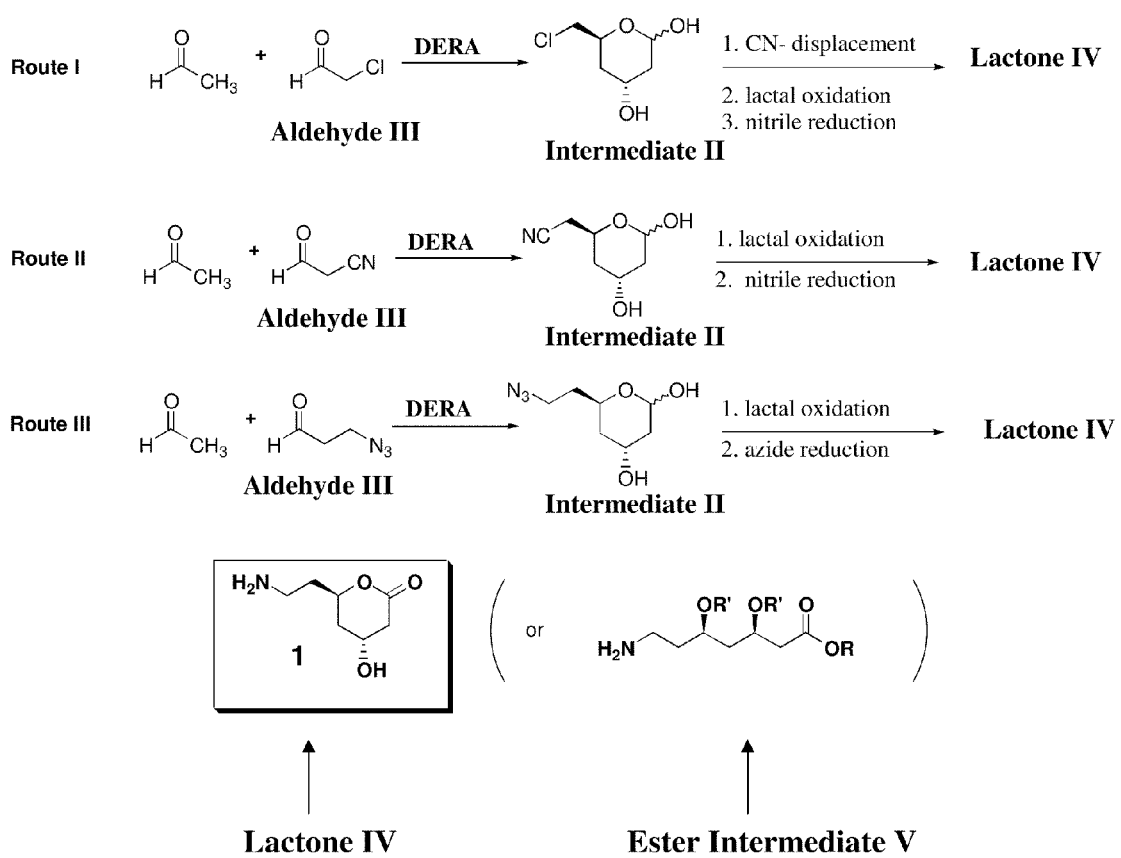
FIG. 8 illustrates exemplary schemes for DERA-catalyzed production of atorvastatin (LIPITOR™) or rosuvastatin (CRESTOR™) side chains, as described in detail, below.

Alternative exemplary processes are illustrated in FIG. 8. The intermediate of formula II can be converted through several chemical transformations to a lactone (IV), which in turn can serve as the intermediate for the production of Atorvastatin (see formula XI, FIG. 11, and FIG. 1). Alternatively, a ring-open ester intermediate of the formula V (FIG. 8) can be prepared.

Route I (FIG. 8) exemplifies one aspect of this invention, wherein aldehyde is used as the donor and an aldehyde of formula III (FIG. 7 or 8), wherein R is halogen (e.g., R is a chlorine, see aldehyde of formula III, FIG. 7), used as the aldehyde receptor in the aldolase enzyme reaction. In one aspect, the aldehyde of formula III can be chloroacetaldehyde. An advantage of this exemplary approach may be that both starting aldehyde materials are low cost and readily available. In one aspect, the invention provides a DERA enzyme catalyzing this reaction with high efficiency.

In alternative aspects, the second step of the transformation in this route can involve oxidation of the intermediate of formula (Intermediate) II to a lactone IV (FIG. 8). See Routes I, II and III of FIG. 8. In one aspect, this transformation can be performed on the unpurified crude product (intermediate of formula II) from the DERA-catalyzed reaction.

As illustrated in FIG. 8, in exemplary Route I, the synthesis of a chloro lactone IV from halogenated intermediate II can comprise CN— displacement, lactal oxidation and nitrile reduction. In another aspect, in exemplary Route II, the synthesis of a cyano lactone IV from a cyano intermediate II can comprise lactal oxidation and nitrile reduction. In another aspect, in exemplary Route III, the synthesis of a nitrile lactone IV from a nitrile intermediate II can comprise lactal oxidation and azide reduction.

Figure 9:
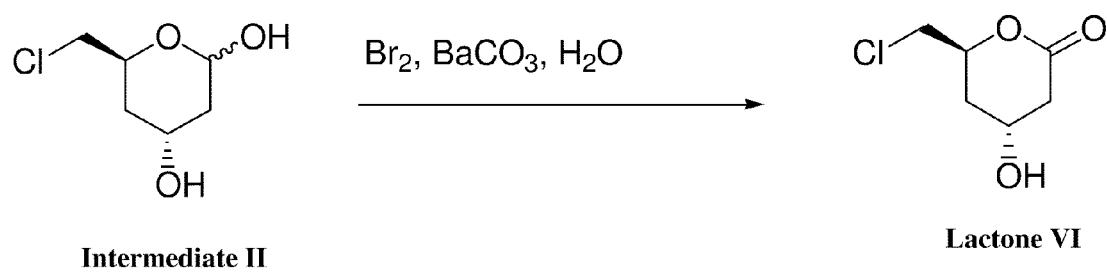
FIG. 9 is a schematic representation of an exemplary oxidation (a bromine/barium carbonate oxidation) of the DERA-catalyzed intermediate to a chloro lactone, as described in detail, below.

In one aspect, as illustrated in FIG. 9, the product 6-chloro-2,4,6-trideoxyerythro-hexonolactone (chloro-lactone VI) is crystalline and can be purified from the crude mixture by recrystallization. In one aspect, this transformation can be carried out under oxidation conditions comprising bromine ($Br_2$), $BrCO_3$ and water. In one aspect, the oxidation conditions comprise sodium hypochlorite (NaOCl) in acetic acid (HOAc) and water The 6-chloro-2,4,6-trideoxyerythro-hexonolactone (chloro-lactone VI) can be converted to the final protected side chain intermediate in a number of ways, as illustrated in FIG. 10, Routes A, B, and C.

Figure 10:
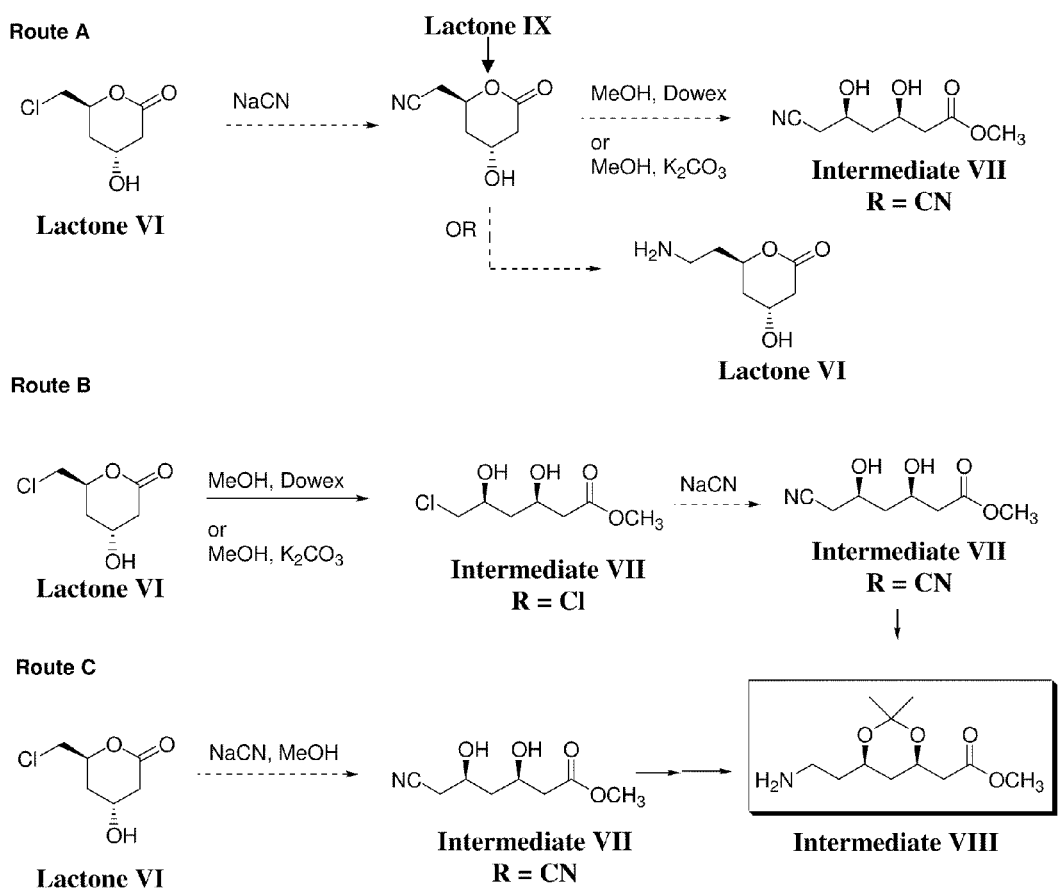
FIG. 10 illustrates exemplary synthesis options starting from the lactone VI to the atorvastatin (LIPITOR™) or rosuvastatin (CRESTOR™) side chain, as described in detail, below.

One exemplary route entails cyanide displacement of chloride on the chlorinated lactone VI (FIG. 10, Route A). In one aspect, NaCN is used for cyanide displacement. This can be followed by ring opening or by carrying the halogenated lactone IV through to the end of synthesis. The advantage of keeping the lactone IV intact is that it may obviate the need for protection and deprotection steps. The ring can be opened by treating the cyano lactone IX with MeOH/Dowex or MeOH/$K_2CO_3$ to synthesize a cyano intermediate VII. Alternatively, the cyano lactone IX (FIG. 10, Route A) can be converted to an aminated ($H_2N$—) lactone IV.

Alternatively, as illustrated in Route B, FIG. 10, the cyanide displacement can be performed on an open-chain intermediate. The ring can be opened by treating the lactone IX with MeOH/Dowex or MeOH/$K_2CO_3$ resulting in the formation of a chlorinated intermediate VII. NaCN can be used for cyanide displacement. The product is a cyano intermediate VII (which can be processed to intermediate VIII).

In another aspect, the ring opening can be achieved by treating the halogenated lactone VI with MeOH/NaCN to obtain a cyano ester intermediate VII (Route C, FIG. 10). Route C can cut a step from the process by allowing the lactone opening and the cyanide displacement to occur in one pot. The cyano ester intermediate VII can be processed to intermediate VIII. In one aspect, the process can utilize a tert-butyl ester rather than a methyl ester. If necessary, a transesterification can be performed to convert the methyl ester to the tert-butyl ester.

Figure 11:
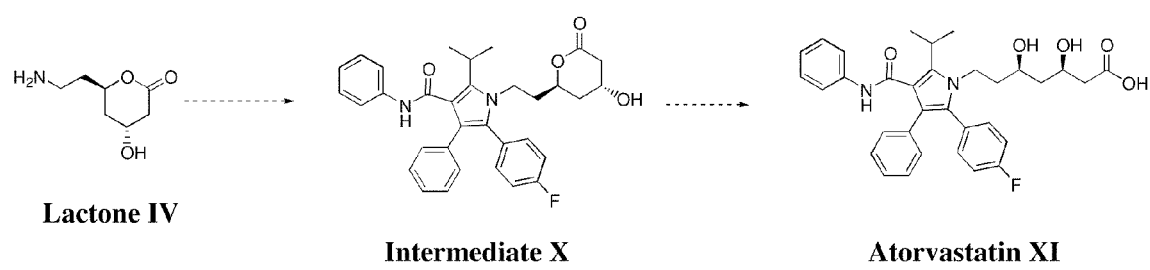
FIG. 11 is a schematic representation of an exemplary complete [R—(R*,R*)]-2-(4-fluorophenyl)-b,d-dihydroxy-5-(1-methylethyl)-3-phenyl-4-(phenylamino)-carbonyl]-1H-pyrrole-1-heptanoic acid (atorvastatin, LIPITOR™) synthesis of the invention, with the intact lactone intermediate, as described in detail, below.

As illustrated in FIG. 11, the invention provides an alternative synthetic route starting from an intact chloro lactone intermediate IV, wherein IV is converted to the intermediate X, which in turn is converted to (R)-Ethyl-4-Cyano-3-Hydroxybutyrate, or, Atorvastatin (LIPITOR™) XI.

Figure 12:
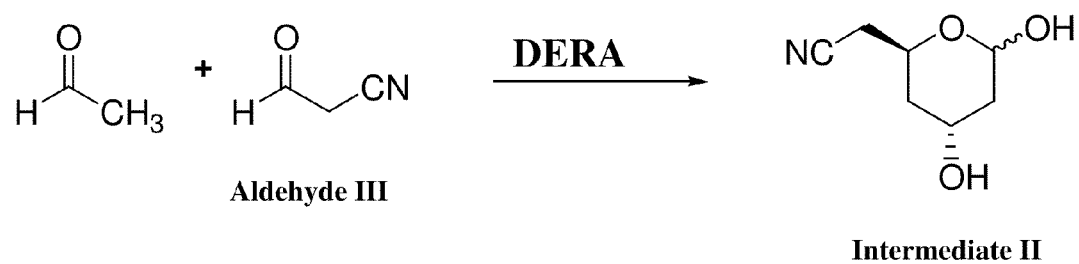
FIG. 12 illustrates the exemplary Route II DERA-catalyzed reaction of the invention, as described in detail, below.

In FIG. 8, exemplary Route II occurs in one step by omitting the cyanide displacement step after the post-enzymatic process (see also FIG. 12). The aldehyde of formula III (wherein R is a cyano group) is not commercially available. The same cyano-lactone (lactone IV) or cyano open chain intermediates (ester intermediate V) as above in FIG. 10) are accessible from the cyano lactal intermediate II of FIG. 12.

Figure 13:
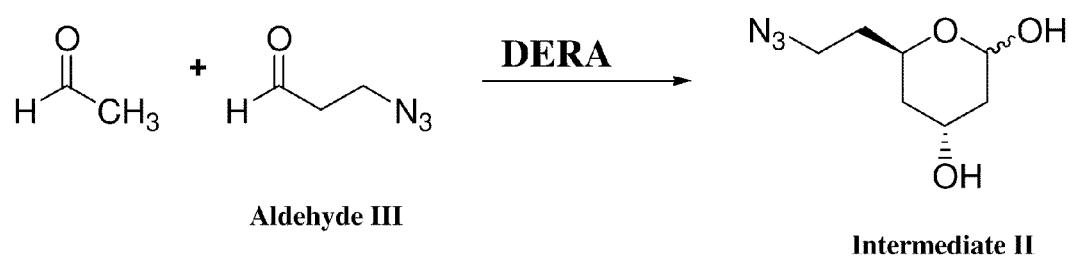
FIG. 13 is a schematic representation of the exemplary Route III DERA-catalyzed reaction of the invention, as described in detail, below.

In FIG. 8, exemplary route III also can occur one step by omitting the cyanide displacement step after the post-enzymatic process (see also FIG. 13). However, the starting material azido aldehyde (the aldehyde of formula III wherein R is $N_3$ has to be synthesized. From the azido lactal product (intermediate II), the same alternative routes are accessible as described above, wherein both lactone IV and open-chain ester intermediate V can be developed.

Figure 17:
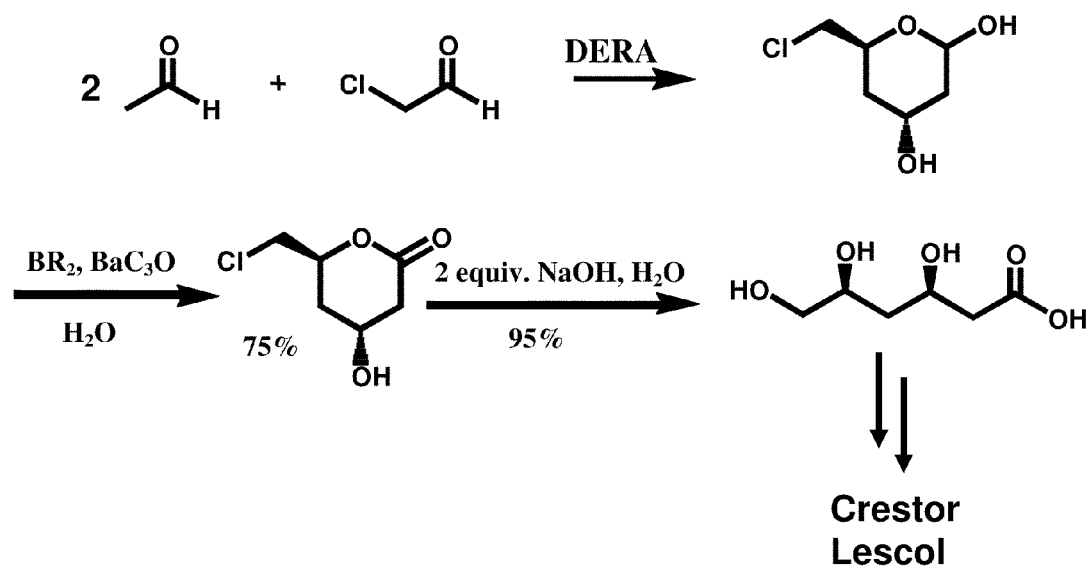
FIG. 17 illustrates an exemplary process for making 6-chloro-2,4,6-trideoxyerythro-hexonolactone, and, rosuvastatin (CRESTOR™) and fluvastatin (LESCOL™), and their various intermediates, using a DERA.
Figure 18:
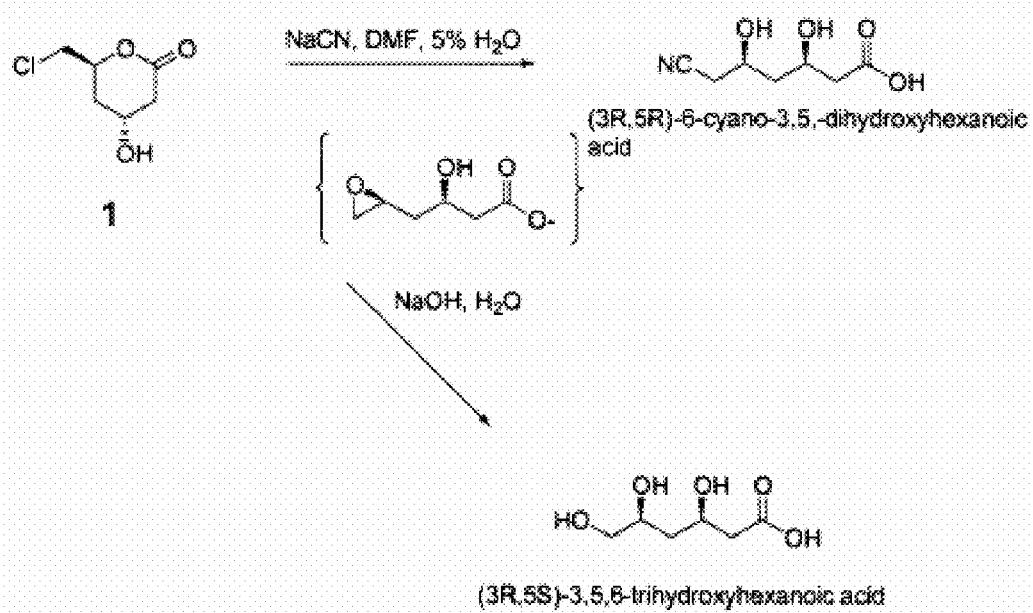
FIG. 18 illustrates an exemplary process for making 6-chloro-2,4,6-trideoxyerythro-hexonolactone, [R—(R*,R*)]-2-(4-fluorophenyl)-b,d-dihydroxy-5-(1-methylethyl)-3-phenyl-4-(phenylamino)-carbonyl]-1H-pyrrole-1-heptanoic acid (atorvastatin, LIPITOR™), and their various intermediates, using a DERA.

The invention also provides a novel methodologies for the synthesis of statin intermediates using a deoxyribose-5-phosphate aldolase (DERA), which can be an enzyme of the invention. In one aspect, the invention provides for the conversion of Compound I of FIG. 14 to intermediates for the synthesis of statin intermediates, including atorvastatin (LIPITOR™) and rosuvastatin (CRESTOR™), by ring-opening and nucleophilic displacement with cyanide or hydroxide, respectively. The invention provides a process as set forth in FIG. 14. In one aspect, the method comprises use of NaCN (e.g., at 3 equivalents), DMF, and water (e.g., 5% $H_2O$). In one aspect, this reaction is run under conditions comprising about 40° C. and/or about 20 hours. In one aspect, the invention provides a process wherein the lactone 3R,5S-6-chloro-2,4,6-trideoxy-erythro-hexonolactone (Compound I of FIG. 14) is made by a 2-step process integrating a biocatalytic step using deoxyribose-5-phosphate aldolase (DERA), e.g., an aldolase of the invention, with a chemical oxidation step. The lactone 3R,5S-6-chloro-2,4,6-trideoxy-erythro-hexonolactone (compound I of FIG. 14) can readily be converted into side-chain intermediates for the synthesis of a variety of statin-type HMG-CoA reductase inhibitors, including atorvastatin (LIPITOR™), rosuvastatin (CRESTOR™), and fluvastatin (LESCOL™), see FIG. 14, FIG. 17 and FIG. 18.

In one aspect, the processes of the invention provide a significant improvement in enzyme load and yield for DERAs by running a fed-batch reaction to gradually add the substrates acetaldehyde and chloroacetaldehyde to the enzyme.

A serious limitation to the DERA process as originally described in the literature was the requirement of a high percentage of catalyst (enzyme load). For instance, to produce 10 grams of 3R,5S-6-chloro-2,4,6-trideoxy-erythro-hexose, about 2 grams of DERA was required (20% enzyme load). The cause of the high enzyme requirement was identified to be inhibition by the substrate chloroacetaldehyde. The invention provides processes for overcoming this requirement by using a fed-batch process. In one aspect, substrates are fed into the reaction over a several hour period, e.g., a 2 to 3 hour period (e.g., at room temperature) at a rate such that they are consumed as fast as they are added, and chloroacetaldehyde does not reach inhibitory concentration. Under these conditions, enzyme load for *E. coli* DERA was reduced from about 20% to about 5%. This improvement also applies to any DERA, including the exemplary polypeptides of the invention, e.g., SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30, or enzymatically active fragments thereof. In one aspect, the process is carried out in the range of 2 to 4% enzyme load. Substrates are fed to a final concentration of about 600 to 800 mM chloroacetaldehyde and about 1.2 to 1.6 M acetaldehyde. The reaction can be run on a large scale, e.g., a 1-liter (or greater) scale, with isolation of 75 grams crude product.

The published procedure for oxidation of a lactol to a lactone, e.g., the lactone 3R,5S-6-chloro-2,4,6-trideoxy-erythro-hexonolactone (compound I of FIG. 14), uses bromine as the oxidant in the presence of barium carbonate and water. While this method is effective, the cost and toxicity of bromine are issues for process scale. The invention provides a novel process wherein this oxidation can be performed in the same yield with inexpensive sodium hypochlorite (bleach) in acetic acid, as illustrated in FIG. 15. In one aspect, the substrate is dissolved in glacial acetic acid at a concentration of 750 mM, and 1 equivalent of aqueous sodium hypochlorite is fed into the solution over 3 hours, at room temperature. 75 grams of crude lactol was converted to 40 grams of pure 3R,5S-6-chloro-2,4,6-trideoxy-erythro-hexonolactone (compound I of FIG. 14) by this process. FIG. 15 illustrates the oxidation of crude chlorolactol to crystalline chlorolactone with sodium hypochlorite.

Figure 16:
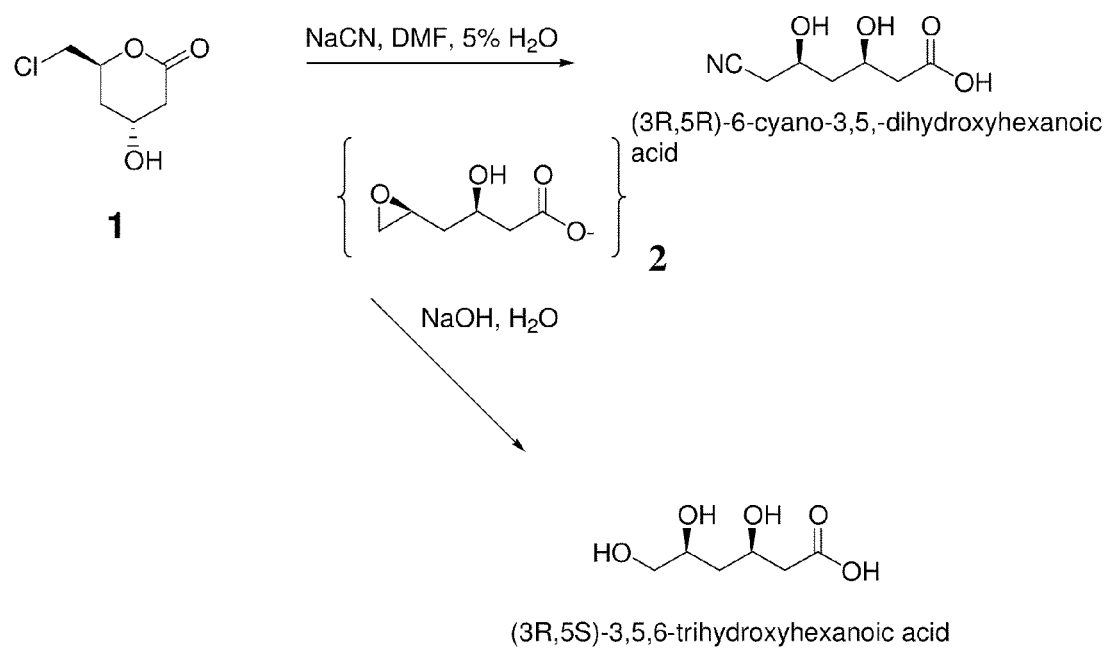
FIG. 16 illustrates an exemplary single step process for converting the lactone 3R,5S-6-chloro-2,4,6-trideoxy-erythro-hexonolactone to either (3R,5S)-3,5,6-trihydroxy-hexanoic acid or (3R,5R)-6-cyano-3,5,-dihydroxyhexanoic acid, as described in detail, below.

In one aspect, the lactone 3R,5S-6-chloro-2,4,6-trideoxy-erythro-hexonolactone (compound I of FIG. 14, see also FIG. 17, FIG. 18) is converted in a single step to either (3R,5S)-3,5,6-trihydroxyhexanoic acid or (3R,5R)-6-cyano-3,5,-dihydroxyhexanoic acid (FIG. 16). The former compound can be converted to rosuvastatin (CRESTOR™), fluvastatin (LESCOL™) and other statins, whereas the cyano compound can be converted to atorvastatin (LIPITOR™). Both methods go through a common intermediate, the epoxide (-(3R,5S-3-hydroxy-4-oxiranylbutyric acid sodium salt) shown in brackets in FIG. 16. See Example 2, below.

General Methods

The present invention provides novel biochemical processes for the production of chiral β,δ-dihydroxyheptanoic acid side chains, including statins, and compositions comprising these side chains, e.g., [R—(R*,R*)]-2-(4-fluorophenyl)-b,d-dihydroxy-5-(1-methylethyl)-3-phenyl-4-(phenylamino)-carbonyl]-1H-pyrrole-1-heptanoic acid (atorvastatin, LIPITOR™), rosuvastatin (CRESTOR™), fluvastatin (LESCOL™) related compounds and various intermediates. The invention also provides novel aldolases, which, in one aspect, can be used to practice the methods of the invention. The skilled artisan will recognize that the starting and intermediate compounds used in the methods of the invention can be synthesized using a variety of procedures and methodologies, which are well described in the scientific and patent literature, e.g., Organic Syntheses Collective Volumes, Gilman et al. (Eds) John Wiley & Sons, Inc., NY; Venuti (1989) *Pharm Res.* 6:867-873. The invention can be practiced in conjunction with any method or protocol known in the art, which are well described in the scientific and patent literature. Enzymes of the invention, and the enzymes used in the methods of the invention, can be produced by any synthetic or recombinant method, or, they may be isolated from a natural source, or, a combination thereof.

The nucleic acids and proteins of the invention can be detected, confirmed and quantified by any of a number of means well known to those of skill in the art. General methods for detecting both nucleic acids and corresponding proteins include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELI- SAs), immunofluorescent assays, and the like. The detection of nucleic acids can be by well known methods such as Southern analysis, northern analysis, gel electrophoresis, PCR, radiolabeling, scintillation counting, and affinity chromatography.

The discussion of the general methods given herein is intended for illustrative purposes only. Other alternative methods and embodiments will be apparent to those of skill in the art upon review of this disclosure.

Generating and Manipulating Nucleic Acids

The invention provides isolated, synthetic or recombinant nucleic acids (e.g., the exemplary SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 and SEQ ID NO:29; or nucleic acids encoding the polypeptides of the invention, e.g., SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30, or enzymatically active fragments thereof). In one aspect, the nucleic acids encode a polypeptide having an aldolase activity.

Nucleic acids encoding aldolases of the invention, and enzymes used to practice the methods of the invention, whether RNA, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems. Nucleic acids used to practice the methods of the invention, and to make the polynucleotides and polypeptide of the invention, can be generated using amplification methods, which are also well known in the art, and include, e.g., polymerase chain reaction, PCR (see, e.g., PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y, ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477-1491), automated Q-beta replicase amplification assay (see, e.g., Burg (1996) Mol. Cell. Probes 10:257-271) and other RNA polymerase mediated techniques (e.g., NASBA, Cangene, Mississauga, Ontario).

Alternatively, these nucleic acids can be synthesized in vitro by well-known chemical synthesis techniques, as described in, e.g., Adams (1983) J. Am. Chem. Soc. 105:661; Belousov (1997) Nucleic Acids Res. 25:3440 3444; Frenkel (1995) Free Radic. Biol. Med. 19:373 380; Blommers (1994) Biochemistry 33:7886 7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y (1993). Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

Another useful means of obtaining and manipulating nucleic acids of the invention, or nucleic acids used to practice the methods of the invention, is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

Transcriptional and Translational Control Sequences

The invention provides nucleic acid (e.g., DNA) sequences of the invention operatively linked to expression (e.g., transcriptional or translational) control sequence(s), e.g., promoters or enhancers, to direct or modulate RNA synthesis/expression. The expression control sequence can be in an expression vector. Exemplary bacterial promoters include lacI, lacZ, T3, T7, gpt, lambda PR, PL and trp. Exemplary eukaryotic promoters include CMV immediate early, HSV thymidine kinase, early and late SV40, LTRs from retrovirus, and mouse metallothionein I.

Promoters suitable for expressing a polypeptide in bacteria include the E. coli lac or trp promoters, the lacI promoter, the lacZ promoter, the T3 promoter, the T7 promoter, the gpt promoter, the lambda PR promoter, the lambda PL promoter, promoters from operons encoding glycolytic enzymes such as 3-phosphoglycerate kinase (PGK), and the acid phosphatase promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Expression Vectors and Cloning Vehicles

The invention provides expression vectors and cloning vehicles comprising nucleic acids of the invention, e.g., sequences encoding the aldolases of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors of the invention can include chromosomal, non-chromosomal and synthetic DNA sequences. Large numbers of suitable vectors are known to those of skill in the art, and are commercially available. Exemplary vectors are include: bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present invention.

The expression vector may comprise a promoter, a ribosome-binding site for translation initiation and a transcription terminator. The vector may also include appropriate sequences for amplifying expression. Mammalian expression vectors can comprise an origin of replication, any necessary ribosome binding sites, a polyadenylation site, splice donor and acceptor sites, transcriptional termination sequences, and 5' flanking non-transcribed sequences. In some aspects, DNA sequences derived from the SV40 splice and polyadenylation sites may be used to provide the required non-transcribed genetic elements.

In one aspect, the expression vectors contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in *E. coli*, and the *S. cerevisiae* TRP1 gene. Promoter regions can be selected from any desired gene using chloramphenicol transferase (CAT) vectors or other vectors with selectable markers.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers.

A DNA sequence may be inserted into a vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are known in the art, e.g., as described in Ausubel and Sambrook. Such procedures and others are deemed to be within the scope of those skilled in the art.

The vector may be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook.

Particular bacterial vectors which may be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, pDR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

Host Cells and Transformed Cells

The invention also provides a transformed cell comprising a nucleic acid sequence of the invention, e.g., a sequence encoding an aldolase of the invention, a vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Salmonella typhimurium* and various species within the genera *Pseudomonas, Streptomyces*, and *Staphylococcus*. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation; see, e.g., Davis, L., Dibner, M., Battey, I., Basic Methods in Molecular Biology, (1986).

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in E. coli.

Amplification of Nucleic Acids

In practicing the invention, nucleic acids encoding the polypeptides of the invention, or modified nucleic acids, can be reproduced by, e.g., amplification. The invention provides amplification primer sequence pairs for amplifying nucleic acids encoding polypeptides with an aldolase activity. In one aspect, the primer pairs are capable of amplifying nucleic acid sequences of the invention, e.g., including the exemplary SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or subsequences thereof, nucleic acids encoding SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30, or enzymatically active fragments thereof, or subsequences thereof, etc. One of skill in the art can design amplification primer sequence pairs for any part of or the full length of these sequences.

The invention provides an amplification primer sequence pair for amplifying a nucleic acid encoding a polypeptide having an aldolase activity, wherein the primer pair is capable of amplifying a nucleic acid comprising a sequence of the invention, or fragments or subsequences thereof. In alternative aspects, one or each member of the amplification primer sequence pair can comprise an oligonucleotide comprising at least about 10 to 50 consecutive bases of a sequence of the invention, or about 12, 13, 14, 15, 16, 17, 18, 19, 20, 21, 22, 23, 24, 25, 26, 27, 28, 29, 30 or more consecutive bases of a sequence of the invention. The invention provides amplification primer pairs, wherein the primer pair comprises a first member having a sequence as set forth by about the first (the 5') 12, 13, 14, 15, 16, 17, 18, 19, 20, 21, 22, 23, 24, 25, 26, 27, 28, 29, 30 or more residues of a nucleic acid of the invention, and a second member having a sequence as set forth by about the first (the 5') 12, 13, 14, 15, 16, 17, 18, 19, 20, 21, 22, 23, 24, 25, 26, 27, 28, 29, 30 or more residues of the complementary strand of the first member. The invention provides aldolases generated by amplification, e.g., polymerase chain reaction (PCR), using an amplification primer pair of the invention. The invention provides methods of making an aldolase by amplification, e.g., polymerase chain reaction (PCR), using an amplification primer pair of the invention. In one aspect, the amplification primer pair amplifies a nucleic acid from a library, e.g., a gene library, such as an environmental library.

Amplification reactions can also be used to quantify the amount of nucleic acid in a sample (such as the amount of message in a cell sample), label the nucleic acid (e.g., to apply it to an array or a blot), detect the nucleic acid, or quantify the amount of a specific nucleic acid in a sample. In one aspect of the invention, message isolated from a cell or a cDNA library are amplified. The skilled artisan can select and design suitable oligonucleotide amplification primers. Amplification methods are also well known in the art, and include, e.g., polymerase chain reaction, PCR (see, e.g., PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477-1491), automated Q-beta replicase amplification assay (see, e.g., Burg (1996) Mol. Cell. Probes 10:257-271) and other RNA polymerase mediated techniques (e.g., NASBA, Cangene, Mississauga, Ontario); see also Berger (1987) Methods Enzymol. 152:307-316; Sambrook; Ausubel; U.S. Pat. Nos. 4,683,195 and 4,683,202; Sooknanan (1995) Biotechnology 13:563-564.

Determining the Degree of Sequence Identity

The invention provides nucleic acids comprising sequences having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention (e.g., SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and nucleic acids encoding SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30, or enzymatically active fragments thereof) over a region of at least about 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or more, residues. The invention provides polypeptides comprising sequences having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary polypeptide of the invention. The extent of sequence identity (homology) may be determined using any computer program and associated parameters, including those described herein, such as BLAST 2.2.2. or FASTA version 3.0t78, with the default parameters.

In alternative embodiments, the sequence identify can be over a region of at least about 5, 10, 20, 30, 40, 50, 100, 150, 200, 250, 300, 350, 400 consecutive residues, or the full length of the nucleic acid or polypeptide. The extent of sequence identity (homology) may be determined using any computer program and associated parameters, including those described herein, such as BLAST 2.2.2. or FASTA version 3.0t78, with the default parameters.

Homologous sequences also include RNA sequences in which uridines replace the thymines in the nucleic acid sequences. The homologous sequences may be obtained using any of the procedures described herein or may result from the correction of a sequencing error. It will be appreciated that the nucleic acid sequences as set forth herein can be represented in the traditional single character format (see, e.g., Stryer, Lubert. Biochemistry, 3rd Ed., W. H Freeman & Co., New York) or in any other format which records the identity of the nucleotides in a sequence.

Various sequence comparison programs identified herein are used in this aspect of the invention. Protein and/or nucleic acid sequence identities (homologies) may be evaluated using any of the variety of sequence comparison algorithms and programs known in the art. Such algorithms and programs include, but are not limited to, TBLASTN, BLASTP, FASTA, TFASTA, and CLUSTALW (Pearson and Lipman, Proc. Natl. Acad. Sci. USA 85(8):2444-2448, 1988; Altschul et al., J. Mol. Biol. 215(3):403-410, 1990; Thompson et al., Nucleic Acids Res. 22(2):4673-4680, 1994; Higgins et al., Methods Enzymol. 266:383-402, 1996; Altschul et al., J. Mol. Biol. 215(3):403-410, 1990; Altschul et al., Nature Genetics 3:266-272, 1993).

Homology or identity can be measured using sequence analysis software (e.g., Sequence Analysis Software Package of the Genetics Computer Group, University of Wisconsin Biotechnology Center, 1710University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. For sequence comparison, one sequence can act as a reference sequence (an exemplary sequence SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, etc.) to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous residues. For example, in alternative aspects of the invention, continugous residues ranging anywhere from 20 to the full length of an exemplary sequence of the invention are compared to a reference sequence of the same number of contiguous positions after the two sequences are optimally aligned. If the reference sequence has the requisite sequence identity to an exemplary sequence of the invention, e.g., 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to a sequence of the invention, that (reference) sequence is within the scope of the invention. In alternative embodiments, subsequences ranging from about 20 to 600, about 50 to 200, and about 100 to 150 are compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol. 48:443, 1970, by the search for similarity method of person & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (Gibbs, 1995). Several genomes have been sequenced, e.g., *M. genitalium* (Fraser et al., 1995), *M. jannaschii* (Bult et al., 1996), *H. influenzae* (Fleischmann et al., 1995), *E. coli* (Blattner et al., 1997), and yeast (*S. cerevisiae*) (Mewes et al., 1997), and *D. melanogaster* (Adams et al., 2000). Significant progress has also been made in sequencing the genomes of model organism, such as mouse, *C. elegans*, and *Arabadopsis* sp. Databases containing genomic information annotated with some functional information are maintained by different organization, and are accessible via the internet.

BLAST, BLAST 2.0 and BLAST 2.2.2 algorithms are also used to practice the invention. They are described, e.g., in Altschul (1977) Nuc. Acids Res. 25:3389-3402; Altschul (1990) J. Mol. Biol. 215:403-410. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990) supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff (1989) Proc. Natl. Acad. Sci. USA 89:10915) alignments (B) of 50, expectation (E) of 10, M=5, N=−4, and a comparison of both strands. The BLAST algorithm also performs a statistical analysis of the similarity between two sequences (see, e.g., Karlin & Altschul (1993) Proc. Natl. Acad. Sci. USA 90:5873). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001. In one aspect, protein and nucleic acid sequence homologies are evaluated using the Basic Local Alignment Search Tool ("BLAST"). For example, five specific BLAST programs can be used to perform the following task: (1) BLASTP and BLAST3 compare an amino acid query sequence against a protein sequence database; (2) BLASTN compares a nucleotide query sequence against a nucleotide sequence database; (3) BLASTX compares the six-frame conceptual translation products of a query nucleotide sequence (both strands) against a protein sequence database; (4) TBLASTN compares a query protein sequence against a nucleotide sequence database translated in all six reading frames (both strands); and, (5) TBLASTX compares the six-frame translations of a nucleotide query sequence against the six-frame translations of a nucleotide sequence database. The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443-1445, 1992; Henikoff and Henikoff, Proteins 17:49-61, 1993). Less preferably, the PAM or PAM250 matrices may also be used (see, e.g., Schwartz and Dayhoff, eds., 1978, Matrices for Detecting Distance Relationships: Atlas of Protein Sequence and Structure, Washington: National Biomedical Research Foundation).

In one aspect of the invention, to determine if a nucleic acid has the requisite sequence identity to be within the scope of the invention, the NCBI BLAST 2.2.2 programs is used default options to blastp. There are about 38 setting options in the BLAST 2.2.2 program. In this exemplary aspect of the invention, all default values are used except for the default filtering setting (i.e., all parameters set to default except filtering which is set to OFF); in its place a "-F F" setting is used, which disables filtering. Use of default filtering often results in Karlin-Altschul violations due to short length of sequence.

The default values used in this exemplary aspect of the invention include:

"Filter for low complexity: ON
Word Size: 3
Matrix: Blosum62
Gap Costs: Existence: 11
    Extension: 1"

Other default settings are: filter for low complexity OFF, word size of 3 for protein, BLOSUM62 matrix, gap existence penalty of −11 and a gap extension penalty of −1.

An exemplary NCBI BLAST 2.2.2 program setting is set forth in Example 1, below. Note that the "-W" option defaults to 0. This means that, if not set, the word size defaults to 3 for proteins and 11 for nucleotides.

Computer Systems and Computer Program Products

To determine and identify sequence identities, structural homologies, motifs and the like in silico the sequence of the invention can be stored, recorded, and manipulated on any medium which can be read and accessed by a computer. Accordingly, the invention provides computers, computer systems, computer readable mediums, computer programs products and the like recorded or stored thereon the nucleic acid and polypeptide sequences of the invention, e.g., an exemplary sequence of the invention, e.g., SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, etc. As used herein, the words "recorded" and "stored" refer to a process for storing information on a computer medium. A skilled artisan can readily adopt any known methods for recording information on a computer readable medium to generate manufactures comprising one or more of the nucleic acid and/or polypeptide sequences of the invention.

Another aspect of the invention is a computer readable medium having recorded thereon at least one nucleic acid and/or polypeptide sequence of the invention. Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Aspects of the invention include systems (e.g., internet based systems), particularly computer systems, which store and manipulate the sequences and sequence information described herein. One example of a computer system 100 is illustrated in block diagram form in FIG. 1. As used herein, "a computer system" refers to the hardware components, software components, and data storage components used to analyze a nucleotide or polypeptide sequence of the invention. The computer system 100 can include a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines. The computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one aspect, the computer system 100 includes a processor 105 connected to a bus which is connected to a main memory 115 (preferably implemented as RAM) and one or more internal data storage devices 110, such as a hard drive and/or other computer readable media having data recorded thereon. The computer system 100 can further include one or more data retrieving device 118 for reading the data stored on the internal data storage devices 110.

The data retrieving device 118 may represent, for example, a floppy disk drive, a compact disk drive, a magnetic tape drive, or a modem capable of connection to a remote data storage system (e.g., via the internet) etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125a-c in a network or wide area network to provide centralized access to the computer system 100. Software for accessing and processing the nucleotide or amino acid sequences of the invention can reside in main memory 115 during execution.

In some aspects, the computer system 100 may further comprise a sequence comparison algorithm for comparing a nucleic acid sequence of the invention. The algorithm and sequence(s) can be stored on a computer readable medium. A "sequence comparison algorithm" refers to one or more programs which are implemented (locally or remotely) on the computer system 100 to compare a nucleotide sequence with other nucleotide sequences and/or compounds stored within a data storage means. For example, the sequence comparison algorithm may compare the nucleotide sequences of an exemplary sequence stored on a computer readable medium to reference sequences stored on a computer readable medium to identify homologies or structural motifs.

Figure 2:
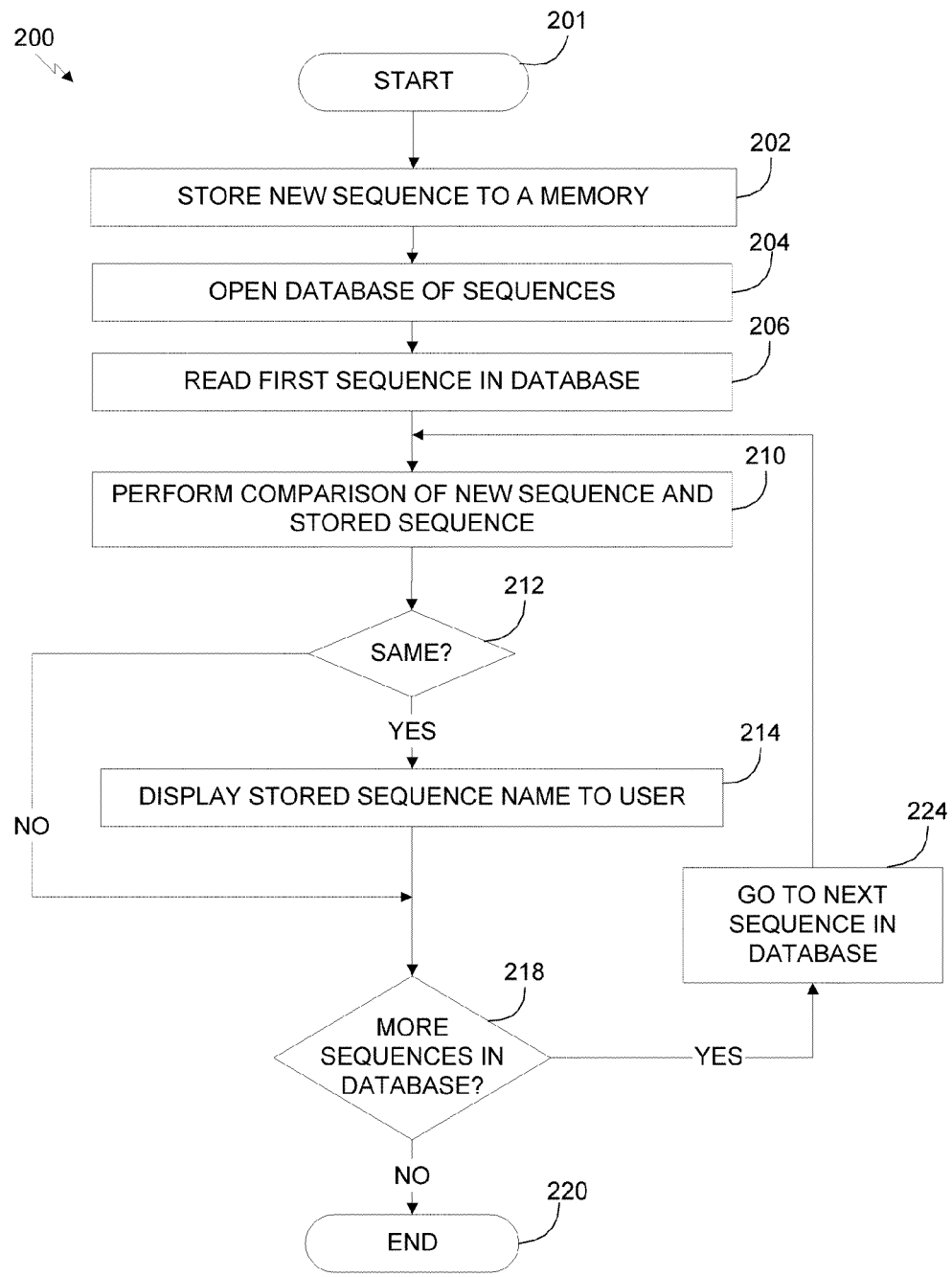
FIG. 2 is a flow diagram illustrating one aspect of a process for comparing a new nucleotide or protein sequence with a database of sequences in order to determine the homology levels between the new sequence and the sequences in the database.

The parameters used with the above algorithms may be adapted depending on the sequence length and degree of homology studied. In some aspects, the parameters may be the default parameters used by the algorithms in the absence of instructions from the user. FIG. 2 is a flow diagram illustrating one aspect of a process 200 for comparing a new nucleotide or protein sequence with a database of sequences in order to determine the homology levels between the new sequence and the sequences in the database. The database of sequences can be a private database stored within the computer system 100, or a public database such as GENBANK that is available through the Internet. The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200. If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison. Accordingly, one aspect of the invention is a computer system comprising a processor, a data storage device having stored thereon a nucleic acid sequence of the invention and a sequence comparer for conducting the comparison. The sequence comparer may indicate a homology level between the sequences compared or identify structural motifs, or it may identify structural motifs in sequences which are compared to these nucleic acid codes and polypeptide codes.

Figure 3:
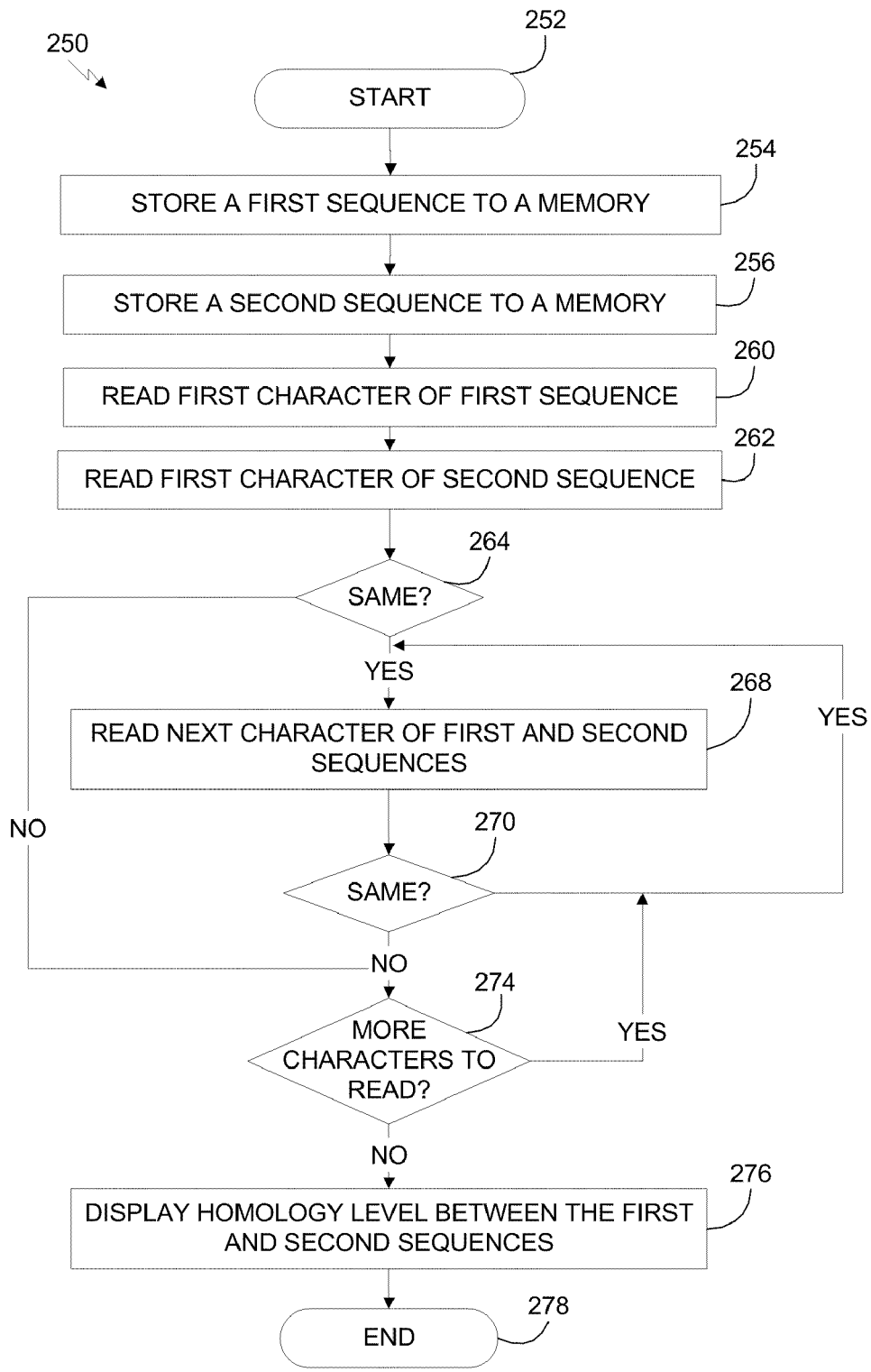
FIG. 3 is a flow diagram illustrating one aspect of a process in a computer for determining whether two sequences are homologous.

FIG. 3 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it can be a single letter amino acid code so that the first and sequence sequences can be easily compared. A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read. If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%.

Alternatively, the computer program can compare a reference sequence to a sequence of the invention to determine whether the sequences differ at one or more positions. The program can record the length and identity of inserted, deleted or substituted nucleotides or amino acid residues with respect to the sequence of either the reference or the invention. The computer program may be a program which determines whether a reference sequence contains a single nucleotide polymorphism (SNP) with respect to a sequence of the invention, or, whether a sequence of the invention comprises a SNP of a known sequence. Thus, in some aspects, the computer program is a program which identifies SNPs. The method may be implemented by the computer systems described above and the method illustrated in FIG. 3. The method can be performed by reading a sequence of the invention and the reference sequences through the use of the computer program and identifying differences with the computer program.

Figure 4:
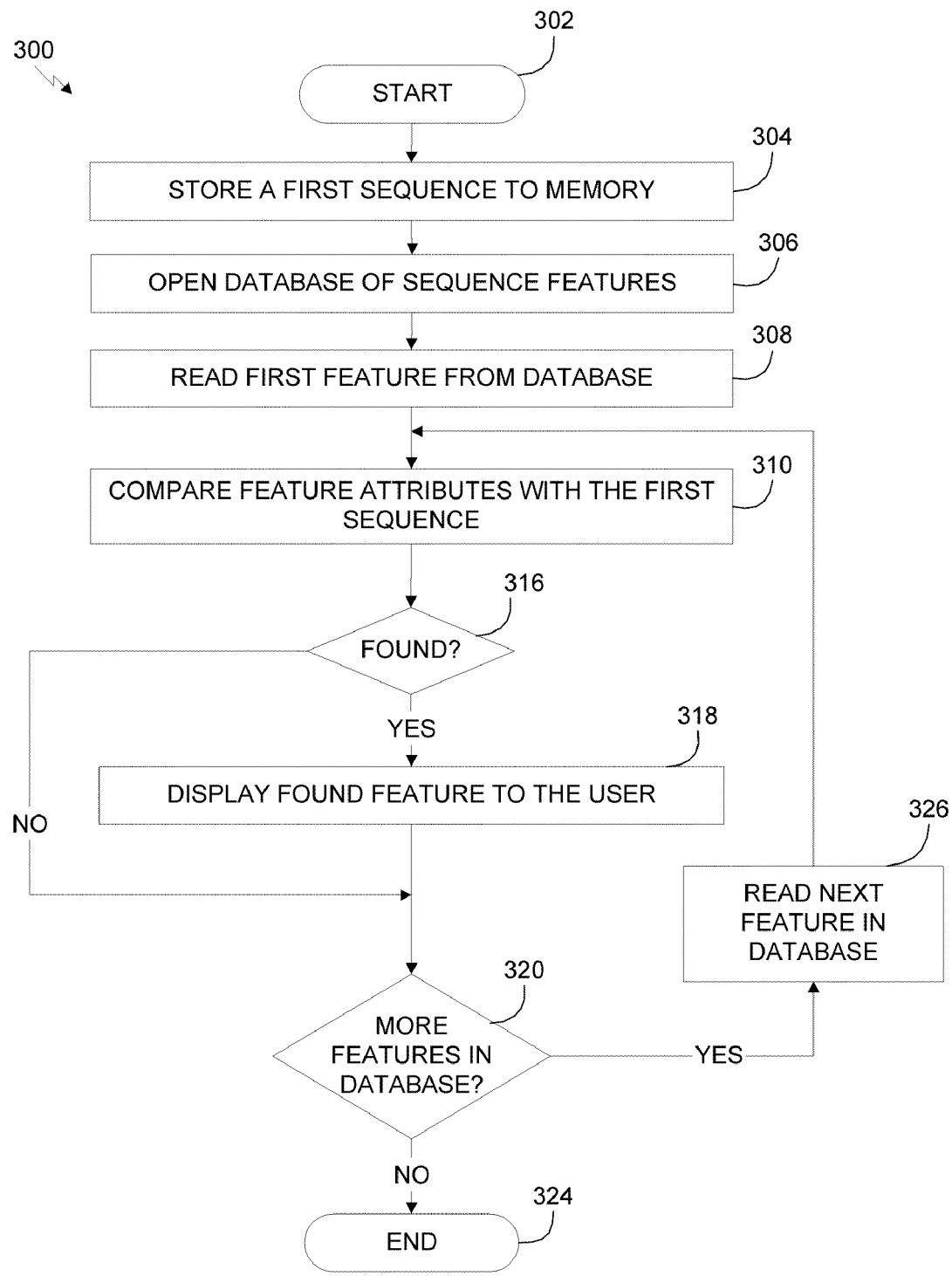
FIG. 4 is a flow diagram illustrating one aspect of an identifier process 300 for detecting the presence of a feature in a sequence.

In other aspects the computer based system comprises an identifier for identifying features within a nucleic acid or polypeptide of the invention. An "identifier" refers to one or more programs which identifies certain features within a nucleic acid sequence. For example, an identifier may comprise a program which identifies an open reading frame (ORF) in a nucleic acid sequence. FIG. 4 is a flow diagram illustrating one aspect of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group. Alternatively, the features may be structural polypeptide motifs such as alpha helices, beta sheets, or functional polypeptide motifs such as enzymatic active sites, helix-turn-helix motifs or other motifs known to those skilled in the art. Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user. The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence. If the feature attribute is not found in the first sequence at the decision state 316, the process 300 moves directly to the decision state 320 in order to determine if any more features exist in the database. Thus, in one aspect, the invention provides a computer program that identifies open reading frames (ORFs).

A polypeptide or nucleic acid sequence of the invention may be stored and manipulated in a variety of data processor programs in a variety of formats. For example, a sequence can be stored as text in a word processing file, such as Microsoft-WORD or WORDPERFECT or as an ASCII file in a variety of database programs familiar to those of skill in the art, such as DB2, SYBASE, or ORACLE. In addition, many computer programs and databases may be used as sequence comparison algorithms, identifiers, or sources of reference nucleotide sequences or polypeptide sequences to be compared to a nucleic acid sequence of the invention. The programs and databases used to practice the invention include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, J. Mol. Biol. 215: 403, 1990), FASTA (Pearson and Lipman, Proc. Natl. Acad. Sci. USA, 85: 2444, 1988), FASTDB (Brutlag et al. Comp. App. Biosci. 6:237-245, 1990), Catalyst (Molecular Simulations Inc.), Catalyst/SHAPE (Molecular Simulations Inc.), Cerius2.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwent's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

Hybridization of Nucleic Acids

The invention provides isolated or recombinant nucleic acids that hybridize under stringent conditions to an exemplary sequence of the invention, e.g., a sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or a nucleic acid that encodes a polypeptide comprising a sequence as set forth in SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30, or enzymatically active fragments thereof. The stringent conditions can be highly stringent conditions, medium stringent conditions, low stringent conditions, including the high and reduced stringency conditions described herein. In alternative embodiments, nucleic acids of the invention as defined by their ability to hybridize under stringent conditions can be between about five residues and the full length of the molecule, e.g., an exemplary nucleic acid of the invention. For example, they can be at least 5, 10, 15, 20, 25, 30, 35, 40, 50, 55, 60, 65, 70, 75, 80, 90, 100, 150, 200, 250, 300, 350, 400 residues in length. Nucleic acids shorter than full length are also included. These nucleic acids are useful as, e.g., hybridization probes, labeling probes, PCR oligonucleotide probes, iRNA (single or double stranded), antisense or sequences encoding antibody binding peptides (epitopes), motifs, active sites and the like.

In one aspect, nucleic acids of the invention are defined by their ability to hybridize under high stringency comprises conditions of about 50% formamide at about 37° C. to 42° C. In one aspect, nucleic acids of the invention are defined by their ability to hybridize under reduced stringency comprising conditions in about 35% to 25% formamide at about 30° C. to 35° C. Alternatively, nucleic acids of the invention are defined by their ability to hybridize under high stringency comprising conditions at 42° C. in 50% formamide, 5×SSPE, 0.3% SDS, and a repetitive sequence blocking nucleic acid, such as cot-1 or salmon sperm DNA (e.g., 200 n/ml sheared and denatured salmon sperm DNA). In one aspect, nucleic acids of the invention are defined by their ability to hybridize under reduced stringency conditions comprising 35% formamide at a reduced temperature of 35° C.

Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

The temperature range corresponding to a particular level of stringency can be further narrowed by calculating the purine to pyrimidine ratio of the nucleic acid of interest and adjusting the temperature accordingly. Nucleic acids of the invention are also defined by their ability to hybridize under high, medium, and low stringency conditions as set forth in Ausubel and Sambrook. Variations on the above ranges and conditions are well known in the art. Hybridization conditions are discussed further, below.

Oligonucleotides Probes and Methods for Using them

The invention also provides nucleic acid probes for identifying nucleic acids encoding a polypeptide with an aldolase activity. In one aspect, the probe comprises at least 10 consecutive bases of a sequence of the invention, e.g., SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or, a nucleic acid encoding SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30, or enzymatically active fragments thereof. Alternatively, a probe of the invention can be at least about 5, 6, 7, 8, 9, 10, 11, 12, 13, 14, 15, 16, 17, 18, 19, 20, 21, 22, 23, 24, 25, 30, 35, 40, 50, 55, 60, 65, 70, 75, 80, 90, 100, 150, about 10 to 50, about 20 to 60 about 30 to 70, consecutive bases of a sequence as set forth in a sequence of the invention. The probes identify a nucleic acid by binding or hybridization. The probes can be used in arrays of the invention, see discussion below, including, e.g., capillary arrays. The probes of the invention can also be used to isolate other nucleic acids or polypeptides.

The probes of the invention can be used to determine whether a biological sample, such as an environmental sample, e.g., a soil sample, contains an organism having a nucleic acid sequence of the invention or an organism from which the nucleic acid was obtained. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences present in the sample. Where necessary, conditions which permit the probe to specifically hybridize to complementary sequences may be determined by placing the probe in contact with complementary sequences from samples known to contain the complementary sequence, as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids (see discussion on specific hybridization conditions).

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product. Many methods for using the labeled probes to detect the presence of complementary nucleic acids in a sample are familiar to those skilled in the art. These include Southern Blots, Northern Blots, colony hybridization procedures, and dot blots. Protocols for each of these procedures are provided in Ausubel and Sambrook.

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). In one aspect, the probes comprise oligonucleotides. In one aspect, the amplification reaction may comprise a PCR reaction. PCR protocols are described in Ausubel and Sambrook (see discussion on amplification reactions). In such procedures, the nucleic acids in the sample are contacted with the probes, the amplification reaction is performed, and any resulting amplification product is detected. The amplification product may be detected by performing gel electrophoresis on the reaction products and staining the gel with an intercalator such as ethidium bromide. Alternatively, one or more of the probes may be labeled with a radioactive isotope and the presence of a radioactive amplification product may be detected by autoradiography after gel electrophoresis.

Probes derived from sequences near the 3' or 5' ends of a nucleic acid sequence of the invention can also be used in chromosome walking procedures to identify clones containing additional, e.g., genomic sequences. Such methods allow the isolation of genes which encode additional proteins of interest from the host organism.

In one aspect, nucleic acid sequences of the invention are used as probes to identify and isolate related nucleic acids. In some aspects, the so-identified related nucleic acids may be cDNAs or genomic DNAs from organisms other than the one from which the nucleic acid of the invention was first isolated. In such procedures, a nucleic acid sample is contacted with the probe under conditions which permit the probe to specifically hybridize to related sequences. Hybridization of the probe to nucleic acids from the related organism is then detected using any of the methods described above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter. Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM NaH2PO4, pH 7.0, 5.0 mM Na2EDTA, 0.5% SDS, 10×Denhardt's, and 0.5 mg/ml polyriboadenylic acid. Approximately $2 \times 10^7$ cpm (specific activity $4-9 \times 10^8$ cpm/ug) of $^{32}$P end-labeled oligonucleotide probe are then added to the solution. After 12-16 hours of incubation, the membrane is washed for 30 minutes at room temperature (RT) in 1×SET (150 mM NaCl, 20 mM Tris hydrochloride, pH 7.8, 1 mM Na2EDTA) containing 0.5% SDS, followed by a 30 minute wash in fresh 1×SET at Tm−10° C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, Tm, is the temperature (under defined ionic strength and pH) at which 50% of the target sequence hybridizes to a perfectly complementary probe. Very stringent conditions are selected to be equal to or about 5° C. lower than the Tm for a particular probe. The melting temperature of the probe may be calculated using the following exemplary formulas. For probes between 14 and 70 nucleotides in length the melting temperature (Tm) is calculated using the formula: Tm=81.5+16.6(log [Na+])+0.41(fraction G+C)−(600/N) where N is the length of the probe. If the hybridization is carried out in a solution containing formamide, the melting temperature may be calculated using the equation: Tm=81.5+16.6(log [Na+])+0.41 (fraction G+C)−(0.63% formamide)−(600/N) where N is the length of the probe. Prehybridization may be carried out in 6×SSC, 5×Denhardt's reagent, 0.5% SDS, 100 μg denatured fragmented salmon sperm DNA or 6×SSC, 5×Denhardt's reagent, 0.5% SDS, 100 μg denatured fragmented salmon sperm DNA, 50% formamide. Formulas for SSC and Denhardt's and other solutions are listed, e.g., in Sambrook.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the Tm. For shorter probes, such as oligonucleotide probes, the hybridization may be conducted at 5-10° C. below the Tm. In one aspect, hybridizations in 6×SSC are conducted at approximately 68° C. In one aspect, hybridizations in 50% formamide containing solutions are conducted at approximately 42° C. All of the foregoing hybridizations would be considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes.

Nucleic acids which have hybridized to the probe can be identified by autoradiography or other conventional techniques. The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C. An example of "moderate" hybridization conditions is when the above hybridization is conducted at 55° C. An example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

These probes and methods of the invention can be used to isolate nucleic acids having a sequence with at least about 99%, 98%, 97%, at least 95%, at least 90%, at least 85%, at least 80%, at least 75%, at least 70%, at least 65%, at least 60%, at least 55%, or at least 50% homology to a nucleic acid sequence of the invention comprising at least about 10, 15, 20, 25, 30, 35, 40, 50, 75, 100, 150, 200, 250, 300, 350, 400, or 500 consecutive bases thereof, and the sequences complementary thereto. Homology may be measured using an alignment algorithm, as discussed herein. For example, the homologous polynucleotides may have a coding sequence which is a naturally occurring allelic variant of one of the coding sequences described herein. Such allelic variants may have a substitution, deletion or addition of one or more nucleotides when compared to nucleic acids of the invention.

Additionally, the probes and methods of the invention may be used to isolate nucleic acids which encode polypeptides having at least about 99%, at least 95%, at least 90%, at least 85%, at least 80%, at least 75%, at least 70%, at least 65%, at least 60%, at least 55%, or at least 50% sequence identity (homology) to a polypeptide of the invention comprising at least 5, 10, 15, 20, 25, 30, 35, 40, 50, 75, 100, or 150 consecutive amino acids thereof as determined using a sequence alignment algorithm (e.g., such as the FASTA version 3.0t78 algorithm with the default parameters, or a BLAST 2.2.2 program with exemplary settings as set forth herein).

Inhibiting Expression of Aldolases and Lyases

The invention provides nucleic acids complementary to (e.g., antisense sequences to) the nucleic acids of the invention, e.g., polynucleotides encoding proteins of the invention have an aldolase activity, e.g., aldolase enzyme-encoding nucleic acids. The invention further provides nucleic acids complementary to (e.g., antisense sequences to) aldolases and lyases.

Antisense sequences are capable of inhibiting the transport, splicing or transcription of aldolase-encoding genes. The inhibition can be effected through the targeting of genomic DNA or messenger RNA. The transcription or function of targeted nucleic acid can be inhibited, for example, by hybridization and/or cleavage. One particularly useful set of inhibitors provided by the present invention includes oligonucleotides which are able to either bind aldolase gene or message, in either case preventing or inhibiting the production or function of aldolase enzyme. The association can be though sequence specific hybridization. Another useful class of inhibitors includes oligonucleotides which cause inactivation or cleavage of aldolase message. The oligonucleotide can have enzyme activity which causes such cleavage, such as ribozymes. The oligonucleotide can be chemically modified or conjugated to an enzyme or composition capable of cleaving the complementary nucleic acid. One may screen a pool of many different such oligonucleotides for those with the desired activity.

The compositions of the invention for the inhibition of aldolase expression (e.g., antisense, iRNA, ribozymes, antibodies) can be used as pharmaceutical compositions.

Antisense Oligonucleotides

The invention provides antisense oligonucleotides capable of binding aldolase message which can inhibit aldolase activity by targeting mRNA. Strategies for designing antisense oligonucleotides are well described in the scientific and patent literature, and the skilled artisan can design such aldolase oligonucleotides using the novel reagents of the invention. For example, gene walking/RNA mapping protocols to screen for effective antisense oligonucleotides are well known in the art, see, e.g., Ho (2000) Methods Enzymol. 314:168-183, describing an RNA mapping assay, which is based on standard molecular techniques to provide an easy and reliable method for potent antisense sequence selection. See also Smith (2000) Eur. J. Pharm. Sci. 11:191-198.

Naturally occurring nucleic acids are used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl)glycine units can be used. Antisense oligonucleotides having phosphorothioate linkages can also be used, as described in WO 97/03211; WO 96/39154; Mata (1997) Toxicol Appl Pharmacol 144:189-197; Antisense Therapeutics, ed. Agrawal (Humana Press, Totowa, N.J., 1996). Antisense oligonucleotides having synthetic DNA backbone analogues provided by the invention can also include phosphorodithioate, methylphosphonate, phosphoramidate, alkyl phosphotriester, sulfamate, 3'-thioacetal, methylene(methylimino), 3'-N-carbamate, and morpholino carbamate nucleic acids, as described above.

Combinatorial chemistry methodology can be used to create vast numbers of oligonucleotides that can be rapidly screened for specific oligonucleotides that have appropriate binding affinities and specificities toward any target, such as the sense and antisense aldolase sequences of the invention (see, e.g., Gold (1995) J. of Biol. Chem. 270:13581-13584).

Inhibitory Ribozymes

The invention provides for with ribozymes capable of binding aldolase message which can inhibit aldolase enzyme activity by targeting mRNA. Strategies for designing ribozymes and selecting the aldolase-specific antisense sequence for targeting are well described in the scientific and patent literature, and the skilled artisan can design such ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it is typically released from that RNA and so can bind and cleave new targets repeatedly.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme is typically a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site.

The enzymatic ribozyme RNA molecule can be formed in a hammerhead motif, but may also be formed in the motif of a hairpin, hepatitis delta virus, group I intron or RNaseP-like RNA (in association with an RNA guide sequence). Examples of such hammerhead motifs are described by Rossi (1992) Aids Research and Human Retroviruses 8:183; hairpin motifs by Hampel (1989) Biochemistry 28:4929, and Hampel (1990) Nuc. Acids Res. 18:299; the hepatitis delta virus motif by Perrotta (1992) Biochemistry 31:16; the RNaseP motif by Guerrier-Takada (1983) Cell 35:849; and the group I intron by Cech U.S. Pat. No. 4,987,071. The recitation of these specific motifs is not intended to be limiting; those skilled in the art will recognize that an enzymatic RNA molecule of this invention has a specific substrate binding site complementary to one or more of the target gene RNA regions, and has nucleotide sequence within or surrounding that substrate binding site which imparts an RNA cleaving activity to the molecule.

RNA Interference (RNAi)

In one aspect, the invention provides an RNA inhibitory molecule, a so-called "RNAi" molecule, comprising an aldolase sequence of the invention. The RNAi molecule comprises a double-stranded RNA (dsRNA) molecule. The RNAi can inhibit expression of an aldolase gene. In one aspect, the RNAi is about 15, 16, 17, 18, 19, 20, 21, 22, 23, 24, 25 or more duplex nucleotides in length. While the invention is not limited by any particular mechanism of action, the RNAi can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi is the breaking of a double-stranded RNA (dsRNA) matching a specific gene sequence into short pieces called short interfering RNA, which trigger the degradation of mRNA that matches its sequence. In one aspect, the RNAi's of the invention are used in gene-silencing therapeutics, see, e.g., Shuey (2002) Drug Discov. Today 7:1040-1046. In one aspect, the invention provides methods to selectively degrade RNA using the RNAi's of the invention. The process may be practiced in vitro, ex vivo or in vivo. In one aspect, the RNAi molecules of the invention can be used to generate a loss-of-function mutation in a cell, an organ or an animal. Methods for making and using RNAi molecules for selectively degrade RNA are well known in the art, see, e.g., U.S. Pat. Nos. 6,506,559; 6,511,824; 6,515,109; 6,489,127.

Modification of Nucleic Acids

The invention provides methods of generating variants of the nucleic acids of the invention, e.g., those encoding an aldolase enzyme. These methods can be repeated or used in various combinations to generate aldolase enzymes having an altered or different activity or an altered or different stability from that of an aldolase encoded by the template nucleic acid. These methods also can be repeated or used in various combinations, e.g., to generate variations in gene/message expression, message translation or message stability. In another aspect, the genetic composition of a cell is altered by, e.g., modification of a homologous gene ex vivo, followed by its reinsertion into the cell.

A nucleic acid of the invention can be altered by any means. For example, random or stochastic methods, or, non-stochastic, or "directed evolution," methods.

Methods for random mutation of genes are well known in the art, see, e.g., U.S. Pat. No. 5,830,696. For example, mutagens can be used to randomly mutate a gene. Mutagens include, e.g., ultraviolet light or gamma irradiation, or a chemical mutagen, e.g., mitomycin, nitrous acid, photoactivated psoralens, alone or in combination, to induce DNA breaks amenable to repair by recombination. Other chemical mutagens include, for example, sodium bisulfite, nitrous acid, hydroxylamine, hydrazine or formic acid. Other mutagens are analogues of nucleotide precursors, e.g., nitrosoguanidine, 5-bromouracil, 2-aminopurine, or acridine. These agents can be added to a PCR reaction in place of the nucleotide precursor thereby mutating the sequence. Intercalating agents such as proflavine, acriflavine, quinacrine and the like can also be used.

Any technique in molecular biology can be used, e.g., random PCR mutagenesis, see, e.g., Rice (1992) Proc. Natl. Acad. Sci. USA 89:5467-5471; or, combinatorial multiple cassette mutagenesis, see, e.g., Crameri (1995) Biotechniques 18:194-196. Alternatively, nucleic acids, e.g., genes, can be reassembled after random, or "stochastic," fragmentation, see, e.g., U.S. Pat. Nos. 6,291,242; 6,287,862; 6,287,861; 5,955,358; 5,830,721; 5,824,514; 5,811,238; 5,605,793. In alternative aspects, modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis (GSSM), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and/or a combination of these and other methods.

The following publications describe a variety of recursive recombination procedures and/or methods which can be incorporated into the methods of the invention: Stemmer (1999) "Molecular breeding of viruses for targeting and other clinical properties" Tumor Targeting 4:1-4; Ness (1999) Nature Biotechnology 17:893-896; Chang (1999) "Evolution of a cytokine using DNA family shuffling" Nature Biotechnology 17:793-797; Minshull (1999) "Protein evolution by molecular breeding" Current Opinion in Chemical Biology 3:284-290; Christians (1999) "Directed evolution of thymidine kinase for AZT phosphorylation using DNA family shuffling" Nature Biotechnology 17:259-264; Crameri (1998) "DNA shuffling of a family of genes from diverse species accelerates directed evolution" Nature 391:288-291; Crameri (1997) "Molecular evolution of an arsenate detoxification pathway by DNA shuffling," Nature Biotechnology 15:436-438; Zhang (1997) "Directed evolution of an effective fucosidase from a galactosidase by DNA shuffling and screening" Proc. Natl. Acad. Sci. USA 94:4504-4509; Patten et al. (1997) "Applications of DNA Shuffling to Pharmaceuticals and Vaccines" Current Opinion in Biotechnology 8:724-733; Crameri et al. (1996) "Construction and evolution of antibody-phage libraries by DNA shuffling" Nature Medicine 2:100-103; Crameri et al. (1996) "Improved green fluorescent protein by molecular evolution using DNA shuffling" Nature Biotechnology 14:315-319; Gates et al. (1996) "Affinity selective isolation of ligands from peptide libraries through display on a lac repressor 'headpiece dimer'" Journal of Molecular Biology 255:373-386; Stemmer (1996) "Sexual PCR and Assembly PCR" In: The Encyclopedia of Molecular Biology. VCH Publishers, New York. pp. 447-457; Crameri and Stemmer (1995) "Combinatorial multiple cassette mutagenesis creates all the permutations of mutant and wild-type cassettes" BioTechniques 18:194-195; Stemmer et al. (1995) "Single-step assembly of a gene and entire plasmid form large numbers of oligodeoxyribonucleotides" Gene, 164:49-53; Stemmer (1995) "The Evolution of Molecular Computation" Science 270: 1510; Stemmer (1995) "Searching Sequence Space" Bio/Technology 13:549-553; Stemmer (1994) "Rapid evolution of a protein in vitro by DNA shuffling" Nature 370:389-391; and Stemmer (1994) "DNA shuffling by random fragmentation and reassembly: In vitro recombination for molecular evolution." Proc. Natl. Acad. Sci. USA 91:10747-10751.

Mutational methods of generating diversity include, for example, site-directed mutagenesis (Ling et al. (1997) "Approaches to DNA mutagenesis: an overview" Anal Biochem. 254(2): 157-178; Dale et al. (1996) "Oligonucleotide-directed random mutagenesis using the phosphorothioate method" Methods Mol. Biol. 57:369-374; Smith (1985) "In vitro mutagenesis" Ann. Rev. Genet. 19:423-462; Botstein & Shortle (1985) "Strategies and applications of in vitro mutagenesis" Science 229:1193-1201; Carter (1986) "Site-directed mutagenesis" Biochem. J. 237:1-7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488-492; Kunkel et al. (1987) "Rapid and efficient site-specific mutagenesis without phenotypic selection" Methods in Enzymol. 154, 367-382; and Bass et al. (1988) "Mutant Trp repressors with new DNA-binding specificities" Science 242:240-245); oligonucleotide-directed mutagenesis (Methods in Enzymol. 100: 468-500 (1983); Methods in Enzymol. 154: 329-350 (1987); Zoller & Smith (1982) "Oligonucleotide-directed mutagenesis using M13-derived vectors: an efficient and general procedure for the production of point mutations in any DNA fragment" Nucleic Acids Res. 10:6487-6500; Zoller & Smith (1983) "Oligonucleotide-directed mutagenesis of DNA fragments cloned into M13 vectors" Methods in Enzymol. 100: 468-500; and Zoller & Smith (1987) "Oligonucleotide-directed mutagenesis: a simple method using two oligonucleotide primers and a single-stranded DNA template" Methods in Enzymol. 154:329-350); phosphorothioate-modified DNA mutagenesis (Taylor et al. (1985) "The use of phosphorothioate-modified DNA in restriction enzyme reactions to prepare nicked DNA" Nucl. Acids Res. 13: 8749-8764; Taylor et al. (1985) "The rapid generation of oligonucleotide-directed mutations at high frequency using phosphorothioate-modified DNA" Nucl. Acids Res. 13: 8765-8787 (1985); Nakamaye (1986) "Inhibition of restriction endonuclease Nci I cleavage by phosphorothioate groups and its application to oligonucleotide-directed mutagenesis" Nucl. Acids Res. 14: 9679-9698; Sayers et al. (1988) "Y-T Exonucleases in phosphorothioate-based oligonucleotide-directed mutagenesis" Nucl. Acids Res. 16:791-802; and Sayers et al. (1988) "Strand specific cleavage of phosphorothioate-containing DNA by reaction with restriction endonucleases in the presence of ethidium bromide" Nucl. Acids Res. 16: 803-814); mutagenesis using gapped duplex DNA (Kramer et al. (1984) "The gapped duplex DNA approach to oligonucleotide-directed mutation construction" Nucl. Acids Res. 12: 9441-9456; Kramer & Fritz (1987) Methods in Enzymol. "Oligonucleotide-directed construction of mutations via gapped duplex DNA" 154:350-367; Kramer et al. (1988) "Improved enzymatic in vitro reactions in the gapped duplex DNA approach to oligonucleotide-directed construction of mutations" Nucl. Acids Res. 16: 7207; and Fritz et al. (1988) "Oligonucleotide-directed construction of mutations: a gapped duplex DNA procedure without enzymatic reactions in vitro" Nucl. Acids Res. 16: 6987-6999).

Additional protocols used in the methods of the invention include point mismatch repair (Kramer (1984) "Point Mismatch Repair" Cell 38:879-887), mutagenesis using repair-deficient host strains (Carter et al. (1985) "Improved oligonucleotide site-directed mutagenesis using M13 vectors" Nucl. Acids Res. 13: 4431-4443; and Carter (1987) "Improved oligonucleotide-directed mutagenesis using M13 vectors" Methods in Enzymol. 154: 382-403), deletion mutagenesis (Eghtedarzadeh (1986) "Use of oligonucleotides to generate large deletions" Nucl. Acids Res. 14: 5115), restriction-selection and restriction-selection and restriction-purification (Wells et al. (1986) "Importance of hydrogen-bond formation in stabilizing the transition state of subtilisin" Phil. Trans. R. Soc. Lond. A 317: 415-423), mutagenesis by total gene synthesis (Nambiar et al. (1984) "Total synthesis and cloning of a gene coding for the ribonuclease S protein" Science 223: 1299-1301; Sakamar and Khorana (1988) "Total synthesis and expression of a gene for the a-subunit of bovine rod outer segment guanine nucleotide-binding protein (transducin)" Nucl. Acids Res. 14: 6361-6372; Wells et al. (1985) "Cassette mutagenesis: an efficient method for generation of multiple mutations at defined sites" Gene 34:315-323; and Grundstrom et al. (1985) "Oligonucleotide-directed mutagenesis by microscale 'shotgun' gene synthesis" Nucl. Acids Res. 13: 3305-3316), double-strand break repair (Mandecki (1986); Arnold (1993) "Protein engineering for unusual environments" Current Opinion in Biotechnology 4:450-455. "Oligonucleotide-directed double-strand break repair in plasmids of *Escherichia coli*: a method for site-specific mutagenesis" Proc. Natl. Acad. Sci. USA, 83:7177-7181). Additional details on many of the above methods can be found in Methods in Enzymology Volume 154, which also describes useful controls for trouble-shooting problems with various mutagenesis methods.

See also U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in Vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination."

Certain U.S. applications provide additional details regarding various diversity generating methods, including "SHUFFLING OF CODON ALTERED GENES" by Patten et al. filed Sep. 28, 1999, (U.S. Ser. No. 09/407,800); "EVOLUTION OF WHOLE CELLS AND ORGANISMS BY RECURSIVE SEQUENCE RECOMBINATION" by del Cardayre et al., filed Jul. 15, 1998 (U.S. Ser. No. 09/166,188), and Jul. 15, 1999 (U.S. Ser. No. 09/354,922); "OLIGONUCLEOTIDE MEDIATED NUCLEIC ACID RECOMBINATION" by Crameri et al., filed Sep. 28, 1999 (U.S. Ser. No. 09/408,392), and "OLIGONUCLEOTIDE MEDIATED NUCLEIC ACID RECOMBINATION" by Crameri et al., filed Jan. 18, 2000 (PCT/US00/01203); "USE OF CODON-VARIED OLIGONUCLEOTIDE SYNTHESIS FOR SYNTHETIC SHUFFLING" by Welch et al., filed Sep. 28, 1999 (U.S. Ser. No. 09/408,393); "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) and, e.g. "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579); "METHODS OF POPULATING DATA STRUCTURES FOR USE IN EVOLUTIONARY SIMULATIONS" by Selifonov and Stemmer, filed Jan. 18, 2000 (PCT/US00/01138); and "SINGLE-STRANDED NUCLEIC ACID TEMPLATE-MEDIATED RECOMBINATION AND NUCLEIC ACID FRAGMENT ISOLATION" by Affholter, filed Sep. 6, 2000 (U.S. Ser. No. 09/656,549).

Non-stochastic, or "directed evolution," methods include, e.g., saturation mutagenesis (GSSM), synthetic ligation reassembly (SLR), or a combination thereof are used to modify the nucleic acids of the invention to generate aldolases with new or altered properties (e.g., activity under highly acidic or alkaline conditions, high temperatures, and the like). Polypeptides encoded by the modified nucleic acids can be screened for an activity before testing for an aldolase or other activity. Any testing modality or protocol can be used, e.g., using a capillary array platform. See, e.g., U.S. Pat. Nos. 6,280,926; 5,939,250.

Saturation Mutagenesis, or, GSSM

In one aspect of the invention, non-stochastic gene modification, a "directed evolution process," is used to generate aldolases with new or altered properties. Variations of this method have been termed "gene site-saturation mutagenesis," "site-saturation mutagenesis," "saturation mutagenesis" or simply "GSSM." It can be used in combination with other mutagenization processes. See, e.g., U.S. Pat. Nos. 6,171,820; 6,238,884. In one aspect, GSSM comprises providing a template polynucleotide and a plurality of oligonucleotides, wherein each oligonucleotide comprises a sequence homologous to the template polynucleotide, thereby targeting a specific sequence of the template polynucleotide, and a sequence that is a variant of the homologous gene; generating progeny polynucleotides comprising non-stochastic sequence variations by replicating the template polynucleotide with the oligonucleotides, thereby generating polynucleotides comprising homologous gene sequence variations.

In one aspect, codon primers containing a degenerate N,N,G/T sequence are used to introduce point mutations into a polynucleotide, so as to generate a set of progeny polypeptides in which a full range of single amino acid substitutions is represented at each amino acid position, e.g., an amino acid residue in an enzyme active site or ligand binding site targeted to be modified. These oligonucleotides can comprise a contiguous first homologous sequence, a degenerate N,N,G/T sequence, and, optionally, a second homologous sequence. The downstream progeny translational products from the use of such oligonucleotides include all possible amino acid changes at each amino acid site along the polypeptide, because the degeneracy of the N,N,G/T sequence includes codons for all 20 amino acids. In one aspect, one such degenerate oligonucleotide (comprised of, e.g., one degenerate N,N,G/T cassette) is used for subjecting each original codon in a parental polynucleotide template to a full range of codon substitutions. In another aspect, at least two degenerate cassettes are used—either in the same oligonucleotide or not, for subjecting at least two original codons in a parental polynucleotide template to a full range of codon substitutions. For example, more than one N,N,G/T sequence can be contained in one oligonucleotide to introduce amino acid mutations at more than one site. This plurality of N,N,G/T sequences can be directly contiguous, or separated by one or more additional nucleotide sequence(s). In another aspect, oligonucleotides serviceable for introducing additions and deletions can be used either alone or in combination with the codons containing an N,N,G/T sequence, to introduce any combination or permutation of amino acid additions, deletions, and/or substitutions.

In one aspect, simultaneous mutagenesis of two or more contiguous amino acid positions is done using an oligonucleotide that contains contiguous N,N,G/T triplets, i.e. a degenerate (N,N,G/T)n sequence. In another aspect, degenerate cassettes having less degeneracy than the N,N,G/T sequence are used. For example, it may be desirable in some instances to use (e.g. in an oligonucleotide) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g. in an oligo) a degenerate N,N,N triplet sequence.

In one aspect, use of degenerate triplets (e.g., N,N,G/T triplets) allows for systematic and easy generation of a full range of possible natural amino acids (for a total of 20 amino acids) into each and every amino acid position in a polypeptide (in alternative aspects, the methods also include generation of less than all possible substitutions per amino acid residue, or codon, position). For example, for a 100 amino acid polypeptide, 2000 distinct species (i.e. 20 possible amino acids per position X 100 amino acid positions) can be generated. Through the use of an oligonucleotide or set of oligonucleotides containing a degenerate N,N,G/T triplet, 32 individual sequences can code for all 20 possible natural amino acids. Thus, in a reaction vessel in which a parental polynucleotide sequence is subjected to saturation mutagenesis using at least one such oligonucleotide, there are generated 32 distinct progeny polynucleotides encoding 20 distinct polypeptides. In contrast, the use of a non-degenerate oligonucleotide in site-directed mutagenesis leads to only one progeny polypeptide product per reaction vessel. Nondegenerate oligonucleotides can optionally be used in combination with degenerate primers disclosed; for example, nondegenerate oligonucleotides can be used to generate specific point mutations in a working polynucleotide. This provides one means to generate specific silent point mutations, point mutations leading to corresponding amino acid changes, and point mutations that cause the generation of stop codons and the corresponding expression of polypeptide fragments.

In one aspect, each saturation mutagenesis reaction vessel contains polynucleotides encoding at least 20 progeny polypeptide (e.g., aldolase) molecules such that all 20 natural amino acids are represented at the one specific amino acid position corresponding to the codon position mutagenized in the parental polynucleotide (other aspects use less than all 20 natural combinations). The 32-fold degenerate progeny polypeptides generated from each saturation mutagenesis reaction vessel can be subjected to clonal amplification (e.g. cloned into a suitable host, e.g., *E. coli* host, using, e.g., an expression vector) and subjected to expression screening. When an individual progeny polypeptide is identified by screening to display a favorable change in property (when compared to the parental polypeptide, such as increased aldolase activity under alkaline or acidic conditions), it can be sequenced to identify the correspondingly favorable amino acid substitution contained therein.

In one aspect, upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e. 2 at each of three positions) and no change at any position.

In another aspect, site-saturation mutagenesis can be used together with another stochastic or non-stochastic means to vary sequence, e.g., synthetic ligation reassembly (see below), shuffling, chimerization, recombination and other mutagenizing processes and mutagenizing agents. This invention provides for the use of any mutagenizing process (es), including saturation mutagenesis, in an iterative manner.

Synthetic Ligation Reassembly (SLR)

The invention provides a non-stochastic gene modification system termed "synthetic ligation reassembly," or simply "SLR," a "directed evolution process," to generate aldolases with new or altered properties. SLR is a method of ligating oligonucleotide fragments together non-stochastically. This method differs from stochastic oligonucleotide shuffling in that the nucleic acid building blocks are not shuffled, concatenated or chimerized randomly, but rather are assembled non-stochastically. See, e.g., U.S. Ser. No. 09/332,835 entitled "Synthetic Ligation Reassembly in Directed Evolution" and filed on Jun. 14, 1999 ("U.S. Ser. No. 09/332,835"). In one aspect, SLR comprises the following steps: (a) providing a template polynucleotide, wherein the template polynucleotide comprises sequence encoding a homologous gene; (b) providing a plurality of building block polynucleotides, wherein the building block polynucleotides are designed to cross-over reassemble with the template polynucleotide at a predetermined sequence, and a building block polynucleotide comprises a sequence that is a variant of the homologous gene and a sequence homologous to the template polynucleotide flanking the variant sequence; (c) combining a building block polynucleotide with a template polynucleotide such that the building block polynucleotide cross-over reassembles with the template polynucleotide to generate polynucleotides comprising homologous gene sequence variations.

SLR does not depend on the presence of high levels of homology between polynucleotides to be rearranged. Thus, this method can be used to non-stochastically generate libraries (or sets) of progeny molecules comprised of over $10^{100}$ different chimeras. SLR can be used to generate libraries comprised of over $10^{1000}$ different progeny chimeras. Thus, aspects of the present invention include non-stochastic methods of producing a set of finalized chimeric nucleic acid molecule shaving an overall assembly order that is chosen by design. This method includes the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus the overall assembly order in which the nucleic acid building blocks can be coupled is specified by the design of the ligatable ends. If more than one assembly step is to be used, then the overall assembly order in which the nucleic acid building blocks can be coupled is also specified by the sequential order of the assembly step(s). In one aspect, the annealed building pieces are treated with an enzyme, such as a ligase (e.g. T4 DNA ligase), to achieve covalent bonding of the building pieces.

In one aspect, the design of the oligonucleotide building blocks is obtained by analyzing a set of progenitor nucleic acid sequence templates that serve as a basis for producing a progeny set of finalized chimeric polynucleotides. These parental oligonucleotide templates thus serve as a source of sequence information that aids in the design of the nucleic acid building blocks that are to be mutagenized, e.g., chimerized or shuffled.

In one aspect of this method, the sequences of a plurality of parental nucleic acid templates are aligned in order to select one or more demarcation points. The demarcation points can be located at an area of homology, and are comprised of one or more nucleotides. These demarcation points are preferably shared by at least two of the progenitor templates. The demarcation points can thereby be used to delineate the boundaries of oligonucleotide building blocks to be generated in order to rearrange the parental polynucleotides. The demarcation points identified and selected in the progenitor molecules serve as potential chimerization points in the assembly of the final chimeric progeny molecules. A demarcation point can be an area of homology (comprised of at least one homologous nucleotide base) shared by at least two parental polynucleotide sequences. Alternatively, a demarcation point can be an area of homology that is shared by at least half of the parental polynucleotide sequences, or, it can be an area of homology that is shared by at least two thirds of the parental polynucleotide sequences. Even more preferably a serviceable demarcation points is an area of homology that is shared by at least three fourths of the parental polynucleotide sequences, or, it can be shared by at almost all of the parental polynucleotide sequences. In one aspect, a demarcation point is an area of homology that is shared by all of the parental polynucleotide sequences.

In one aspect, a ligation reassembly process is performed exhaustively in order to generate an exhaustive library of progeny chimeric polynucleotides. In other words, all possible ordered combinations of the nucleic acid building blocks are represented in the set of finalized chimeric nucleic acid molecules. At the same time, in another embodiment, the assembly order (i.e. the order of assembly of each building block in the 5' to 3 sequence of each finalized chimeric nucleic acid) in each combination is by design (or non-stochastic) as described above. Because of the non-stochastic nature of this invention, the possibility of unwanted side products is greatly reduced.

In another aspect, the ligation reassembly method is performed systematically. For example, the method is performed in order to generate a systematically compartmentalized library of progeny molecules, with compartments that can be screened systematically, e.g. one by one. In other words this invention provides that, through the selective and judicious use of specific nucleic acid building blocks, coupled with the selective and judicious use of sequentially stepped assembly reactions, a design can be achieved where specific sets of progeny products are made in each of several reaction vessels. This allows a systematic examination and screening procedure to be performed. Thus, these methods allow a potentially very large number of progeny molecules to be examined systematically in smaller groups. Because of its ability to perform chimerizations in a manner that is highly flexible yet exhaustive and systematic as well, particularly when there is a low level of homology among the progenitor molecules, these methods provide for the generation of a library (or set) comprised of a large number of progeny molecules. Because of the non-stochastic nature of the instant ligation reassembly invention, the progeny molecules generated preferably comprise a library of finalized chimeric nucleic acid molecules having an overall assembly order that is chosen by design. The saturation mutagenesis and optimized directed evolution methods also can be used to generate different progeny molecular species. It is appreciated that the invention provides freedom of choice and control regarding the selection of demarcation points, the size and number of the nucleic acid building blocks, and the size and design of the couplings. It is appreciated, furthermore, that the requirement for intermolecular homology is highly relaxed for the operability of this invention. In fact, demarcation points can even be chosen in areas of little or no intermolecular homology. For example, because of codon wobble, i.e. the degeneracy of codons, nucleotide substitutions can be introduced into nucleic acid building blocks without altering the amino acid originally encoded in the corresponding progenitor template. Alternatively, a codon can be altered such that the coding for an originally amino acid is altered. This invention provides that such substitutions can be introduced into the nucleic acid building block in order to increase the incidence of intermolecularly homologous demarcation points and thus to allow an increased number of couplings to be achieved among the building blocks, which in turn allows a greater number of progeny chimeric molecules to be generated.

In another aspect, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g. by mutagenesis) or in an in vivo process (e.g. by utilizing the gene splicing ability of a host organism). It is appreciated that in many instances the introduction of these nucleotides may also be desirable for many other reasons in addition to the potential benefit of creating a serviceable demarcation point.

In one aspect, a nucleic acid building block is used to introduce an intron. Thus, functional introns are introduced into a man-made gene manufactured according to the methods described herein. The artificially introduced intron(s) can be functional in a host cells for gene splicing much in the way that naturally-occurring introns serve functionally in gene splicing.

Optimized Directed Evolution System

The invention provides a non-stochastic gene modification system termed "optimized directed evolution system" to generate aldolases with new or altered properties. Optimized directed evolution is directed to the use of repeated cycles of reductive reassortment, recombination and selection that allow for the directed molecular evolution of nucleic acids through recombination. Optimized directed evolution allows generation of a large population of evolved chimeric sequences, wherein the generated population is significantly enriched for sequences that have a predetermined number of crossover events.

A crossover event is a point in a chimeric sequence where a shift in sequence occurs from one parental variant to another parental variant. Such a point is normally at the juncture of where oligonucleotides from two parents are ligated together to form a single sequence. This method allows calculation of the correct concentrations of oligonucleotide sequences so that the final chimeric population of sequences is enriched for the chosen number of crossover events. This provides more control over choosing chimeric variants having a predetermined number of crossover events.

In addition, this method provides a convenient means for exploring a tremendous amount of the possible protein variant space in comparison to other systems. Previously, if one generated, for example, $10^{13}$ chimeric molecules during a reaction, it would be extremely difficult to test such a high number of chimeric variants for a particular activity. Moreover, a significant portion of the progeny population would have a very high number of crossover events which resulted in proteins that were less likely to have increased levels of a particular activity. By using these methods, the population of chimerics molecules can be enriched for those variants that have a particular number of crossover events. Thus, although one can still generate $10^{13}$ chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

One method for creating a chimeric progeny polynucleotide sequence is to create oligonucleotides corresponding to fragments or portions of each parental sequence. Each oligonucleotide preferably includes a unique region of overlap so that mixing the oligonucleotides together results in a new variant that has each oligonucleotide fragment assembled in the correct order. Additional information can also be found in U.S. Ser. No. 09/332,835. The number of oligonucleotides generated for each parental variant bears a relationship to the total number of resulting crossovers in the chimeric molecule that is ultimately created. For example, three parental nucleotide sequence variants might be provided to undergo a ligation reaction in order to find a chimeric variant having, for example, greater activity at high temperature. As one example, a set of 50 oligonucleotide sequences can be generated corresponding to each portions of each parental variant. Accordingly, during the ligation reassembly process there could be up to 50 crossover events within each of the chimeric sequences. The probability that each of the generated chimeric polynucleotides will contain oligonucleotides from each parental variant in alternating order is very low. If each oligonucleotide fragment is present in the ligation reaction in the same molar quantity it is likely that in some positions oligonucleotides from the same parental polynucleotide will ligate next to one another and thus not result in a crossover event. If the concentration of each oligonucleotide from each parent is kept constant during any ligation step in this example, there is a ⅓ chance (assuming 3 parents) that an oligonucleotide from the same parental variant will ligate within the chimeric sequence and produce no crossover.

Accordingly, a probability density function (PDF) can be determined to predict the population of crossover events that are likely to occur during each step in a ligation reaction given a set number of parental variants, a number of oligonucleotides corresponding to each variant, and the concentrations of each variant during each step in the ligation reaction. The statistics and mathematics behind determining the PDF is described below. By utilizing these methods, one can calculate such a probability density function, and thus enrich the chimeric progeny population for a predetermined number of crossover events resulting from a particular ligation reaction. Moreover, a target number of crossover events can be predetermined, and the system then programmed to calculate the starting quantities of each parental oligonucleotide during each step in the ligation reaction to result in a probability density function that centers on the predetermined number of crossover events. These methods are directed to the use of repeated cycles of reductive reassortment, recombination and selection that allow for the directed molecular evolution of a nucleic acid encoding an polypeptide through recombination. This system allows generation of a large population of evolved chimeric sequences, wherein the generated population is significantly enriched for sequences that have a predetermined number of crossover events. A crossover event is a point in a chimeric sequence where a shift in sequence occurs from one parental variant to another parental variant. Such a point is normally at the juncture of where oligonucleotides from two parents are ligated together to form a single sequence. The method allows calculation of the correct concentrations of oligonucleotide sequences so that the final chimeric population of sequences is enriched for the chosen number of crossover events. This provides more control over choosing chimeric variants having a predetermined number of crossover events.

In addition, these methods provide a convenient means for exploring a tremendous amount of the possible protein variant space in comparison to other systems. By using the methods described herein, the population of chimerics molecules can be enriched for those variants that have a particular number of crossover events. Thus, although one can still generate $10^{13}$ chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

In one aspect, the method creates a chimeric progeny polynucleotide sequence by creating oligonucleotides corresponding to fragments or portions of each parental sequence. Each oligonucleotide preferably includes a unique region of overlap so that mixing the oligonucleotides together results in a new variant that has each oligonucleotide fragment assembled in the correct order. See also U.S. Ser. No. 09/332, 835.

The number of oligonucleotides generated for each parental variant bears a relationship to the total number of resulting crossovers in the chimeric molecule that is ultimately created. For example, three parental nucleotide sequence variants might be provided to undergo a ligation reaction in order to find a chimeric variant having, for example, greater activity at high temperature. As one example, a set of 50 oligonucleotide sequences can be generated corresponding to each portions of each parental variant. Accordingly, during the ligation reassembly process there could be up to 50 crossover events within each of the chimeric sequences. The probability that each of the generated chimeric polynucleotides will contain oligonucleotides from each parental variant in alternating order is very low. If each oligonucleotide fragment is present in the ligation reaction in the same molar quantity it is likely that in some positions oligonucleotides from the same parental polynucleotide will ligate next to one another and thus not result in a crossover event. If the concentration of each oligonucleotide from each parent is kept constant during any ligation step in this example, there is a ⅓ chance (assuming 3 parents) that a oligonucleotide from the same parental variant will ligate within the chimeric sequence and produce no crossover.

Accordingly, a probability density function (PDF) can be determined to predict the population of crossover events that are likely to occur during each step in a ligation reaction given a set number of parental variants, a number of oligonucleotides corresponding to each variant, and the concentrations of each variant during each step in the ligation reaction. The statistics and mathematics behind determining the PDF is described below. One can calculate such a probability density function, and thus enrich the chimeric progeny population for a predetermined number of crossover events resulting from a particular ligation reaction. Moreover, a target number of crossover events can be predetermined, and the system then programmed to calculate the starting quantities of each parental oligonucleotide during each step in the ligation reaction to result in a probability density function that centers on the predetermined number of crossover events.

Determining Crossover Events

Embodiments of the invention include a system and software that receive a desired crossover probability density function (PDF), the number of parent genes to be reassembled, and the number of fragments in the reassembly as inputs. The output of this program is a "fragment PDF" that can be used to determine a recipe for producing reassembled genes, and the estimated crossover PDF of those genes. The processing described herein is preferably performed in MATLAB® (The Mathworks, Natick, Mass.) a programming language and development environment for technical computing.

Iterative Processes

In practicing the invention, these processes can be iteratively repeated. For example a nucleic acid (or, the nucleic acid) responsible for an altered aldolase phenotype is identified, re-isolated, again modified, re-tested for activity. This process can be iteratively repeated until a desired phenotype is engineered. For example, an entire biochemical anabolic or catabolic pathway can be engineered into a cell, including aldolase activity.

Similarly, if it is determined that a particular oligonucleotide has no affect at all on the desired trait (e.g., a new aldolase phenotype), it can be removed as a variable by synthesizing larger parental oligonucleotides that include the sequence to be removed. Since incorporating the sequence within a larger sequence prevents any crossover events, there will no longer be any variation of this sequence in the progeny polynucleotides. This iterative practice of determining which oligonucleotides are most related to the desired trait, and which are unrelated, allows more efficient exploration all of the possible protein variants that might be provide a particular trait or activity.

In Vivo Shuffling

In vivo shuffling of molecules is use in methods of the invention that provide variants of polypeptides of the invention, e.g., antibodies, aldolase enzymes, and the like. In vivo shuffling can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In one aspect, the invention provides a method for producing a hybrid polynucleotide from at least a first polynucleotide and a second polynucleotide. The invention can be used to produce a hybrid polynucleotide by introducing at least a first polynucleotide and a second polynucleotide which share at least one region of partial sequence homology into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

Producing Sequence Variants

The invention also provides methods of making sequence variants of the nucleic acid and polypeptide (e.g., aldolase) sequences of the invention or isolating aldolase sequence variants using the nucleic acids and polypeptides of the invention. In one aspect, the invention provides for variants of an aldolase gene of the invention, which can be altered by any means, including, e.g., random or stochastic methods, or, non-stochastic, or "directed evolution," methods, as described above.

The isolated variants may be naturally occurring. Variant can also be created in vitro. Variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures. Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. These nucleotide differences can result in amino acid changes with respect to the polypeptides encoded by the nucleic acids from the natural isolates.

For example, variants may be created using error prone PCR. In error prone PCR, PCR is performed under conditions where the copying fidelity of the DNA polymerase is low, such that a high rate of point mutations is obtained along the entire length of the PCR product. Error prone PCR is described, e.g., in Leung, D. W., et al., Technique, 1:11-15, 1989) and Caldwell, R. C. & Joyce G. F., PCR Methods Applic., 2:28-33, 1992. Briefly, in such procedures, nucleic acids to be mutagenized are mixed with PCR primers, reaction buffer, MgCl2, MnCl2, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM MgCl2, 0.5 mM MnCl2, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids is evaluated.

Variants may also be created using oligonucleotide directed mutagenesis to generate site-specific mutations in any cloned DNA of interest. Oligonucleotide mutagenesis is described, e.g., in Reidhaar-Olson (1988) Science 241:53-57. Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, e.g., U.S. Pat. No. 5,965,408.

Still another method of generating variants is sexual PCR mutagenesis. In sexual PCR mutagenesis, forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described, e.g., in Stemmer (1994) Proc. Natl. Acad. Sci. USA 91:10747-10751. Briefly, in such procedures a plurality of nucleic acids to be recombined are digested with DNase to generate fragments having an average size of 50-200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10-30 ng/µl in a solution of 0.2 mM of each dNTP, 2.2 mM $MgCl_2$, 50 mM KCL, 10 mM Tris HCl, pH 9.0, and 0.1% Triton X-100. 2.5 units of Taq polymerase per 100:1 of reaction mixture is added and PCR is performed using the following regime: 94° C. for 60 seconds, 94° C. for 30 seconds, 50-55° C. for 30 seconds, 72° C. for 30 seconds (30-45 times) and 72° C. for 5 minutes. However, it will be appreciated that these parameters may be varied as appropriate. In some aspects, oligonucleotides may be included in the PCR reactions. In other aspects, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

Variants may also be created by in vivo mutagenesis. In some embodiments, random mutations in a sequence of interest are generated by propagating the sequence of interest in a bacterial strain, such as an *E. coli* strain, which carries mutations in one or more of the DNA repair pathways. Such "mutator" strains have a higher random mutation rate than that of a wild-type parent. Propagating the DNA in one of these strains will eventually generate random mutations within the DNA. Mutator strains suitable for use for in vivo mutagenesis are described, e.g., in PCT Publication No. WO 91/16427.

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described, e.g., in Arkin (1992) Proc. Natl. Acad. Sci. USA 89:7811-7815.

In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described, e.g., in Delegrave (1993) Biotechnology Res. 11: 1548-1552. Random and site-directed mutagenesis are described, e.g., in Arnold (1993) Current Opinion in Biotechnology 4:450-455.

In some embodiments, the variants are created using shuffling procedures wherein portions of a plurality of nucleic acids which encode distinct polypeptides are fused together to create chimeric nucleic acid sequences which encode chimeric polypeptides as described in, e.g., U.S. Pat. Nos. 5,965, 408; 5,939,250.

The invention also provides variants of polypeptides of the invention comprising sequences in which one or more of the amino acid residues (e.g., of an exemplary polypeptide of the invention) are substituted with a conserved or non-conserved amino acid residue (e.g., a conserved amino acid residue) and such substituted amino acid residue may or may not be one encoded by the genetic code. Conservative substitutions are those that substitute a given amino acid in a polypeptide by another amino acid of like characteristics. Thus, polypeptides of the invention include those with conservative substitutions of sequences of the invention, including but not limited to the following replacements: replacements of an aliphatic amino acid such as Alanine, Valine, Leucine and Isoleucine with another aliphatic amino acid; replacement of a Serine with a Threonine or vice versa; replacement of an acidic residue such as Aspartic acid and Glutamic acid with another acidic residue; replacement of a residue bearing an amide group, such as Asparagine and Glutamine, with another residue bearing an amide group; exchange of a basic residue such as Lysine and Arginine with another basic residue; and replacement of an aromatic residue such as Phenylalanine, Tyrosine with another aromatic residue. Other variants are those in which one or more of the amino acid residues of the polypeptides of the invention includes a substituent group.

Other variants within the scope of the invention are those in which the polypeptide is associated with another compound, such as a compound to increase the half-life of the polypeptide, for example, polyethylene glycol.

Additional variants within the scope of the invention are those in which additional amino acids are fused to the polypeptide, such as a leader sequence, a secretory sequence, a proprotein sequence or a sequence which facilitates purification, enrichment, or stabilization of the polypeptide.

In some aspects, the variants, fragments, derivatives and analogs of the polypeptides of the invention retain the same biological function or activity as the exemplary polypeptides, e.g., an aldolase activity, as described herein. In other aspects, the variant, fragment, derivative, or analog includes a proprotein, such that the variant, fragment, derivative, or analog can be activated by cleavage of the proprotein portion to produce an active polypeptide.

Optimizing Codons to Achieve High Levels of Protein Expression in Host Cells

The invention provides methods for modifying aldolase-encoding nucleic acids to modify codon usage. In one aspect, the invention provides methods for modifying codons in a nucleic acid encoding an aldolase to increase or decrease its expression in a host cell. The invention also provides nucleic acids encoding an aldolase modified to increase its expression in a host cell, aldolase enzymes so modified, and methods of making the modified aldolase enzymes. The method comprises identifying a "non-preferred" or a "less preferred" codon in aldolase-encoding nucleic acid and replacing one or more of these non-preferred or less preferred codons with a "preferred codon" encoding the same amino acid as the replaced codon and at least one non-preferred or less preferred codon in the nucleic acid has been replaced by a preferred codon encoding the same amino acid. A preferred codon is a codon over-represented in coding sequences in genes in the host cell and a non-preferred or less preferred codon is a codon under-represented in coding sequences in genes in the host cell.

Host cells for expressing the nucleic acids, expression cassettes and vectors of the invention include bacteria, yeast, fungi, plant cells, insect cells and mammalian cells. Thus, the invention provides methods for optimizing codon usage in all of these cells, codon-altered nucleic acids and polypeptides made by the codon-altered nucleic acids. Exemplary host cells include gram negative bacteria, such as *Escherichia coli* and *Pseudomonas fluorescens*; gram positive bacteria, such as *Streptomyces diversa, Lactobacillus gasseri, Lactococcus lactis, Lactococcus cremoris, Bacillus subtilis*. Exemplary host cells also include eukaryotic organisms, e.g., various yeast, such as *Saccharomyces* sp., including *Saccharomyces cerevisiae, Schizosaccharomyces pombe, Pichia pastoris,* and *Kluyveromyces lactis, Hansenula polymorpha, Aspergillus niger*, and mammalian cells and cell lines and insect cells and cell lines. Thus, the invention also includes nucleic acids and polypeptides optimized for expression in these organisms and species.

For example, the codons of a nucleic acid encoding an aldolase isolated from a bacterial cell are modified such that the nucleic acid is optimally expressed in a bacterial cell different from the bacteria from which the aldolase was derived, a yeast, a fungi, a plant cell, an insect cell or a mammalian cell. Methods for optimizing codons are well known in the art, see, e.g., U.S. Pat. No. 5,795,737; Baca (2000) Int. J. Parasitol. 30:113-118; Hale (1998) Protein Expr. Purif. 12:185-188; Narum (2001) Infect. Immun. 69:7250-7253. See also Narum (2001) Infect. Immun. 69:7250-7253, describing optimizing codons in mouse systems; Outchkourov (2002) Protein Expr. Purif. 24:18-24, describing optimizing codons in yeast; Feng (2000) Biochemistry 39:15399-15409, describing optimizing codons in *E. coli*; Humphreys (2000) Protein Expr. Purif. 20:252-264, describing optimizing codon usage that affects secretion in *E. coli*.

Transgenic Non-Human Animals

The invention provides transgenic non-human animals comprising a nucleic acid, a polypeptide, an expression cassette or vector or a transfected or transformed cell of the invention. The transgenic non-human animals can be, e.g., goats, rabbits, sheep, pigs, cows, rats and mice, comprising the nucleic acids of the invention. These animals can be used, e.g., as in vivo models to study aldolase activity, or, as models to screen for modulators of aldolase activity in vivo. The coding sequences for the polypeptides to be expressed in the transgenic non-human animals can be designed to be constitutive, or, under the control of tissue-specific, developmental-specific or inducible transcriptional regulatory factors. Transgenic non-human animals can be designed and generated using any method known in the art; see, e.g., U.S. Pat. Nos. 6,211,428; 6,187,992; 6,156,952; 6,118,044; 6,111,166; 6,107,541; 5,959,171; 5,922,854; 5,892,070; 5,880,327; 5,891,698; 5,639,940; 5,573,933; 5,387,742; 5,087,571, describing making and using transformed cells and eggs and transgenic mice, rats, rabbits, sheep, pigs and cows. See also, e.g., Pollock (1999) J. Immunol. Methods 231:147-157, describing the production of recombinant proteins in the milk of transgenic dairy animals; Baguisi (1999) Nat. Biotechnol. 17:456-461, demonstrating the production of transgenic goats. U.S. Pat. No. 6,211,428, describes making and using transgenic non-human mammals which express in their brains a nucleic acid construct comprising a DNA sequence. U.S. Pat. No. 5,387,742, describes injecting cloned recombinant or synthetic DNA sequences into fertilized mouse eggs, implanting the injected eggs in pseudo-pregnant females, and growing to term transgenic mice whose cells express proteins related to the pathology of Alzheimer's disease. U.S. Pat. No. 6,187,992, describes making and using a transgenic mouse whose genome comprises a disruption of the gene encoding amyloid precursor protein (APP).

"Knockout animals" can also be used to practice the methods of the invention. For example, in one aspect, the transgenic or modified animals of the invention comprise a "knockout animal," e.g., a "knockout mouse," engineered not to express or to be unable to express an aldolase.

Transgenic Plants and Seeds

The invention provides transgenic plants and seeds comprising a nucleic acid, a polypeptide (e.g., an aldolase), an expression cassette or vector or a transfected or transformed cell of the invention. The invention also provides plant products, e.g., oils, seeds, leaves, extracts and the like, comprising a nucleic acid and/or a polypeptide (e.g., an aldolase) of the invention. The transgenic plant can be dicotyledonous (a dicot) or monocotyledonous (a monocot). The invention also provides methods of making and using these transgenic plants and seeds. The transgenic plant or plant cell expressing a polypeptide of the invention may be constructed in accordance with any method known in the art. See, for example, U.S. Pat. No. 6,309,872.

Nucleic acids and expression constructs of the invention can be introduced into a plant cell by any means. For example, nucleic acids or expression constructs can be introduced into the genome of a desired plant host, or, the nucleic acids or expression constructs can be episomes. Introduction into the genome of a desired plant can be such that the host's aldolase production is regulated by endogenous transcriptional or translational control elements. The invention also provides "knockout plants" where insertion of gene sequence by, e.g., homologous recombination, has disrupted the expression of the endogenous gene. Means to generate "knockout" plants are well-known in the art, see, e.g., Strepp (1998) Proc Natl. Acad. Sci. USA 95:4368-4373; Miao (1995) Plant J 7:359-365. See discussion on transgenic plants, below.

The nucleic acids of the invention can be used to confer desired traits on essentially any plant, e.g., on oil-seed containing plants, such as soybeans, rapeseed, sunflower seeds, sesame and peanuts. Nucleic acids of the invention can be used to manipulate metabolic pathways of a plant in order to optimize or alter host's expression of aldolase. The can change aldolase activity in a plant. Alternatively, an aldolase of the invention can be used in production of a transgenic plant to produce a compound not naturally produced by that plant. This can lower production costs or create a novel product.

In one aspect, the first step in production of a transgenic plant involves making an expression construct for expression in a plant cell. These techniques are well known in the art. They can include selecting and cloning a promoter, a coding sequence for facilitating efficient binding of ribosomes to mRNA and selecting the appropriate gene terminator sequences. One exemplary constitutive promoter is CaMV35S, from the cauliflower mosaic virus, which generally results in a high degree of expression in plants. Other promoters are more specific and respond to cues in the plant's internal or external environment. An exemplary light-inducible promoter is the promoter from the cab gene, encoding the major chlorophyll a/b binding protein.

In one aspect, the nucleic acid is modified to achieve greater expression in a plant cell. For example, a sequence of the invention is likely to have a higher percentage of A-T nucleotide pairs compared to that seen in a plant, some of which prefer G-C nucleotide pairs. Therefore, A-T nucleotides in the coding sequence can be substituted with G-C nucleotides without significantly changing the amino acid sequence to enhance production of the gene product in plant cells.

Selectable marker gene can be added to the gene construct in order to identify plant cells or tissues that have successfully integrated the transgene. This may be necessary because achieving incorporation and expression of genes in plant cells is a rare event, occurring in just a few percent of the targeted tissues or cells. Selectable marker genes encode proteins that provide resistance to agents that are normally toxic to plants, such as antibiotics or herbicides. Only plant cells that have integrated the selectable marker gene will survive when grown on a medium containing the appropriate antibiotic or herbicide. As for other inserted genes, marker genes also require promoter and termination sequences for proper function.

In one aspect, making transgenic plants or seeds comprises incorporating sequences of the invention and, optionally, marker genes into a target expression construct (e.g., a plasmid), along with positioning of the promoter and the terminator sequences. This can involve transferring the modified gene into the plant through a suitable method. For example, a construct may be introduced directly into the genomic DNA of the plant cell using techniques such as electroporation and microinjection of plant cell protoplasts, or the constructs can be introduced directly to plant tissue using ballistic methods, such as DNA particle bombardment. For example, see, e.g., Christou (1997) Plant Mol. Biol. 35:197-203; Pawlowski (1996) Mol. Biotechnol. 6:17-30; Klein (1987) Nature 327: 70-73; Takumi (1997) Genes Genet. Syst. 72:63-69, discussing use of particle bombardment to introduce transgenes into wheat; and Adam (1997) supra, for use of particle bombardment to introduce YACs into plant cells. For example, Rinehart (1997) supra, used particle bombardment to generate transgenic cotton plants. Apparatus for accelerating particles is described U.S. Pat. No. 5,015,580; and, the commercially available BioRad (Biolistics) PDS-2000 particle acceleration instrument; see also, John, U.S. Pat. No. 5,608,148; and Ellis, U.S. Pat. No. 5,681,730, describing particle-mediated transformation of gymnosperms.

In one aspect, protoplasts can be immobilized and injected with nucleic acids, e.g., an expression construct. Although plant regeneration from protoplasts is not easy with cereals, plant regeneration is possible in legumes using somatic embryogenesis from protoplast derived callus. Organized tissues can be transformed with naked DNA using gene gun technique, where DNA is coated on tungsten microprojectiles, shot 1/100th the size of cells, which carry the DNA deep into cells and organelles. Transformed tissue is then induced to regenerate, usually by somatic embryogenesis. This technique has been successful in several cereal species including maize and rice.

Nucleic acids, e.g., expression constructs, can also be introduced in to plant cells using recombinant viruses. Plant cells can be transformed using viral vectors, such as, e.g., tobacco mosaic virus derived vectors (Rouwendal (1997) Plant Mol. Biol. 33:989-999), see Porta (1996) "Use of viral replicons for the expression of genes in plants," Mol. Biotechnol. 5:209-221.

Alternatively, nucleic acids, e.g., an expression construct, can be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, e.g., Horsch (1984) Science 233:496-498; Fraley (1983) Proc. Natl. Acad. Sci. USA 80:4803 (1983); Gene Transfer to Plants, Potrykus, ed. (Springer-Verlag, Berlin 1995). The DNA in an *A. tumefaciens* cell is contained in the bacterial chromosome as well as in another structure known as a Ti (tumor-inducing) plasmid. The Ti plasmid contains a stretch of DNA termed T-DNA (~20 kb long) that is transferred to the plant cell in the infection process and a series of vir (virulence) genes that direct the infection process. *A. tumefaciens* can only infect a plant through wounds: when a plant root or stem is wounded it gives off certain chemical signals, in response to which, the vir genes of *A. tumefaciens* become activated and direct a series of events necessary for the transfer of the T-DNA from the Ti plasmid to the plant's chromosome. The T-DNA then enters the plant cell through the wound. One speculation is that the T-DNA waits until the plant DNA is being replicated or transcribed, then inserts itself into the exposed plant DNA. In order to use *A. tumefaciens* as a transgene vector, the tumor-inducing section of T-DNA have to be removed, while retaining the T-DNA border regions and the vir genes. The transgene is then inserted between the T-DNA border regions, where it is transferred to the plant cell and becomes integrated into the plant's chromosomes.

The invention provides for the transformation of monocotyledonous plants using the nucleic acids of the invention, including important cereals, see Hiei (1997) Plant Mol. Biol. 35:205-218. See also, e.g., Horsch, Science (1984) 233:496; Fraley (1983) Proc. Natl. Acad. Sci. USA 80:4803; Thykjaer (1997) supra; Park (1996) Plant Mol. Biol. 32:1135-1148, discussing T-DNA integration into genomic DNA. See also D'Halluin, U.S. Pat. No. 5,712,135, describing a process for the stable integration of a DNA comprising a gene that is functional in a cell of a cereal, or other monocotyledonous plant.

In one aspect, the third step can involve selection and regeneration of whole plants capable of transmitting the incorporated target gene to the next generation. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee (1987) Ann. Rev. of Plant Phys. 38:467-486. To obtain whole plants from transgenic tissues such as immature embryos, they can be grown under controlled environmental conditions in a series of media containing nutrients and hormones, a process known as tissue culture. Once whole plants are generated and produce seed, evaluation of the progeny begins.

After the expression cassette is stably incorporated in transgenic plants, it can be introduced into other plants by sexual crossing. Any of a number of standard breeding techniques can be used, depending upon the species to be crossed. Since transgenic expression of the nucleic acids of the invention leads to phenotypic changes, plants comprising the recombinant nucleic acids of the invention can be sexually crossed with a second plant to obtain a final product. Thus, the seed of the invention can be derived from a cross between two transgenic plants of the invention, or a cross between a plant of the invention and another plant. The desired effects (e.g., expression of the polypeptides of the invention to produce a plant in which flowering behavior is altered) can be enhanced when both parental plants express the polypeptides (e.g., an aldolase) of the invention. The desired effects can be passed to future plant generations by standard propagation means.

The nucleic acids and polypeptides of the invention are expressed in or inserted in any plant or seed. Transgenic plants of the invention can be dicotyledonous or monocotyledonous. Examples of monocot transgenic plants of the invention are grasses, such as meadow grass (blue grass, *Poa*), forage grass such as festuca, lolium, temperate grass, such as *Agrostis*, and cereals, e.g., wheat, oats, rye, barley, rice, sorghum, and maize (corn). Examples of dicot transgenic plants of the invention are tobacco, legumes, such as lupins, potato, sugar beet, pea, bean and soybean, and cruciferous plants (family Brassicaceae), such as cauliflower, rape seed, and the closely related model organism *Arabidopsis thaliana*. Thus, the transgenic plants and seeds of the invention include a broad range of plants, including, but not limited to, species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna*, and *Zea*.

In alternative embodiments, the nucleic acids of the invention are expressed in plants (e.g., as transgenic plants), such as oil-seed containing plants, e.g., soybeans, rapeseed, sunflower seeds, sesame and peanuts. The nucleic acids of the invention can be expressed in plants which contain fiber cells, including, e.g., cotton, silk cotton tree (Kapok, Ceiba pentandra), desert willow, creosote bush, winterfat, balsa, ramie, kenaf, hemp, roselle, jute, sisal abaca and flax. In alternative embodiments, the transgenic plants of the invention can be members of the genus *Gossypium*, including members of any *Gossypium* species, such as *G. arboreum; G. herbaceum, G. barbadense*, and *G. hirsutum*.

The invention also provides for transgenic plants to be used for producing large amounts of the polypeptides (e.g., an aldolase or antibody) of the invention. For example, see Palmgren (1997) Trends Genet. 13:348; Chong (1997) Transgenic Res. 6:289-296 (producing human milk protein beta-casein in transgenic potato plants using an auxin-inducible, bidirectional mannopine synthase (mas1',2') promoter with *Agrobacterium tumefaciens*-mediated leaf disc transformation methods).

Using known procedures, one of skill can screen for plants of the invention by detecting the increase or decrease of transgene mRNA or protein in transgenic plants. Means for detecting and quantitation of mRNAs or proteins are well known in the art.

Polypeptides and Peptides

The invention provides isolated or recombinant polypeptides having a sequence identity (e.g., at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity) to an exemplary sequence of the invention, e.g., SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30, or enzymatically active fragments thereof. As discussed above, the identity can be over the full length of the polypeptide, or, the identity can be over a subsequence thereof, e.g., a region of at least about 50, 60, 70, 80, 90, 100, 150, 200, 250, 300, 350, 400, 450, 500, 550, 600, 650, 700 or more residues. Polypeptides of the invention can also be shorter than the full length of exemplary polypeptides (e.g., SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30, or enzymatically active fragments thereof, etc.). In alternative embodiment, the invention provides polypeptides (peptides, fragments) ranging in size between about 5 and the full length of a polypeptide, e.g., a polypeptide of the invention having an aldolase activity, such as a aldolase enzyme; exemplary sizes being of about 5, 10, 15, 20, 25, 30, 35, 40, 45, 50, 55, 60, 65, 70, 75, 80, 85, 90, 100, 125, 150, 175, 200, 250, 300, 350, 400 or more residues, e.g., contiguous residues of the exemplary aldolases of the invention, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30, or enzymatically active fragments thereof, etc. Peptides of the invention can be useful as, e.g., labeling probes, antigens, toleragens, motifs, aldolase active sites.

In one aspect, the polypeptide has an aldolase activity. As used herein, aldolase activity includes any aldolase or lyase activity. The enzymes of the invention can have the activity of any aldolase or lyase. For example, the aldolases of the invention can catalyze C—C bond formation, and, in one aspect, in a highly stereoselective way. As another example, a polypeptide of the invention can have a 2-deoxyribose-5-phosphate aldolase (DERA) activity, which in one aspect comprises catalysis of the reversible aldol reaction between acetaldehyde and D-glyceraldehyde-3-phosphate to generate D-2-deoxyribose-5-phosphate. DERA aldolase activity of the invention can catalyze the reversible asymmetric aldol addition reaction of two aldehydes. In one aspect, an aldolase of the invention can accept a 3-azidopropinaldehyde as a substrate in a sequential asymmetric aldol reaction to form a deoxy-azidoethyl pyranose, which is a precursor to the corresponding lactone and atorvastatin (LIPITOR™). In another aspect, 2-methyl-substituted aldehydes act as substrates for aldolases of the invention (see, e.g., DeSantis (2003) Bioorg. Med. Chem. 11:43-52). In one aspect, an aldolase of the invention can have a D-2-keto-3-deoxy-6-phosphogluconate (KDPG) aldolase activity, e.g., to catalyze a reversible aldol reaction using a D-configurated KDPG as substrate. In another aspect, an aldolase of the invention is capable of accepting both D- and L-glyceraldehyde in the non-phosphorylated form as substrates for a reversible aldol reaction (see, e.g., Fong (2000) Chem. Biol. 7:873-83). In one aspect, an aldolase of the invention can have a catalytic activity toward enantiomeric substrates such as N-acetyl-L-mannosamine and L-arabinose to produce, e.g., an L-sialic acid or an L-KDO, the mirror-image sugars of the corresponding naturally occurring D-sugars (see, e.g., Wada (2003) Bioorg. Med. Chem. 11:2091-2098). In one aspect, an aldolase of the invention can have a 4-hydroxy-2-oxoglutarate aldolase activity, a fructose-1,6-bisphosphate aldolase (FBP-aldolase) activity, a tagatose-1,6-bisphosphate (TBP) aldolase activity or a 1-rhamnulose-1-phosphate aldolase activity (see, e.g., Schoevaart (2000) Biotechnol. Bioeng. 70:349-352). In one aspect, a FBP-aldolase activity of the invention catalyses the reversible condensation of dihydroxyacetone phosphate (DHAP) and glyceraldehyde phosphate (G3P) to form fructose bisphosphate (FBP). In one aspect, an aldolase of the invention can have broad substrate specificity with respect to its reverse reaction, e.g., the condensation of an aldose with pyruvate to form a wide range of 2-keto-3-deoxy-onic acids, including 2-keto-3-deoxy-nonulosonic acid, 2-keto-3-deoxy-octulosonic acid, 2-keto-3-deoxy-heptulosonic acid, and/or 2-keto-3-deoxy-hexylosonic acid. In one aspect, aldolases of the invention can process 2-keto-3-deoxy-onic acids to high-carbon 2-deoxy aldoses. In one aspect, aldolases of the invention can catalyze stereo-selective synthesis of sugars and compositions of matter comprising, e.g., arabinohexylose, xyloheptulose, threohexylose, and xylohexylose. The methods and polypeptides of the invention can be used to produce substantially optically pure sugars using racemic substrates. C-alkyl and N-containing sugars can also be produced using methods and polypeptides of the invention. The methods and polypeptides of the invention can be used to make disubstituted dihydroxypyrrolidines or disubstituted-azafuranoses (azasugars derived from pyrrolidines), e.g., 2-methyl-5-hydroxymethyl- and 2,5-dimethyl-3,4-dihydroxypyrrolidines, and a 5-azido-5-deoxyhexylose-1-phosphate, e.g., in a protocol comprising mixing a 2-azido-substituted-propionaldehyde and dihydroxyacetone phosphate in the presence of a catalytic amount of an aldolase of the invention. In one aspect of the invention, mixtures of enantiomeric D,L-threo 2-amino-3-hydroxy-3-phenylpropionic acids can be stereoisomerically enriched by contacting the mixture with a polypeptide of the invention having a D-threonine aldolase activity. In one aspect, D- and L-threo 2-amino-3-hydroxy-3-(4-methylsulfonylphenyl) propionic acid are treated with a D-threonine aldolase of the invention to produce L-threo 2-amino-3-hydroxy-3-(4-methylsulfonylphenyl)propionic acid with a high ee.

The processes of the invention can involve relatively mild reaction conditions, high stereoselectivity and/or the minimal use of protective group chemistry. These reactions are reversible, as, in some aspects, can be the activity of an aldolase of the invention. In alternative aspects, the processes of the invention comprise conditions such that a forward or the reverse reaction is favored, e.g., conditions where synthesis becomes favored.

Protocols for screening for aldolase activity (e.g., to determine if a polypeptide has an aldolase activity, e.g., 2-deoxyribose-5-phosphate aldolase (DERA) activity, and is within the scope of the invention) are well known in the art, see, e.g., U.S. Pat. Nos. 6,441,277; 6,423,834; 6,368,839; 5,795,749; 5,585,261; 5,576,426; 5,358,859; 5,352,591; 5,346,828; 5,346,828.

Polypeptides and peptides of the invention can be isolated from natural sources, be synthetic, or be recombinantly generated polypeptides. Peptides and proteins can be recombinantly expressed in vitro or in vivo. The peptides and polypeptides of the invention can be made and isolated using any method known in the art. Polypeptide and peptides of the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3 13) and automated synthesis may be achieved, e.g., using the ABI 431A Peptide Synthesizer (Perkin Elmer) in accordance with the instructions provided by the manufacturer.

The peptides and polypeptides of the invention can also be glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked.

The peptides and polypeptides of the invention, as defined above, include all "mimetic" and "peptidomimetic" forms. The terms "mimetic" and "peptidomimetic" refer to a synthetic chemical compound which has substantially the same structural and/or functional characteristics of the polypeptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Thus, in one aspect, a mimetic composition is within the scope of the invention if it has an aldolase activity.

Polypeptide mimetic compositions of the invention can contain any combination of non-natural structural components. In alternative aspect, mimetic compositions of the invention include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the invention can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH2- for —C(=O)—NH—), aminomethylene (CH2-NH), ethylene, olefin (CH=CH), ether (CH2-O), thioether (CH2-S), tetrazole (CN4-), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY).

A polypeptide of the invention can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)- phenylalanine; D-p-fluoro-phenylalanine; D- or L-p-biphenylphenylalanine; K- or L-p-methoxy-biphenylphenylalanine; D- or L-2-indole(alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N═C═N—R') such as, e.g., 1-cyclohexyl-3(2-morpholinyl-(4-ethyl) carbodiimide or 1-ethyl-3(4-azonia-4,4-dimetholpentyl) carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, preferably under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A residue, e.g., an amino acid, of a polypeptide of the invention can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R- or S-form.

The invention also provides methods for modifying the polypeptides of the invention by either natural processes, such as post-translational processing (e.g., phosphorylation, acylation, etc), or by chemical modification techniques, and the resulting modified polypeptides. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins—Structure and Molecular Properties 2nd Ed., W.H. Freeman and Company, New York (1993); Posttranslational Covalent Modification of Proteins, B. C. Johnson, Ed., Academic Press, New York, pp. 1-12 (1983).

Solid-phase chemical peptide synthesis methods can also be used to synthesize the polypeptide or fragments of the invention. Such method have been known in the art since the early 1960's (Merrifield, R. B., J. Am. Chem. Soc., 85:2149-2154, 1963) (See also Stewart, J. M. and Young, J. D., Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A™ automated peptide synthesizer. Such equipment provides ready access to the peptides of the invention, either by direct synthesis or by synthesis of a series of fragments that can be coupled using other known techniques.

Aldolase Enzymes

The invention provides novel aldolases, nucleic acids encoding them, antibodies that bind them, peptides representing the enzyme's antigenic sites (epitopes) and active sites, and methods for making and using them. In one aspect, polypeptides of the invention have an aldolase activity, as described above (e.g., catalysis of the formation of a carbon-carbon bond). In alternative aspects, the aldolases of the invention have activities that have been modified from those of the exemplary aldolases described herein. The invention includes aldolases with and without signal sequences and the signal sequences themselves. The invention includes immobilized aldolases, anti-aldolase antibodies and fragments thereof. The invention includes heterocomplexes, e.g., fusion proteins, heterodimers, etc., comprising the aldolases of the invention.

Determining peptides representing the enzyme's antigenic sites (epitopes), active sites, binding sites, signal sequences, and the like can be done by routine screening protocols.

The enzymes of the invention are highly selective catalysts. As with other enzymes, they catalyze reactions with exquisite stereo-, regio-, and chemo-selectivities that are unparalleled in conventional synthetic chemistry. Moreover, the enzymes of the invention are remarkably versatile. They can be tailored to function in organic solvents, operate at extreme pHs (for example, high pHs and low pHs) extreme temperatures (for example, high temperatures and low temperatures), extreme salinity levels (for example, high salinity and low salinity), and catalyze reactions with compounds that are structurally unrelated to their natural, physiological substrates. Enzymes of the invention can be designed to be reactive toward a wide range of natural and unnatural substrates, thus enabling the modification of virtually any organic lead compound. Enzymes of the invention can also be designed to be highly enantio- and regio-selective. The high degree of functional group specificity exhibited by these enzymes enables one to keep track of each reaction in a synthetic sequence leading to a new active compound. Enzymes of the invention can also be designed to catalyze many diverse reactions unrelated to their native physiological function in nature.

The present invention exploits the unique catalytic properties of enzymes. Whereas the use of biocatalysts (i.e., purified or crude enzymes, non-living or living cells) in chemical transformations normally requires the identification of a particular biocatalyst that reacts with a specific starting compound. The present invention uses selected biocatalysts, i.e., the enzymes of the invention, and reaction conditions that are specific for functional groups that are present in many starting compounds. Each biocatalyst is specific for one functional group, or several related functional groups, and can react with many starting compounds containing this functional group. The biocatalytic reactions produce a population of derivatives from a single starting compound. These derivatives can be subjected to another round of biocatalytic reactions to produce a second population of derivative compounds. Thousands of variations of the original compound can be produced with each iteration of biocatalytic derivatization.

Enzymes react at specific sites of a starting compound without affecting the rest of the molecule, a process that is very difficult to achieve using traditional chemical methods. This high degree of biocatalytic specificity provides the means to identify a single active enzyme within a library. The library is characterized by the series of biocatalytic reactions used to produce it, a so-called "biosynthetic history". Screening the library for biological activities and tracing the biosynthetic history identifies the specific reaction sequence producing the active compound. The reaction sequence is repeated and the structure of the synthesized compound determined. This mode of identification, unlike other synthesis and screening approaches, does not require immobilization technologies, and compounds can be synthesized and tested free in solution using virtually any type of screening assay. It is important to note, that the high degree of specificity of enzyme reactions on functional groups allows for the "tracking" of specific enzymatic reactions that make up the biocatalytically produced library.

The invention also provides methods of discovering new aldolases using the nucleic acids, polypeptides and antibodies of the invention. In one aspect, lambda phage libraries are screened for expression-based discovery of aldolases. Use of lambda phage libraries in screening allows detection of toxic clones; improved access to substrate; reduced need for engineering a host, by-passing the potential for any bias resulting from mass excision of the library; and, faster growth at low clone densities. Screening of lambda phage libraries can be in liquid phase or in solid phase. Screening in liquid phase gives greater flexibility in assay conditions; additional substrate flexibility; higher sensitivity for weak clones; and ease of automation over solid phase screening.

Many of the procedural steps are performed using robotic automation enabling the execution of many thousands of biocatalytic reactions and screening assays per day as well as ensuring a high level of accuracy and reproducibility (see discussion of arrays, below). As a result, a library of derivative compounds can be produced in a matter of weeks. For further teachings on modification of molecules, including small molecules, see PCT/US94/09174.

Aldolase Signal Sequences, Prepro Sequences and Catalytic Domains

The invention provides aldolase signal sequences (e.g., signal peptides (SPs)), prepro sequences and catalytic domains (CDs). The invention provides nucleic acids encoding these catalytic domains (CDs), prepro sequences and signal sequences (SPs, e.g., a peptide having a sequence comprising/consisting of amino terminal residues of a polypeptide of the invention). In one aspect, the invention provides a signal sequence comprising a peptide comprising/consisting of a sequence as set forth in residues 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 28, 1 to 30, 1 to 31, 1 to 32, 1 to 33, 1 to 34, 1 to 35, 1 to 36, 1 to 37, 1 to 38, 1 to 39, 1 to 40, 1 to 41, 1 to 42 or 1 to 43 or more, of a polypeptide of the invention, e.g., SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30, or enzymatically active fragments thereof. For example, an exemplary aldolase signal sequence of the invention is residues 1 to 22 of SEQ ID NO:18.

The aldolase signal sequences of the invention can be isolated peptides, or, sequences joined to another aldolase or a non-aldolase polypeptide, e.g., as a fusion protein. In one aspect, the invention provides polypeptides comprising aldolase signal sequences of the invention. In one aspect, polypeptides comprising aldolase signal sequences of the invention comprise sequences heterologous to an aldolase of the invention (e.g., a fusion protein comprising an aldolase signal sequence of the invention and sequences from another aldolase or a non-aldolase protein). In one aspect, the invention provides aldolases of the invention with heterologous signal sequences, e.g., sequences with a yeast signal sequence. An aldolase of the invention can comprise a heterologous signal sequence, e.g., in a vector, e.g., a pPIC series vector (Invitrogen, Carlsbad, Calif.).

In one aspect, the signal sequences of the invention are identified following identification of novel aldolase polypeptides. The pathways by which proteins are sorted and transported to their proper cellular location are often referred to as protein targeting pathways. One of the most important elements in all of these targeting systems is a short amino acid sequence at the amino terminus of a newly synthesized polypeptide called the signal sequence. This signal sequence directs a protein to its appropriate location in the cell and is removed during transport or when the protein reaches its final destination. Most lysosomal, membrane, or secreted proteins have an amino-terminal signal sequence that marks them for translocation into the lumen of the endoplasmic reticulum. More than 100 signal sequences for proteins in this group have been determined. The signal sequences can vary in length from 13 to 36 amino acid residues. Various methods of recognition of signal sequences are known to those of skill in the art. For example, in one aspect, novel aldolase signal peptides are identified by a method referred to as SignalP. SignalP uses a combined neural network which recognizes both signal peptides and their cleavage sites. (Nielsen, et al., "Identification of prokaryotic and eukaryotic signal peptides and prediction of their cleavage sites." Protein Engineering, vol. 10, no. 1, p. 1-6 (1997).

It should be understood that in some aspects aldolases of the invention may not have signal sequences. In one aspect, the invention provides the aldolases of the invention lacking all or part of a signal sequence. In one aspect, the invention provides a nucleic acid sequence encoding a signal sequence from one aldolase operably linked to a nucleic acid sequence of a different aldolase or, optionally, a signal sequence from a non-aldolase protein may be desired.

The invention also provides isolated or recombinant polypeptides comprising signal sequences (SPs), prepro sequences (PPS) and/or catalytic domains (CDs) of the invention and heterologous sequences. The heterologous sequences are sequences not naturally associated (e.g., to an aldolase) with an SP, PPS and/or CD. The sequence to which the SP, PPS and/or CD are not naturally associated can be on the SP's, PPS's and/or CD's amino terminal end, carboxy terminal end, and/or on both ends of the SP, PPS and/or CD. In one aspect, the invention provides an isolated or recombinant polypeptide comprising (or consisting of) a polypeptide comprising an SP, PPS and/or CD of the invention with the proviso that it is not associated with any sequence to which it is naturally associated (e.g., an aldolase sequence). Similarly in one aspect, the invention provides isolated or recombinant nucleic acids encoding these polypeptides. Thus, in one aspect, the isolated or recombinant nucleic acid of the invention comprises coding sequence for an SP, PPS and/or CD of the invention and a heterologous sequence (i.e., a sequence not naturally associated with the SP, PPS and/or CD of the invention). The heterologous sequence can be on the 3' terminal end, 5' terminal end, and/or on both ends of the SP, PPS and/or CD coding sequence.

Hybrid (Chimeric) Aldolases and Peptide Libraries

In one aspect, the invention provides hybrid aldolases and fusion proteins, including peptide libraries, comprising sequences of the invention. The peptide libraries of the invention can be used to isolate peptide modulators (e.g., activators or inhibitors) of targets, such as aldolase substrates, receptors, enzymes. The peptide libraries of the invention can be used to identify formal binding partners of targets, such as ligands, e.g., cytokines, hormones and the like. In one aspect, the invention provides chimeric proteins comprising a signal sequence (SP), a prepro sequence (PPS) and/or catalytic domain (CD) of the invention and a heterologous sequence (see above).

The invention provides fusion proteins and nucleic acids encoding them. A polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441-53.

The invention also provides methods for generating "improved" and hybrid aldolases using the nucleic acids and polypeptides of the invention. For example, the invention provides methods for generating enzymes that have activity, e.g., aldolase activity (such as, e.g., catalysis of the formation of a carbon-carbon bond, a 2-deoxyribose-5-phosphate aldolase (DERA) activity) at extreme alkaline pHs and/or acidic pHs, high and low temperatures, osmotic conditions and the like. The invention provides methods for generating hybrid enzymes (e.g., hybrid aldolases).

In one aspect, the methods of the invention produce new hybrid polypeptides by utilizing cellular processes that integrate the sequence of a first polynucleotide such that resulting hybrid polynucleotides encode polypeptides demonstrating activities derived from the first biologically active polypeptides. For example, the first polynucleotides can be an exemplary nucleic acid sequence (e.g., SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, etc.) encoding an exemplary aldolase of the invention (e.g., SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30, or enzymatically active fragments thereof, etc.). The first nucleic acid can encode an enzyme from one organism that functions effectively under a particular environmental condition, e.g. high salinity. It can be "integrated" with an enzyme encoded by a second polynucleotide from a different organism that functions effectively under a different environmental condition, such as extremely high temperatures. For example, when the two nucleic acids can produce a hybrid molecule by e.g., recombination and/or reductive reassortment. A hybrid polynucleotide containing sequences from the first and second original polynucleotides may encode an enzyme that exhibits characteristics of both enzymes encoded by the original polynucleotides. Thus, the enzyme encoded by the hybrid polynucleotide may function effectively under environmental conditions shared by each of the enzymes encoded by the first and second polynucleotides, e.g., high salinity and extreme temperatures.

Alternatively, a hybrid polypeptide resulting from this method of the invention may exhibit specialized enzyme activity not displayed in the original enzymes. For example, following recombination and/or reductive reassortment of polynucleotides encoding aldolase activities, the resulting hybrid polypeptide encoded by a hybrid polynucleotide can be screened for specialized activities obtained from each of the original enzymes. Thus, for example, the aldolase may be screened to ascertain those chemical functionalities which distinguish the hybrid aldolase from the original aldolases, for example, the temperature, pH or salt concentration at which the hybrid polypeptide functions.

Sources of the polynucleotides to be "integrated" with nucleic acids of the invention may be isolated from individual organisms ("isolates"), collections of organisms that have been grown in defined media ("enrichment cultures"), or, uncultivated organisms ("environmental samples"). The use of a culture-independent approach to derive polynucleotides encoding novel bioactivities from environmental samples is most preferable since it allows one to access untapped resources of biodiversity. "Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample that may be under-represented by several orders of magnitude compared to the dominant species.

For example, gene libraries generated from one or more uncultivated microorganisms are screened for an activity of interest (e.g., a 2-deoxyribose-5-phosphate aldolase (DERA) activity). Potential pathways encoding bioactive molecules of interest are first captured in prokaryotic cells in the form of gene expression libraries. Polynucleotides encoding activities of interest are isolated from such libraries and introduced into a host cell. The host cell is grown under conditions that promote recombination and/or reductive reassortment creating potentially active biomolecules with novel or enhanced activities.

The microorganisms from which hybrid polynucleotides may be prepared include prokaryotic microorganisms, such as Eubacteria and Archaebacteria, and lower eukaryotic microorganisms such as fungi, some algae and protozoa. Polynucleotides may be isolated from environmental samples. Nucleic acid may be recovered without culturing of an organism or recovered from one or more cultured organisms. In one aspect, such microorganisms may be extremophiles, such as hyperthermophiles, psychrophiles, psychrotrophs, halophiles, barophiles and acidophiles. In one aspect, polynucleotides encoding aldolase enzymes isolated from extremophilic microorganisms are used to make hybrid enzymes. Such enzymes may function at temperatures above 100° C. in, e.g., terrestrial hot springs and deep sea thermal vents, at temperatures below 0° C. in, e.g., arctic waters, in the saturated salt environment of, e.g., the Dead Sea, at pH values around 0 in, e.g., coal deposits and geothermal sulfur-rich springs, or at pH values greater than 11 in, e.g., sewage sludge. For example, aldolases cloned and expressed from extremophilic organisms can show high activity throughout a wide range of temperatures and pHs.

Polynucleotides selected and isolated as described herein, including at least one nucleic acid of the invention, are introduced into a suitable host cell. A suitable host cell is any cell that is capable of promoting recombination and/or reductive reassortment. The selected polynucleotides can be in a vector that includes appropriate control sequences. The host cell can be a higher eukaryotic cell, such as a mammalian cell, or a lower eukaryotic cell, such as a yeast cell, or preferably, the host cell can be a prokaryotic cell, such as a bacterial cell. Introduction of the construct into the host cell can be effected by calcium phosphate transfection, DEAE-Dextran mediated transfection, or electroporation.

Exemplary hosts include, e.g., bacterial cells, such as *E. coli, Streptomyces, Salmonella typhimurium*; fungal cells, such as yeast; insect cells such as *Drosophila* S2 and *Spodoptera* Sf9; animal cells such as CHO, COS or Bowes melanoma; adenoviruses; and plant cells. The selection of an appropriate host for recombination and/or reductive reassortment or just for expression of recombinant protein is deemed to be within the scope of those skilled in the art from the teachings herein. Mammalian cell culture systems that can be employed for recombination and/or reductive reassortment or just for expression of recombinant protein include, e.g., the COS-7 lines of monkey kidney fibroblasts, described in "SV40-transformed simian cells support the replication of early SV40 mutants", the C127, 3T3, CHO, HeLa and BHK cell lines. Mammalian expression vectors can comprise an origin of replication, a suitable promoter and enhancer, and necessary ribosome binding sites, polyadenylation site, splice donor and acceptor sites, transcriptional termination sequences, and 5' flanking non-transcribed sequences. DNA sequences derived from the SV40 splice, and polyadenylation sites may be used to provide the required non-transcribed genetic elements.

Host cells containing the polynucleotides of interest (for recombination and/or reductive reassortment or just for expression of recombinant protein) can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan. The clones which are identified as having the specified enzyme activity may then be sequenced to identify the polynucleotide sequence encoding an enzyme having the enhanced activity.

In another aspect, the nucleic acids and methods of the present invention can be used to generate novel polynucleotides for biochemical pathways, e.g., pathways from one or more operons or gene clusters or portions thereof. For example, bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. Thus, a gene cluster is a group of adjacent genes that are either identical or related, usually as to their function.

Gene cluster DNA can be isolated from different organisms and ligated into vectors, particularly vectors containing expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of *E. coli*. This f-factor of *E. coli* is a plasmid which affects high-frequency transfer of itself during conjugation and is ideal to achieve and stably propagate large DNA fragments, such as gene clusters from mixed microbial samples. "Fosmids," cosmids or bacterial artificial chromosome (BAC) vectors can be used as cloning vectors. These are derived from *E. coli* f-factor which is able to stably integrate large segments of genomic DNA. When integrated with DNA from a mixed uncultured environmental sample, this makes it possible to achieve large genomic fragments in the form of a stable "environmental DNA library." Cosmid vectors were originally designed to clone and propagate large segments of genomic DNA. Cloning into cosmid vectors is described in detail in Sambrook et al., Molecular Cloning: A Laboratory Manual, 2nd Ed., Cold Spring Harbor Laboratory Press (1989). Once ligated into an appropriate vector, two or more vectors containing different polyketide synthase gene clusters can be introduced into a suitable host cell. Regions of partial sequence homology shared by the gene clusters will promote processes which result in sequence reorganization resulting in a hybrid gene cluster. The novel hybrid gene cluster can then be screened for enhanced activities not found in the original gene clusters.

Thus, in one aspect, the invention relates to a method for producing a biologically active hybrid polypeptide using a nucleic acid of the invention and screening the polypeptide for an activity (e.g., enhanced activity) by:

(1) introducing at least a first polynucleotide (e.g., a nucleic acid of the invention) in operable linkage and a second polynucleotide in operable linkage, said at least first polynucleotide and second polynucleotide sharing at least one region of partial sequence homology, into a suitable host cell;

(2) growing the host cell under conditions which promote sequence reorganization resulting in a hybrid polynucleotide in operable linkage;

(3) expressing a hybrid polypeptide encoded by the hybrid polynucleotide;

(4) screening the hybrid polypeptide under conditions which promote identification of the desired biological activity (e.g., enhanced aldolase activity); and (5) isolating the a polynucleotide encoding the hybrid polypeptide.

Methods for screening for various enzyme activities are known to those of skill in the art and are discussed throughout the present specification. Such methods may be employed when isolating the polypeptides and polynucleotides of the invention.

In vivo reassortment can be focused on "inter-molecular" processes collectively referred to as "recombination." In bacteria it is generally viewed as a "RecA-dependent" phenomenon. The invention can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process. Thus, in one aspect of the invention, using the nucleic acids of the invention novel polynucleotides are generated by the process of reductive reassortment. The method involves the generation of constructs containing consecutive sequences (original encoding sequences), their insertion into an appropriate vector, and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences, and results in the production of novel molecular species.

Various treatments may be applied to enhance the rate of reassortment. These could include treatment with ultra-violet light, or DNA damaging chemicals, and/or the use of host cell lines displaying enhanced levels of "genetic instability". Thus the reassortment process may involve homologous recombination or the natural property of quasi-repeated sequences to direct their own evolution.

Repeated or "quasi-repeated" sequences play a role in genetic instability. "Quasi-repeats" are repeats that are not restricted to their original unit structure. Quasi-repeated units can be presented as an array of sequences in a construct; consecutive units of similar sequences. Once ligated, the junctions between the consecutive sequences become essentially invisible and the quasi-repetitive nature of the resulting construct is now continuous at the molecular level. The deletion process the cell performs to reduce the complexity of the resulting construct operates between the quasi-repeated sequences. The quasi-repeated units provide a practically limitless repertoire of templates upon which slippage events can occur. The constructs containing the quasi-repeats thus effectively provide sufficient molecular elasticity that deletion (and potentially insertion) events can occur virtually anywhere within the quasi-repetitive units. When the quasi-repeated sequences are all ligated in the same orientation, for instance head to tail or vice versa, the cell cannot distinguish individual units. Consequently, the reductive process can occur throughout the sequences. In contrast, when for example, the units are presented head to head, rather than head to tail, the inversion delineates the endpoints of the adjacent unit so that deletion formation will favor the loss of discrete units. Thus, in one aspect of the invention, the sequences to be reasserted are in the same orientation. Random orientation of quasi-repeated sequences will result in the loss of reassortment efficiency, while consistent orientation of the sequences will offer the highest efficiency. However, while having fewer of the contiguous sequences in the same orientation decreases the efficiency, it may still provide sufficient elasticity for the effective recovery of novel molecules. Constructs can be made with the quasi-repeated sequences in the same orientation to allow higher efficiency.

Sequences can be assembled in a head to tail orientation using any of a variety of methods, including the following: a) Primers that include a poly-A head and poly-T tail which when made single-stranded would provide orientation can be utilized. This is accomplished by having the first few bases of the primers made from RNA and hence easily removed RNase H. b) Primers that include unique restriction cleavage sites can be utilized. Multiple sites, a battery of unique sequences, and repeated synthesis and ligation steps would be required. c) The inner few bases of the primer could be thiolated and an exonuclease used to produce properly tailed molecules.

The recovery of the re-assorted sequences relies on the identification of cloning vectors with a reduced repetitive index (RI). The re-assorted encoding sequences can then be recovered by amplification. The products are re-cloned and expressed. The recovery of cloning vectors with reduced RI can be affected by: 1) The use of vectors only stably maintained when the construct is reduced in complexity. 2) The physical recovery of shortened vectors by physical procedures. In this case, the cloning vector would be recovered using standard plasmid isolation procedures and size fractionated on either an agarose gel, or column with a low molecular weight cut off utilizing standard procedures. 3) The recovery of vectors containing interrupted genes which can be selected when insert size decreases. 4) The use of direct selection techniques with an expression vector and the appropriate selection.

Encoding sequences (for example, genes) from related organisms may demonstrate a high degree of homology and encode quite diverse protein products. These types of sequences are particularly useful in the present invention as quasi-repeats. However, this process is not limited to such nearly identical repeats.

The following is an exemplary method of the invention. Encoding nucleic acid sequences (quasi-repeats) are derived from three (3) species, including a nucleic acid of the invention. Each sequence encodes a protein with a distinct set of properties, including an enzyme of the invention. Each of the sequences differs by a single or a few base pairs at a unique position in the sequence. The quasi-repeated sequences are separately or collectively amplified and ligated into random assemblies such that all possible permutations and combinations are available in the population of ligated molecules. The number of quasi-repeat units can be controlled by the assembly conditions. The average number of quasi-repeated units in a construct is defined as the repetitive index (RI). Once formed, the constructs may, or may not be size fractionated on an agarose gel according to published protocols, inserted into a cloning vector, and transfected into an appropriate host cell. The cells are then propagated and "reductive reassortment" is effected. The rate of the reductive reassortment process may be stimulated by the introduction of DNA damage if desired. Whether the reduction in RI is mediated by deletion formation between repeated sequences by an "intra-molecular" mechanism, or mediated by recombination-like events through "inter-molecular" mechanisms is immaterial. The end result is a reassortment of the molecules into all possible combinations. In one aspect, the method comprises the additional step of screening the library members of the shuffled pool to identify individual shuffled library members having the ability to bind or otherwise interact, or catalyze a particular reaction (e.g., such as catalytic domain of an enzyme) with a predetermined macromolecule, such as for example a proteinaceous receptor, an oligosaccharide, virion, or other predetermined compound or structure. The polypeptides, e.g., aldolases, that are identified from such libraries can be used for various purposes, e.g., the industrial processes described herein and/or can be subjected to one or more additional cycles of shuffling and/or selection.

In another aspect, it is envisioned that prior to or during recombination or reassortment, polynucleotides generated by the method of the invention can be subjected to agents or processes which promote the introduction of mutations into the original polynucleotides. The introduction of such mutations would increase the diversity of resulting hybrid polynucleotides and polypeptides encoded therefrom. The agents or processes which promote mutagenesis can include, but are not limited to: (+)-CC-1065, or a synthetic analog such as (+)-CC-1065-(N-3-Adenine (See Sun and Hurley, (1992); an N-acetylated or deacetylated 4'-fluoro-4-aminobiphenyl adduct capable of inhibiting DNA synthesis (See, for example, van de Poll et al. (1992)); or a N-acetylated or deacetylated 4-aminobiphenyl adduct capable of inhibiting DNA synthesis (See also, van de Poll et al. (1992), pp. 751-758); trivalent chromium, a trivalent chromium salt, a polycyclic aromatic hydrocarbon (PAH) DNA adduct capable of inhibiting DNA replication, such as 7-bromomethyl-benz[a]anthracene ("BMA"), tris(2,3-dibromopropyl)phosphate ("Tris-BP"), 1,2-dibromo-3-chloropropane ("DBCP"), 2-bromoacrolein (2BA), benzo[a]pyrene-7,8-dihydrodiol-9-10-epoxide ("BPDE"), a platinum(II) halogen salt, N-hydroxy-2-amino-3-methylimidazo[4,5-f]-quinoline ("N-hydroxy-IQ"), and N-hydroxy-2-amino-1-methyl-6-phenyl]midazo[4,5-f]-pyridine ("N-hydroxy-PhIP"). Especially preferred means for slowing or halting PCR amplification consist of UV light (+)-CC-1065 and (+)-CC-1065-(N-3-Adenine). Particularly encompassed means are DNA adducts or polynucleotides comprising the DNA adducts from the polynucleotides or polynucleotides pool, which can be released or removed by a process including heating the solution comprising the polynucleotides prior to further processing.

Screening Methodologies and "On-Line" Monitoring Devices

In practicing the methods of the invention, and screening for aldolase activity in the polypeptides of the invention, a variety of apparatus and methodologies can be used. For example, a variety of apparatus and methodologies can be used to screen polypeptides for aldolase activity, to screen compounds as potential modulators of activity (e.g., potentiation or inhibition of aldolase activity), for antibodies that bind to an aldolase of the invention or have aldolase activity, for nucleic acids that hybridize to a nucleic acid of the invention, and the like. High throughput screening apparatus can be adapted and used to practice the methods of the invention, see, e.g., U.S. Patent Application No. 20020001809.

Immobilized Enzyme Solid Supports

The polypeptides of the invention, e.g., antibodies and aldolase enzymes, fragments thereof and nucleic acids that encode the polypeptides of the invention (e.g., aldolases) and fragments can be affixed to a solid support. This is often economical and efficient in the use of the aldolases in industrial processes. For example, a consortium or cocktail of aldolase enzymes (or active fragments thereof), which are used in a specific chemical reaction, can be attached to a solid support and dunked into a process vat. The enzymatic reaction can occur. Then, the solid support can be taken out of the vat, along with the enzymes affixed thereto, for repeated use. In one embodiment of the invention, an isolated nucleic acid of the invention is affixed to a solid support. In another embodiment of the invention, the solid support is selected from the group of a gel, a resin, a polymer, a ceramic, a glass, a microelectrode and any combination thereof.

For example, solid supports useful in this invention include gels. Some examples of gels include Sepharose, gelatin, glutaraldehyde, chitosan-treated glutaraldehyde, albumin-glutaraldehyde, chitosan-Xanthan, toyopearl gel (polymer gel), alginate, alginate-polylysine, carrageenan, agarose, glyoxyl agarose, magnetic agarose, dextran-agarose, poly(Carbamoyl Sulfonate) hydrogel, BSA-PEG hydrogel, phosphorylated polyvinyl alcohol (PVA), monoaminoethyl-N-aminoethyl (MANA), amino, or any combination thereof.

Another solid support useful in the present invention are resins or polymers. Some examples of resins or polymers include cellulose, acrylamide, nylon, rayon, polyester, anion-exchange resin, AMBERLITE™ XAD-7, AMBERLITE™ XAD-8, AMBERLITE™ IRA-94, AMBERLITE™ IRC-50, polyvinyl, polyacrylic, polymethacrylate, or any combination thereof.

Another type of solid support useful in the present invention is ceramic. Some examples include non-porous ceramic, porous ceramic, $SiO_2$, $Al_2O_3$. Another type of solid support useful in the present invention is glass. Some examples include non-porous glass, porous glass, aminopropyl glass or any combination thereof. Another type of solid support that can be used is a microelectrode. An example is a polyethyleneimine-coated magnetite. Graphitic particles can be used as a solid support. Another example of a solid support is a cell, such as a red blood cell.

Methods of Immobilization

There are many methods that would be known to one of skill in the art for immobilizing antibodies, enzymes or fragments thereof, or nucleic acids, onto a solid support. Some examples of such methods include, e.g., electrostatic droplet generation, electrochemical means, via adsorption, via covalent binding, via cross-linking, via a chemical reaction or process, via encapsulation, via entrapment, via calcium alginate, or via poly (2-hydroxyethyl methacrylate). Like methods are described in Methods in Enzymology, Immobilized Enzymes and Cells, Part C. 1987. Academic Press. Edited by S. P. Colowick and N, O. Kaplan. Volume 136; and Immobilization of Enzymes and Cells. 1997. Humana Press. Ed. G. F. Bickerstaff. Series: Methods in Biotechnology, Ed. J. M. Walker.

Capillary Arrays

Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. Capillary arrays, such as the GIGAMATRIX™, Diversa Corporation, San Diego, Calif.; and arrays described in, e.g., U.S. Patent Application No. 20020080350 A1; WO 0231203 A; WO 0244336 A, provide an alternative apparatus for holding and screening samples. In one aspect, the capillary array includes a plurality of capillaries formed into an array of adjacent capillaries, wherein each capillary comprises at least one wall defining a lumen for retaining a sample. The lumen may be cylindrical, square, hexagonal or any other geometric shape so long as the walls form a lumen for retention of a liquid or sample. The capillaries of the capillary array can be held together in close proximity to form a planar structure. The capillaries can be bound together, by being fused (e.g., where the capillaries are made of glass), glued, bonded, or clamped side-by-side. Additionally, the capillary array can include interstitial material disposed between adjacent capillaries in the array, thereby forming a solid planar device containing a plurality of through-holes.

A capillary array can be formed of any number of individual capillaries, for example, a range from 100 to 4,000,000 capillaries. Further, a capillary array having about 100,000 or more individual capillaries can be formed into the standard size and shape of a Microtiter® plate for fitment into standard laboratory equipment. The lumens are filled manually or automatically using either capillary action or microinjection using a thin needle. Samples of interest may subsequently be removed from individual capillaries for further analysis or characterization. For example, a thin, needle-like probe is positioned in fluid communication with a selected capillary to either add or withdraw material from the lumen.

In a single-pot screening assay, the assay components are mixed yielding a solution of interest, prior to insertion into the capillary array. The lumen is filled by capillary action when at least a portion of the array is immersed into a solution of interest. Chemical or biological reactions and/or activity in each capillary are monitored for detectable events. A detectable event is often referred to as a "hit", which can usually be distinguished from "non-hit" producing capillaries by optical detection. Thus, capillary arrays allow for massively parallel detection of "hits".

In a multi-pot screening assay, a polypeptide or nucleic acid, e.g., a ligand, can be introduced into a first component, which is introduced into at least a portion of a capillary of a capillary array. An air bubble can then be introduced into the capillary behind the first component. A second component can then be introduced into the capillary, wherein the second component is separated from the first component by the air bubble. The first and second components can then be mixed by applying hydrostatic pressure to both sides of the capillary array to collapse the bubble. The capillary array is then monitored for a detectable event resulting from reaction or non-reaction of the two components.

In a binding screening assay, a sample of interest can be introduced as a first liquid labeled with a detectable particle into a capillary of a capillary array, wherein the lumen of the capillary is coated with a binding material for binding the detectable particle to the lumen. The first liquid may then be removed from the capillary tube, wherein the bound detectable particle is maintained within the capillary, and a second liquid may be introduced into the capillary tube. The capillary is then monitored for a detectable event resulting from reaction or non-reaction of the particle with the second liquid.

Arrays, or "BioChips"

Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. For example, in one aspect of the invention, a monitored parameter is transcript expression of an aldolase gene. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. "Polypeptide arrays" can also be used to simultaneously quantify a plurality of proteins.

The present invention can be practiced with any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts.

In practicing the methods of the invention, any known array and/or method of making and using arrays can be incorporated in whole or in part, or variations thereof, as described, for example, in U.S. Pat. Nos. 6,277,628; 6,277,489; 6,261, 776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent applications Nos. 20010018642; 20010019827; 20010016322; 20010014449; 20010014448; 20010012537; 20010008765.

Antibodies and Antibody-Based Screening Methods

The invention provides isolated or recombinant antibodies that specifically bind to polypeptides of the invention, e.g., an aldolase of the invention or other antibodies of the invention (e.g., an anti-idiotype antibody). These antibodies can be used to isolate, identify or quantify the aldolases of the invention or related polypeptides. These antibodies can be used to inhibit the activity of an enzyme of the invention. These antibodies can be used to isolated polypeptides related to those of the invention, e.g., related aldolase enzymes.

The antibodies can be used in immunoprecipitation, staining (e.g., FACS), immunoaffinity columns, and the like. If desired, nucleic acid sequences encoding for specific antigens can be generated by immunization followed by isolation of polypeptide or nucleic acid, amplification or cloning and immobilization of polypeptide onto an array of the invention.

Alternatively, the methods of the invention can be used to modify the structure of an antibody produced by a cell to be modified, e.g., an antibody's affinity can be increased or decreased. Furthermore, the ability to make or modify antibodies can be a phenotype engineered into a cell by the methods of the invention.

The antibodies of the invention can be used to detect or measure the amount of an aldolase in a sample, e.g., a serum aldolase. Normal serum aldolase levels are <6 U/L. High levels of aldolase are found in progressive Duchenne muscular dystrophy (MD), in carriers of MD, in limb-girdle dystrophy and other dystrophies, in dermatomyositis, polymyositis, and trichinosis. In the progressive dystrophies, aldolase levels may be 10-15 times normal when muscle mass is relatively intact, as in early stages of the disease. When advanced muscle wasting is present, values decline. Thus, the antibodies of the invention can be used in the treatment, diagnosis or prognosis of conditions or diseases.

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu. Rev. Biophys. Biomol. Struct. 26:27-45.

The polypeptides can be used to generate antibodies which bind specifically to the polypeptides of the invention. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the invention.

In immunoaffinity procedures, the antibody is attached to a solid support, such as a bead or other column matrix. The protein preparation is placed in contact with the antibody under conditions in which the antibody specifically binds to one of the polypeptides of the invention. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of the invention can be obtained by direct injection of the polypeptides into an animal or by administering the polypeptides to an animal, for example, a nonhuman. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique, the trioma technique, the human B-cell hybridoma technique, and the EBV-hybridoma technique (see, e.g., Cole (1985) in Monoclonal Antibodies and Cancer Therapy, Alan R. Liss, Inc., pp. 77-96).

Techniques described for the production of single chain antibodies (see, e.g., U.S. Pat. No. 4,946,778) can be adapted to produce single chain antibodies to the polypeptides of the invention. Alternatively, transgenic mice may be used to express humanized antibodies to these polypeptides or fragments thereof.

Antibodies generated against the polypeptides of the invention may be used in screening for similar polypeptides from other organisms and samples. In such techniques, polypeptides from the organism are contacted with the antibody and those polypeptides which specifically bind the antibody are detected. Any of the procedures described above may be used to detect antibody binding.

Kits

The invention provides kits comprising the compositions, e.g., nucleic acids, expression cassettes, vectors, cells, polypeptides (e.g., aldolases) and/or antibodies of the invention. The kits also can contain instructional material teaching the methodologies and industrial uses of the invention, as described herein.

Preparation of β,δ-Dihydroxyheptanoic Acid Side Chains

The invention provides compositions and methods for using a 2-deoxyribose-5-phosphate aldolase (DERA) in a process to prepare a chiral β,δ-dihydroxyheptanoic acid side chain. Any DERA or equivalent aldolase, or enzyme or other polypeptide having a similar activity, natural or synthetic (e.g., catalytic antibodies, see, e.g., U.S. Pat. Nos. 6,368,839; 5,733,757), including an enzyme of the invention, can be used. The chemoenzymatic methods of the invention can use any polypeptide having an aldolase activity (e.g., an enzyme, a catalytic antibody), e.g., SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, including a polypeptide of the invention having an aldolase activity, e.g., the exemplary SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22. Also see, e.g., U.S. Pat. No. 5,795,749, describing how to make, isolate and test for DERA activity; U.S. Pat. Nos. 6,423,834; 6,441,277.

For example, DERA activity can be assayed with a coupled enzymatic system where 0.5 mM of 2-deoxyribose-5-phosphate, 0.12 mM NADH, and a mixture of glycerophosphate dehydrogenase and triose phosphate isomerase are incubated in triethanolamine buffer (50 mM, pH 7.5) at 25° C. The assay can be initiated by addition of DERA, and the decrease in the absorbance at 340 nm is monitored. The extinction coefficient for NADH is taken as $6.22 \times 10^3 M^{-1} cm^{-1}$. Protein concentration can be measured by a Bradford assay (e.g., a Coomassie Plus Kit Reagent from Pierce Co.).

The invention provides novel routes for the chemoenzymatic production of chiral β,δ-dihydroxyheptanoic acid side chains, including (R)-Ethyl-4-Cyano-3-Hydroxybutyrate, rosuvastatin (CRESTOR™), atorvastatin (LIPITOR™), fluvastatin (LESCOL™) and their intermediates. Various starting materials can be chosen; cost may be a factor. The method can be in a whole cell process or a biocatalytic process or a combination thereof. At least one step in this exemplary method involves use of an enzyme. In alternative aspects, one, several or all steps use an enzyme.

The enzymatic reactions of the invention can be done in vitro or in vivo, e.g., by whole cell methods. The enzymatic reactions can be done in vitro, including, e.g. capillary arrays, as discussed below, or, in whole cell systems, also discussed further below. In one aspect, enzyme reactions can be done in one or more reaction vessels. The enzymes or reagents of the invention can be immobilized onto solid surfaces, e.g., arrays or capillary surfaces.

Whole Cell Engineering and Measuring Metabolic Parameters

The methods of the invention can be practiced in whole or in part in a whole cell environment. The invention also provides for whole cell evolution, or whole cell engineering, of a cell to develop a new cell strain having a new phenotype to be used in the methods of the invention, e.g., a new cell line comprising one, several or all enzymes of the invention, or an enzyme used in a method of the invention. This can be done by modifying the genetic composition of the cell, where the genetic composition is modified by addition to the cell of a nucleic acid, e.g., a coding sequence for an enzyme used in the methods of the invention. See, e.g., WO0229032; WO0196551.

The host cell for the "whole-cell process" may be any cell known to one skilled in the art, including prokaryotic cells, eukaryotic cells, such as bacterial cells, fungal cells, yeast cells, mammalian cells, insect cells, or plant cells.

To detect the production of an intermediate or product of the methods of the invention (e.g., β,δ-dihydroxyheptanoic acid side chains and (R)-Ethyl-4-Cyano-3-Hydroxybutyrate), or a new phenotype, at least one metabolic parameter of a cell (or a genetically modified cell) can be monitored in the cell in a "real time" or "on-line" time frame by Metabolic Flux Analysis (MFA). In one aspect, a plurality of cells, such as a cell culture, is monitored in "real time" or "on-line." In one aspect, a plurality of metabolic parameters is monitored in "real time" or "on-line."

Metabolic flux analysis (MFA) is based on a known biochemistry framework. A linearly independent metabolic matrix is constructed based on the law of mass conservation and on the pseudo-steady state hypothesis (PSSH) on the intracellular metabolites. In practicing the methods of the invention, metabolic networks are established, including the:
identity of all pathway substrates, products and intermediary metabolites
identity of all the chemical reactions interconverting the pathway metabolites, the stoichiometry of the pathway reactions,
identity of all the enzymes catalyzing the reactions, the enzyme reaction kinetics,
the regulatory interactions between pathway components, e.g. allosteric interactions, enzyme-enzyme interactions etc,
intracellular compartmentalization of enzymes or any other supramolecular organization of the enzymes, and,
the presence of any concentration gradients of metabolites, enzymes or effector molecules or diffusion barriers to their movement.

Once the metabolic network for a given strain is built, mathematic presentation by matrix notion can be introduced to estimate the intracellular metabolic fluxes if the on-line metabolome data is available. Metabolic phenotype relies on the changes of the whole metabolic network within a cell. Metabolic phenotype relies on the change of pathway utilization with respect to environmental conditions, genetic regulation, developmental state and the genotype, etc. In one aspect of the methods of the invention, after the on-line MFA calculation, the dynamic behavior of the cells, their phenotype and other properties are analyzed by investigating the pathway utilization.

Control of physiological state of cell cultures will become possible after the pathway analysis. The methods of the invention can help determine how to manipulate the fermentation by determining how to change the substrate supply, temperature, use of inducers, etc. to control the physiological state of cells to move along desirable direction. In practicing the methods of the invention, the MFA results can also be compared with transcriptome and proteome data to design experiments and protocols for metabolic engineering or gene shuffling, etc. Any aspect of metabolism or growth can be monitored.

Monitoring Expression of an mRNA Transcript

In one aspect of the invention, the engineered phenotype comprises increasing or decreasing the expression of an mRNA transcript or generating new transcripts in a cell. This increased or decreased expression can be traced by use of a fluorescent polypeptide, e.g., a chimeric protein comprising an enzyme used in the methods of the invention. mRNA transcripts, or messages, also can be detected and quantified by any method known in the art, including, e.g., Northern blots, quantitative amplification reactions, hybridization to arrays, and the like. Quantitative amplification reactions include, e.g., quantitative PCR, including, e.g., quantitative reverse transcription polymerase chain reaction, or RT-PCR; quantitative real time RT-PCR, or "real-time kinetic RT-PCR" (see, e.g., Kreuzer (2001) Br. J. Haematol. 114: 313-318; Xia (2001) Transplantation 72:907-914).

In one aspect of the invention, the engineered phenotype is generated by knocking out expression of a homologous gene. The gene's coding sequence or one or more transcriptional control elements can be knocked out, e.g., promoters or enhancers. Thus, the expression of a transcript can be completely ablated or only decreased.

In one aspect of the invention, the engineered phenotype comprises increasing the expression of a homologous gene. This can be effected by knocking out of a negative control element, including a transcriptional regulatory element acting in cis- or trans-, or, mutagenizing a positive control element. One or more, or, all the transcripts of a cell can be measured by hybridization of a sample comprising transcripts of the cell, or, nucleic acids representative of or complementary to transcripts of a cell, by hybridization to immobilized nucleic acids on an array.

Monitoring Expression of a Polypeptides, Peptides and Amino Acids

In one aspect of the invention, the engineered phenotype comprises increasing or decreasing the expression of a polypeptide or generating new polypeptides in a cell, e.g., enzymes of the invention (e.g., DERA enzymes) or other enzymes used in the methods of the invention. This increased or decreased expression can be traced by use of a fluorescent polypeptide, e.g., a chimeric protein comprising an enzyme used in the methods of the invention. Polypeptides, reagents and end products (e.g., β,δ-dihydroxyheptanoic acid side chains or (R)-Ethyl-4-Cyano-3-Hydroxybutyrate) also can be detected and quantified by any method known in the art, including, e.g., nuclear magnetic resonance (NMR), spectrophotometry, radiography (protein radiolabeling), electrophoresis, capillary electrophoresis, high performance liquid chromatography (HPLC), thin layer chromatography (TLC), hyperdiffusion chromatography, various immunological methods, e.g. immunoprecipitation, immunodiffusion, immuno-electrophoresis, radioimmunoassays (RIAs), enzyme-linked immunosorbent assays (ELISAs), immuno-fluorescent assays, gel electrophoresis (e.g., SDS-PAGE), staining with antibodies, fluorescent activated cell sorter (FACS), pyrolysis mass spectrometry, Fourier-Transform Infrared Spectrometry, Raman spectrometry, GC-MS, and LC-Electrospray and cap-LC-tandem-electrospray mass spectrometries, and the like. Novel bioactivities can also be screened using methods, or variations thereof, described in U.S. Pat. No. 6,057,103. Polypeptides of a cell can be measured using a protein array.

EXAMPLES

Example 1

Measuring Aldolase Activity

In one aspect, an aldolase of the invention can convert fructose-1,6-diphosphate to dihydroxyacetone phosphate and glyceraldehyde-3-phosphate.

Measurement of serum aldolase activity can be of clinical significance. Elevated serum aldolase activity has been observed in certain carcinomas, muscular dystrophy, hepatitis and myocardial infarction. Aldolases of the invention can be used for determination of metabolites, e.g., in coupled enzyme reactions.

Unit activity definition: the amount of enzyme which will convert one micromole of fructose-1,6-diphosphate to dihydroxyacetone phosphate and glyceraldehyde-3-phosphate per minute at pH 7.6 and 25° C.

Assay reagents:

0.1 M Triethanolamine HCl buffer, pH 7.6.
0.008 M NADH, (5 mg/ml), NADH disodium salt in buffer.
0.033 M Fructose-1,6-diphosphate, (11.22 mg/ml) in buffer.
Glycerol-3-phosphate dehydrogenase (G3PDH) (76 U/ml) in buffer. Prepare fresh.
Triose phosphate isomerase (TPI) (480 U/ml) in buffer. Prepare fresh.
Aldolase solution—dissolve in buffer to a final concentration of 0.1 U/ml. Prepare fresh immediately prior to assay.

Protocol:

Set the spectrophotometer (equipped with a strip chart recorder and temperature control) at 340 nm and 25° C.
Into a cuvette pipette the following:

| Triethanolamine buffer | 2.7 ml |
|---|---|
| NADH solution | 0.1 ml |
| Fructose 1,6-Diphosphate (substrate) | 0.1 ml |

Mix and incubate in the spectrophotometer at 25° C. for 5 min. to achieve temperature equilibration. Record blank at 340 nm, if any.

Add the enzyme solutions to the cuvette as follows:

| Glycerol-3-phosphate dehydrogenase | 0.01 ml |
|---|---|
| Triose phosphate isomerase | 0.01 ml |
| Aldolase | 0.1 ml |

Record the change in absorbance at 340 nm for 5-10 min.

Calculate Δ 304 nm/min

Kinetic Measurements Reactions were carried out in 0.1 M phosphate buffer (pH 7.5) containing: varied concentrations of pyruvate, 2.0, 3.33, 5, and 10 mM; varied concentrations of D-arabinose, 0.2, 0.25, 0.33, and 0.50 M in 0.5 mL of solution. Each solution was incubated at 37° C. The rates for aldolase-catalyzed reactions were obtained by measuring the amount of remaining pyruvate, according the method of Kim (1988) J. Am. Chem. Soc. 110:6481. Periodically, a small aliquot (25-100 µL) was withdrawn and mixed with an assay solution (1.4 mL) containing 0.1 M phosphate (pH 7.5) buffer, 0.3 mM NADH, and 20-30 U of L-lactate dehydrogenase. The decrease in absorbance at 340 nm was measured and converted into the amount of the unreacted pyruvate using $6220 M^{-1}cm^{-1}$ for the molecular absorbance of NADH. The kinetic parameters were obtained from the Lineweaver-Burk plots. For the relative rate measurements, the concentration of pyruvate (fluoropyruvate) and sugar were fixed at 10 mM and 0.5 M, respectively. Other conditions were the same as above.

Example 2

Conversion of 3R,5S-6-chloro-2,4,6-trideoxy-erythro-hexonolactone to (3R,5R)-6-cyano-3,5,-dihydroxyhexanoic acid The invention provides processes for converting the lactone 3R,5S-6-chloro-2,4,6-trideoxy-erythro-hexonolactone (compound I of FIG. 14, see also FIG. 17 and FIG. 18) in a single step to either (3R,5S)-3,5,6-trihydroxyhexanoic acid or (3R,5R)-6-cyano-3,5,-dihydroxyhexanoic acid (FIG. 16). The former compound can be converted to rosuvastatin (CRESTOR™), fluvastatin (LESCOL™) and other statins, whereas the cyano compound can be converted to atorvastatin (LIPITOR™). Both methods can go through a common intermediate, the epoxide (-(3R,5S-3-hydroxy-4-oxiranylbutyric acid sodium salt) shown in brackets in FIG. 16.

In one aspect, an exemplary method for conversion of 3R,5S-6-chloro-2,4,6-trideoxy-erythro-hexonolactone to (3R,5R)-6-cyano-3,5,-dihydroxyhexanoic acid is: Sodium cyanide (8.93 grams) was dissolved in 12 mL water. The aqueous solution was added to 230 mL DMF, and 1 (10 grams) was added. Concentrations were 1 250 mM, NaCN 750 mM, water 5% by volume. The mixture was stirred at 40° C. for 16 hours, concentrated under reduced pressure, then acidified to pH 4 with sulfuric acid. NMR spectroscopy at a 6-hour timepoint showed the presence of 35% (3R,5R)-6-cyano-3,5,-dihydroxyhexanoic acid product, 45% of the precursor (3R,5S)-6-chloro-3,5-dihydroxyhexanoic acid, and 20% of 3R,5S-3-hydroxy-4-oxiranylbutyric acid. After 16 hours, the only product observed was (3R,5R)-6-cyano-3,5,-dihydroxyhexanoic acid.

In one aspect, an exemplary method for conversion of 1 to (3R,5S)-3,5,6-trihydroxyhexanoic acid is: NaOH (176 mg, 2.2 equivalents) was dissolved in 5 mL water. 1 was added (330 mg, 400 mM concentration. The mixture was stirred at 40° C. for 16 hours, then concentrated under reduced pressure. NMR indicated complete conversion to (3R,5S)-3,5,6-trihydroxyhexanoic acid.

Example 3

Exemplary Process for the Synthesis of Statin Intermediates

Figure 14:
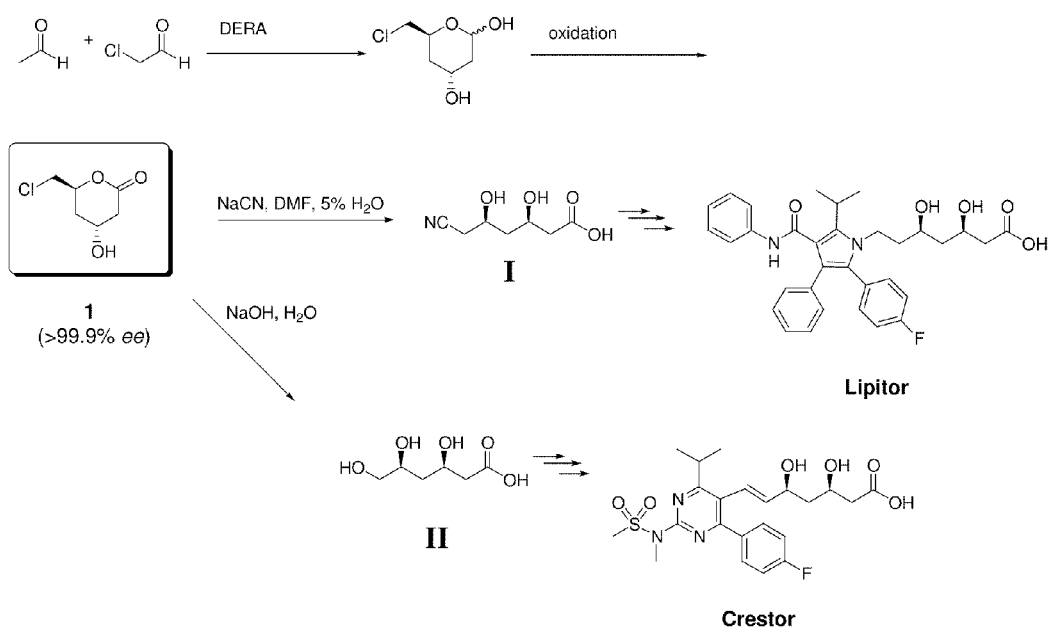
FIG. 14 illustrates exemplary syntheses using an aldolase, including DERA-catalyzed syntheses of advanced statin intermediates that can be used, e.g., in the synthesis of atorvastatin (LIPITOR™) or rosuvastatin (CRESTOR™), as described in detail, below.
Figure 15:
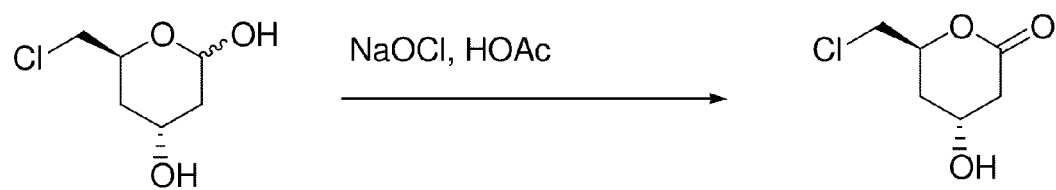
FIG. 15 illustrates an exemplary method of the invention comprising oxidation of crude chlorolactol to crystalline chlorolactone with sodium hypochlorite, as described in detail, below.
Figure 21:
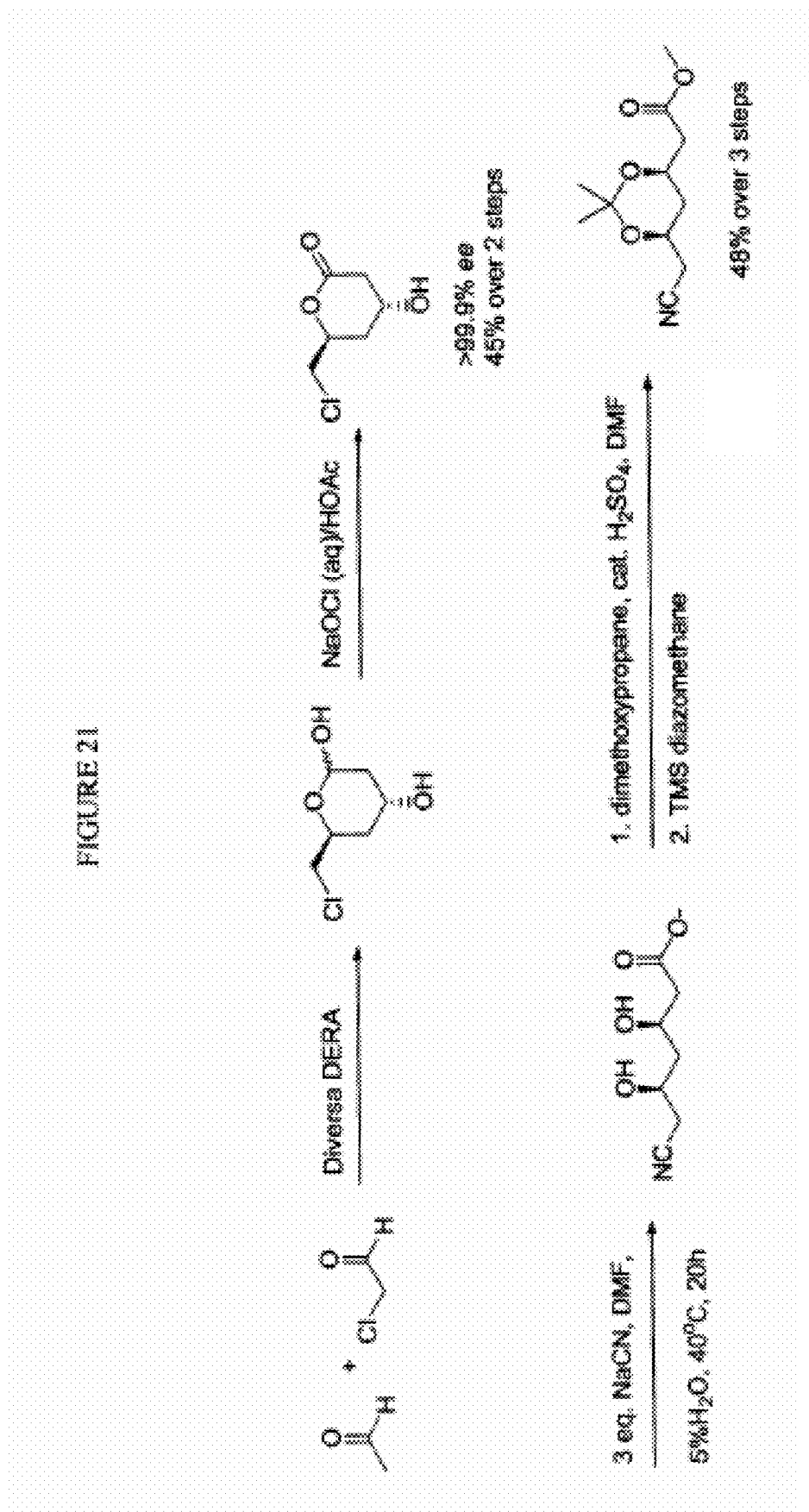
FIG. 21 illustrates exemplary process for the synthesis of statin intermediates and atorvastatin (LIPITOR™), rosuvastatin (CRESTOR™), fluvastatin (LESCOL™) and related compounds.

One exemplary process for the synthesis of statin intermediates (for, e.g., synthesis of atorvastatin (LIPITOR™), rosuvastatin (CRESTOR™), fluvastatin (LESCOL™) and related compounds) is illustrated in FIG. 21, which is an exemplary aspect of the process illustrated in FIG. 14. The first step comprises a DERA-catalyzed aldol condensation using, e.g., a DERA of the invention. 6-chloro-2,4,6-trideoxyerythro-hexonolactone is generated under conditions comprising aqueous NaOCl and HOAc. In one aspect, the yield is greater than 99.9% ee, 45% over two steps. The method further comprises processing the 3R,5S-6-chloro-2,4,6-trideoxy-erythro-hexonolactone to make (3R,5R)-6-cyano-3,5,-dihydroxyhexanoic acid (see also, compound I of FIG. 14). The last step of the process comprises dimethoxypropane, $H_2SO_4$, DMF and TMS diazomethane. The yield can be 48% over three steps.

A number of embodiments of the invention have been described. Nevertheless, it will be understood that various modifications may be made without departing from the spirit and scope of the invention. Accordingly, other embodiments are within the scope of the following claims.

What is claimed is:

1. An isolated, synthetic or recombinant polypeptide having an aldolase activity comprising:
   (i) an amino acid sequence having at least 95%, 96%, 97%, 98%, 99% sequence identity to SEQ ID NO:14;
   (ii) an amino acid sequence encoded by a nucleic acid having at least 95%, 96%, 97%, 98%, 99% sequence identity to SEQ ID NO:13;
   (iii) the amino acid sequence of (i) or (ii) lacking a signal sequence;
   (iv) the amino sequence of (i), (ii) or (iii), further comprising a heterologous peptide or polypeptide;
   (v) the amino acid sequence of (iv), wherein the heterologous peptide or polypeptide comprises a heterologous signal peptide or a heterologous prepro domain; or
   (vi) the amino sequence of (iv) or (v), wherein the heterologous polypeptide or peptide is amino terminal to, carboxy terminal to or on both ends of a signal peptide, prepro domain or catalytic domain.

2. A composition comprising the polypeptide of claim 1.

3. A heterodimer or a homodimer comprising the polypeptide of claim 1 and a second domain.

4. A chimeric polypeptide comprising at least a first domain comprising the polypeptide of claim 1, and at least a second domain comprising a heterologous polypeptide or peptide.

5. A method for preparation of a compound having a formula as set forth as intermediate II in FIG. 7, comprising the following steps:
   (a) providing an aldol donor substrate;
   (b) providing an aldol acceptor substrate;
   (c) providing an aldolase of claim 1;
   (d) admixing the aldol donor substrate of step (a), the aldol acceptor substrate of step (b), and the aldolase of step (c) under conditions wherein the aldolase can catalyze the aldol condensation reaction between the substrates of steps (a) and (b) thereby producing a compound comprising a structure as set forth as intermediate II in FIG. 7.

6. The polypeptide of claim 1, wherein the polypeptide has an aldolase activity, and wherein the aldolase activity comprises catalysis of the formation of a carbon-carbon bond; an aldol condensation; a 2-deoxyribose-5-phosphate aldolase (DERA) activity; catalysis of the condensation of acetaldehyde as donor and a 2(R)-hydroxy-3-(hydroxy or mercapto)-propionaldehyde derivative to form a 2-deoxysugar; catalysis of the condensation of acetaldehyde as donor and a 2-substituted acetaldehyde acceptor to form a 2,4,6-trideoxyhexose via a 4-substituted-3-hydroxybutanal intermediate; catalysis of the generation of chiral aldehydes using two acetaldehydes as substrates; enantioselective assembling of chiral β,δ-dihydroxyheptanoic acid side chains; enantioselective assembling of the core of [R—(R*,R*)]-2-(4-fluorophenyl)-b,d-dihydroxy-5-(1-methylethyl)-3-phenyl-4-(phenylamino)-carbonyl]-1H-pyrrole-1-heptanoic acid (atorvastatin); rosuvastatin or fluvastatin; with an oxidation step synthesis of a 3R,5S-6-chloro-2,4,6-trideoxy-erythro-hexonolactone; a thermotolerant aldolase activity; or a thermostable aldolase activity.

7. The polypeptide of claim 1, wherein the polypeptide has the amino acid sequence of SEQ ID NO: 14.

* * * * *